US009790484B2

(12) United States Patent
Wackett et al.

(10) Patent No.: US 9,790,484 B2
(45) Date of Patent: Oct. 17, 2017

(54) SILICA ENCAPSULATED BIOMATERIALS

(75) Inventors: Lawrence P. Wackett, St. Paul, MN (US); Alptekin Aksan, Minneapolis, MN (US); Michael J Sadowsky, Roseville, MN (US); Eduardo Reategui, Minneapolis, MN (US); Lisa Kasinkas, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 358 days.

(21) Appl. No.: 14/001,094

(22) PCT Filed: Feb. 22, 2012

(86) PCT No.: PCT/US2012/026031
§ 371 (c)(1),
(2), (4) Date: Nov. 5, 2013

(87) PCT Pub. No.: WO2012/116013
PCT Pub. Date: Aug. 30, 2012

(65) Prior Publication Data
US 2014/0051144 A1    Feb. 20, 2014

Related U.S. Application Data

(60) Provisional application No. 61/445,204, filed on Feb. 22, 2011.

(51) Int. Cl.
| | | |
|---|---|---|
| C12N 11/14 | (2006.01) | |
| C12N 11/04 | (2006.01) | |
| C02F 3/34 | (2006.01) | |
| C02F 3/10 | (2006.01) | |
| C02F 101/30 | (2006.01) | |
| C02F 101/36 | (2006.01) | |
| C02F 101/38 | (2006.01) | |
| C02F 103/36 | (2006.01) | |

(52) U.S. Cl.
CPC .............. *C12N 11/14* (2013.01); *C02F 3/108* (2013.01); *C02F 3/342* (2013.01); *C02F 3/348* (2013.01); *C12N 11/04* (2013.01); *C02F 3/104* (2013.01); *C02F 2101/306* (2013.01); *C02F 2101/36* (2013.01); *C02F 2101/38* (2013.01); *C02F 2103/365* (2013.01); *Y02W 10/15* (2015.05)

(58) Field of Classification Search
None
See application file for complete search history.

(56) References Cited

U.S. PATENT DOCUMENTS

| | | |
|---|---|---|
| 4,148,689 A | 4/1979 | Hino et al. |
| 4,391,909 A | 7/1983 | Lim |
| 5,200,334 A | 4/1993 | Dunn et al. |
| 5,229,096 A | 7/1993 | Cohen |
| 5,252,318 A | 10/1993 | Joshi et al. |
| 5,416,022 A | 5/1995 | Amiot |
| 5,508,193 A | 4/1996 | Mandelbaum et al. |
| 5,693,513 A | 12/1997 | Pope |
| 5,739,020 A | 4/1998 | Pope |
| 6,214,593 B1 | 4/2001 | Carturan et al. |
| 6,248,321 B1 | 6/2001 | Winder et al. |
| 6,284,522 B1 | 9/2001 | Wackett et al. |
| 6,303,290 B1 | 10/2001 | Liu |
| 6,369,299 B1 | 4/2002 | Sadowsky et al. |
| 6,495,352 B1 | 12/2002 | Brinker et al. |
| 6,673,582 B2 | 1/2004 | McTavish |
| 6,825,001 B2 | 11/2004 | Wackett et al. |
| 6,979,464 B2 | 12/2005 | Gutowska |
| 7,033,571 B2 | 4/2006 | Gutowska et al. |
| 7,052,913 B2 | 5/2006 | Babich et al. |
| 7,204,997 B2 | 4/2007 | Bromberg et al. |
| 7,510,656 B2 | 3/2009 | Shafer et al. |
| 8,337,923 B2 | 12/2012 | Coyne et al. |
| 8,367,109 B2 | 2/2013 | Chidambaram et al. |
| 9,534,236 B2 | 1/2017 | Novak et al. |
| 2001/0055797 A1 | 12/2001 | Conroy |

(Continued)

FOREIGN PATENT DOCUMENTS

| | | |
|---|---|---|
| CN | 1715182 A | 1/2006 |
| WO | WO-02/10218 A1 | 2/2002 |

(Continued)

OTHER PUBLICATIONS

Zou et al., Polymer/Silica Nanocomposites: Preparation, Characterization, Properties, and Applications, Chem. Rev. 2008, 3893-3957.*
Meunier, Christophe F., et al., "Investigation of different silica precursors: Design of biocompatible silica gels with long term bio-activity of entrapped thylakoids toward artificial leaf", Journal of Materials Chemistry, 19, (2009), 4131-4137.
"International Application Serial No. PCT/US2012/026031, International Search Report dated Jun. 6, 2012", 2 pgs.
"International Application Serial No. PCT/US2012/026031, Written Opinion dated Jun. 6, 2012", 5 pgs.
"International Application Serial No. PCT/US2012/063960, International Search Report mailed Jan. 23, 2013", 4 pgs.
"International Application Serial No. PCT/US2012/063960, Written Opinion dated Jan. 23, 2013", 8 pgs.
"Science in Action:Hydraulic Fracturing Research Study", U.S. Environmental Protection Agency (EPA) Office of Research and Development, Document No. EPS/600/F-10/002, (Jun. 2010), 2 pgs.

(Continued)

*Primary Examiner* — Suzanne M Noakes
*Assistant Examiner* — Stephen Chong
(74) *Attorney, Agent, or Firm* — Schwegman Lundberg & Woessner, P.A.

(57) ABSTRACT

The present invention relates to compositions for encapsulation of biomaterials in a silica-matrix. The present invention includes a composition for formation of a silica-matrix encapsulated biomaterial. The composition includes a reactive silicon compound and a biomaterial with a catalytic activity. When encapsulated in the silica-matrix, the biomaterial at least partially retains its catalytic activity. The present invention also relates to methods of making silica-matrix encapsulated biomaterials, and to methods of using silica-matrix encapsulated biomaterials, including methods of treating water or gas using the silica-matrix encapsulated biomaterials.

20 Claims, 22 Drawing Sheets

(56) References Cited

U.S. PATENT DOCUMENTS

| | | |
|---|---|---|
| 2005/0009159 A1 | 1/2005 | Paterek |
| 2005/0095690 A1 | 5/2005 | Naik et al. |
| 2006/0171990 A1 | 8/2006 | Asgari |
| 2009/0061496 A1 | 3/2009 | Kuhn et al. |
| 2009/0075354 A1 | 3/2009 | Reneker et al. |
| 2009/0136932 A1 | 5/2009 | Craighead et al. |
| 2009/0220378 A1 | 9/2009 | McDonnell et al. |
| 2009/0221047 A1 | 9/2009 | Schindler et al. |
| 2009/0258051 A1 | 10/2009 | Chidambaram et al. |
| 2009/0300745 A1 | 12/2009 | Dispensa |
| 2009/0305412 A1 | 12/2009 | Ying et al. |
| 2010/0055154 A1 | 3/2010 | Liao et al. |
| 2010/0190666 A1 | 7/2010 | Ali et al. |
| 2011/0165811 A1 | 7/2011 | Hill et al. |
| 2011/0259804 A1 | 10/2011 | Reitzel et al. |
| 2012/0107900 A1 | 5/2012 | Greiner et al. |
| 2012/0205041 A1 | 8/2012 | Dalborg |
| 2012/0263771 A1 | 10/2012 | Carlson et al. |
| 2014/0256007 A1 | 9/2014 | Novak et al. |
| 2014/0335148 A1 | 11/2014 | Tong et al. |
| 2015/0017683 A1 | 1/2015 | Abdullah et al. |
| 2016/0107912 A1 | 4/2016 | Novak et al. |

FOREIGN PATENT DOCUMENTS

| | | |
|---|---|---|
| WO | WO-2007129991 A1 | 11/2007 |
| WO | WO-2008/028194 A2 | 3/2008 |
| WO | WO-2008/075824 A1 | 6/2008 |
| WO | WO-2010/112820 A1 | 10/2010 |
| WO | WO-2011011468 A2 | 5/2011 |
| WO | WO-2012/064287 A1 | 5/2012 |
| WO | WO-2012/116013 A3 | 8/2012 |
| WO | WO-2012116013 A2 | 8/2012 |
| WO | WO-2013070778 A1 | 5/2013 |
| WO | WO 2014/182799 A1 | 11/2014 |

OTHER PUBLICATIONS

Brinker, C. J, et al., "Sol-Gel Science: The Physics and Chemistry of Sol-Gel Processing", Pgs. from Chapter 3: Hydrolysis and Condensation II-Silicates, Academic Press, Inc. San Diego, CA, (1990), 99-107.

Dickson, D J, et al., "Photobiological hydrogen production from *Synechocystis* sp. PCC 6803 encapsulated in silica sol-gel", International Journal of Hydrogen Energy, Elsivier Science Publishers B. V. Banking, GB vol. 34, No. 1, (Jan. 1, 2009), 204-215.

Ho, C, et al., "Enzymatic properties of atrazing chlorohydrolase entrapped in biomemetic silca", J. Appl. Biol. Chem. vol. 51, (2008), pp. 143-147.

Kauffmann, C, et al., "entrapment of altrazin chlorohydrase in sol-gel glass matric.", Journal of Biotechnology vol. 62, (1998), pp. 169-176.

Kauffmann, C., et al., "Entrapment of atrazine chlorohydrolase in sol-gel glass matrix", Journal of Biotechnology, 62, (1998), 169-176.

Kauffmann, C., et al., "Novel Methodology for Enzymatic Removal of Atrazine from Water by CBD-Fusion Protein Immobilized on Cellulose", Environ. Sci. Technol., 34, (2000), 1292-1296.

Kirby, J. R, "Designer bacteria degrades toxin", Nat Chem Biol., 6(6), (Jun. 2010), 398-9.

Ma, T., et al., "Enhancement of atrazine degradation by crude and immobilized enzymes in two agricultural soils", Environ Earth Sci., Online Publication, (2011), 7 pgs.

Ma, Y., et al., "The Research of Immobilized Atrazine Degrading Bacteria Degrading Characteristics", International Conference on Environmental Science and Information Application Technology, 2009. ESIAT 2009, vol. 1, (2009), 677-680.

Macias-Flores, A., et al., "Atrazine biodegradation by a bacterial community immobilized in two types of packed-bed biofilm reactors", World J Microbiol Biotechnol., 25, (2009), 2195-2204.

Mantsch, H. H, et al., "Infrared Spectroscopy of Biomolecules", Pg. from Chapter 9, Section 9.7.2.1, Wily-Liss, Inc., New York, (1996), 266.

Meunier, C F, et al., "Encapsulation of cells within silica matrixes: Towards a new advance in the conception of living hybrid materials", Journal of Colloid and Interface Science, Acadamic Press, New York, NY, US, vol. 342, No. 2, (Feb. 15, 2010), 211-224.

Nedovic, V., et al., "", Fundamentals of Cell Immobilization Biotechnology, Adapted from p. 15, Part 1, 15.

Reategui, E., et al., "Encapsulation of Mammalian Cells in Hybrid Inorganic Matrices for Developing Bio-detection Applications", Alley Conference 2010, Poster, (2010).

Reategui, E., et al., "Silica gel-encapsulated AtzA biocatalyst for atrazine biodegradation", Appl Microbiol Biotechnol., [Epub ahead of print], (Jan. 7, 2012), 10 pgs.

Reetz, Manfred T., "Chapter 6—Practical Protocols for Lipase Immobilization", Immobilization of Enzymes and Cells, Second Edition—Edited by Jose M. Guisan, (2006), 66.

Riddle, Kathryn W, et al., "Biomaterials for Cell Immobilization: A look at carrier design", Kathryn W. Riddle and David J. Mooney University of Michigan, Chemical Engineering, 19 pages.

Ruiz-Hitzky, Eduardo, et al., "An Introduction to Bio-nanohybrid Materials", Bio-inorganic Hybrid Nanomaterials, Edited by Eduardo Ruiz-Hitzky, Katsuhiko Ariga and Yuri Lvov, (2008), 1.

Shona, Pek Y, et al., "A thixotropic nanocomposite gel for three-dimensional cell culture", Nature Nanotechnology vol. 3, No. 11, (Sep. 28, 2008), 671-675.

Siripattanakul, S., et al., "Atrazine removal in agricultural infiltrate by bioaugmented polyvinyl alcohol immobilized and free Agrobacterium radiobacter J14a: A sand column study", Chemosphere, 74, (2009), 308-313.

Tafoya-Garnica, A., et al., "Kinetics of atrazine biodegradation by suspended and immobilized mixed microbial cells cultivated in continuous systems", Journal of Chemical Technology & Biotechnology, 84(7), (Jul. 2009), 982-991.

Vivek, Kandimalla, et al., "Immobilization of Biomolecules in Sol-Gels Biological and Analytical Applications", Critical Reiviews in Analytical Chemistry, vol. 36, No. 2, (Jul. 1, 2006), 73-106.

Wright, J. D, "Sol-Gel Materials: Chemistry and Applications", Chapter 2: Silica Sol-Gels: Reaction Mechanisms, Gordon and Breach Science Publishers, (2001), 15-31.

Yu, M., et al., "RNA sequencing of pancreatic circulating tumour cells implicates WNT signalling in metastasis", Nature, 487(7408), (2012), 510-515.

"Canadian Application Serial No. 2,827,559, Voluntary Amendment dated Jun. 18, 2014", 18 pgs.

"Chinese Application Serial No. 201280016435.4, Office Action dated Jan. 26, 2015", (w/ English Translation), 17 pgs.

"European Application Serial No. 12748999.5, Extended European Search Report dated Apr. 1, 2015", 8 pgs.

"International Application Serial No. PCT/US2012/026031, International Preliminary Report on Patentability dated Mar. 27, 2014", 7 pgs.

"International Application Serial No. PCT/US2012/063960, International Preliminary Report on Patentability dated May 22, 2014", 8 pgs.

Kandimalla, Vivek B., et al., "Immobilization of Biomolecules in Sol-Gels: Biological and Analytical Application", *Critical Review in Analytical Chemistry*, 36(2), (Jul. 1, 2006), 73-106.

"U.S. Appl. No. 14/198,104, Non Final Office Action dated Jan. 11, 2016", 13 pgs.

"U.S. Appl. No. 14/198,104, Response filed May 11, 2016 to Non Final Office Action dated Jan. 11, 2016", 15 pgs.

"U.S. Appl. No. 14/198,104, Response filed Sep. 17, 2015 to Restriction Requirement dated Jul. 17, 2015", 7 pgs.

"U.S. Appl. No. 14/198,104, Restriction Requirement dated Jul. 17, 2015", 5 pgs.

"U.S. Appl. No. 14/271,958, Preliminary Amendment dated Aug. 28, 2014", 3 pgs.

"U.S. Appl. No. 14/271,958, Restriction Requirement dated Sep. 28, 2015", 6 pgs.

"Application Serial No. PCT/US2014/037128, International Preliminary Report on Patentability dated Nov. 19, 2015", 9 pgs.

"International Application Serial No. PCT/US2014/037128, International Search Report dated Aug. 20, 2014", 6 pgs.

(56) References Cited

OTHER PUBLICATIONS

"International Application Serial No. PCT/US2014/037128, Written Opinion dated Aug. 20, 2014", 7 pgs.

"Russian Application Serial No. 2013142684, Office Action dated Nov. 28, 2013", 4 pgs.

"Russian Federation Application Serial No. 2013142684, Office Action dated Dec. 4, 2015", (w/ English Translation), 9 pgs.

Ferrer, Marla L., et al., "Biocompatible Sol-Gel Route for Encapsulation of Living Bacteria in Organically Modified Silica Matrixes", *Chemistry of Materials*, 15(19), (2003), 3614-3618.

Fung, W.-Y., et al., "Agrowaste-Based Nanofibers as a Probiotic Encapsulant: Fabrication and Characterization", *Journal of Agricultural and Food Chemistry*, 59(15), (2011), 8140-8147.

Gensheimer, M., et al., "Novel Biohybrid Materials by Electrospinning: Nanofibers of Poly(ethylene oxide) and Living Bacteria", *Advanced Materials*, 19, (2007), 2480-2482.

Gensheimer, M., et al., "Polymer/Bacteria Composite Nanofiber Nonwovens by Electrospinning of Living Bacteria Protected by Hydrogel Microparticles", *Macromolecular Bioscience*, 11(3), (2011), 333-337.

Kauffman, Carl, et al., "Entrapment of atrazine chlorohydrolase in sol-gel glass matrix", *Journal of Biotechnology*, 62, (1998), 169-176.

Klein, S., et al., "Encapsulation of Bacterial Cells in Electrospun Microtubes", *Biomacromolecules*, 10(7), (2009), 1751-1756.

Klein, S., et al., "Encapsulation of *Pseudomonas* sp. ADP cells in electrospun microtubes for atrazine bioremediation", *Journal of Industrial Microbiology & Biotechnology*, 39(11), (2012), 1605-1613.

Liu, Y., et al., "Engineering of bio-hybrid materials by electrospinning polymer-microbe fibers", *Proc. Natl. Acad. Sci. USA*, 106(34), (2009), 14201-14206.

Lopez-Rubio, A., et al., "Electrospinning as a useful technique for the encapsulation of living bifidobacteria in food hydrocolloids", *Food Hydrocolloids*, 28(1), (2012), 159-167.

Lopez-Rubio, A., et al,, "Encapsulation of Living Bifidobacteria in Ultrathin PVOH Electrospun Fibers", *Biomacromolecules* 10, (2009), 2823-2829.

Mutlu, Baris R., et al., "Silicon alkoxide cross-linked silica nanoparticle gels for encapsulation of bacterial biocatalysts", *Journal of Materials Chemistry A*, (2013), 10 pgs.

Patel, Alfa C, et al., "In Situ Encapsulation of Horseradish Peroxidase in Electrospun Porous Silica Fibers for Potential Biosensor Applications", *Nano Letters*, vol. 6, No, 5, (May 1, 2006), 1042-1046.

Rietti-Shati, M, et al., "Atrazine Degradation by Pseudomonas strain ADP Entrapped in Sol-Gel Glass", *Journal of Sol-Gel Science and Technology*, vol. 7, No. 1-2, (1996), 77-79.

Rim, N. G., et al,, "Current approaches to electrospun nanofibers for tissue engineering", Biomedical Materials, 8(1), (2013), 1-14.

Salalha, W., et al., "Encapsulation of bacteria and viruses in electrospun nanofibres", *Nanotechnology*, 17, (2006), 4675-4681.

Srivastava, Y., et al., "Electrospinning of hollow and core/sheath nanofibers using a microfluidic manifold", *Microfluidics and Nanofluidics*, 4(3), (2007), 245-250.

Zhang, X., et al., "Flexible Generation of Gradient Electrospinning Nanofibers Using a Microfluidic Assisted Approach", *Langmuir*, 28(26), (2012), 10026-10032.

Zussman, E., "Encapsulation of cells within electrospun fibers", *Polymers for Advanced Technologies*, 22(3), (2011), 366-371.

"Russian Federation Application Serial No. 2013142684, Office Action dated Dec. 4, 2015", 9 pgs.

Ferrer, M, et al., "Biocompatible sol-gel route for encapsulation of living bacteria in organically modified silica matrixes", Chemistry of materials, v.15, No. 19, (2003), 3614-3618 pgs.

Kauffman, C, et al., "Entrapment of atrazine chlorohydrolase in sol-gel glass matrix", Journal of Biotechnology, v.62, (1998), 169-176 pgs.

Rietti-Shati, M, et al., "Atrazine Degradation by Pseudomonas strain ADP Entrapped in Sol-Gel Glass", Journal of Sol-Gel Science and Technology, v.7, No. 1-2, (1996), 77-79 pgs.

"European Application Serial No. 12748999.5, Response filed Oct. 16, 2015 to Extended European Search Report dated Apr. 1, 2015", 6 pgs.

"U.S. Appl. No. 14/198,104, Notice of Allowance dated Jul. 29, 2016", 8 pgs.

"U.S. Appl. No. 14/198,104, PTO Response to Rule 312 Communication dated Dec. 5, 2016", 4 pgs.

"Australian Application Serial No. 2012220738, First Examiner Report dated Oct. 5, 2016", 3 pgs.

"European Application Serial No. 12748999.5, Office Action dated Jan. 25, 2017".

\* cited by examiner

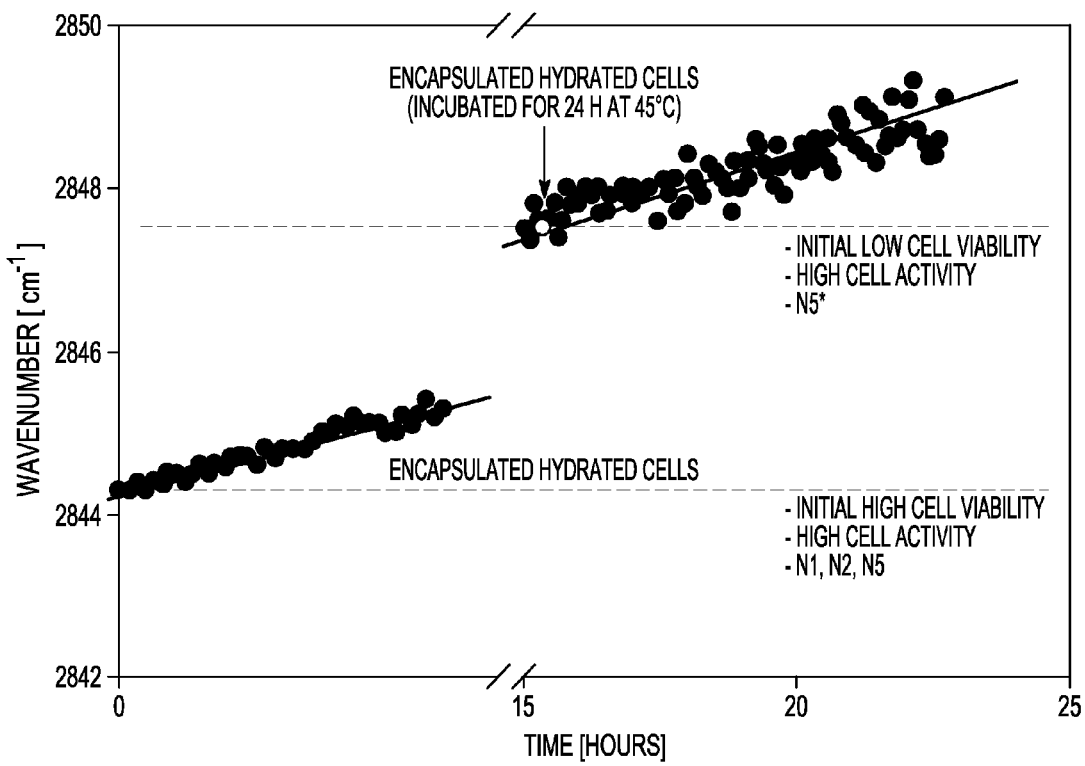
FIG. 21
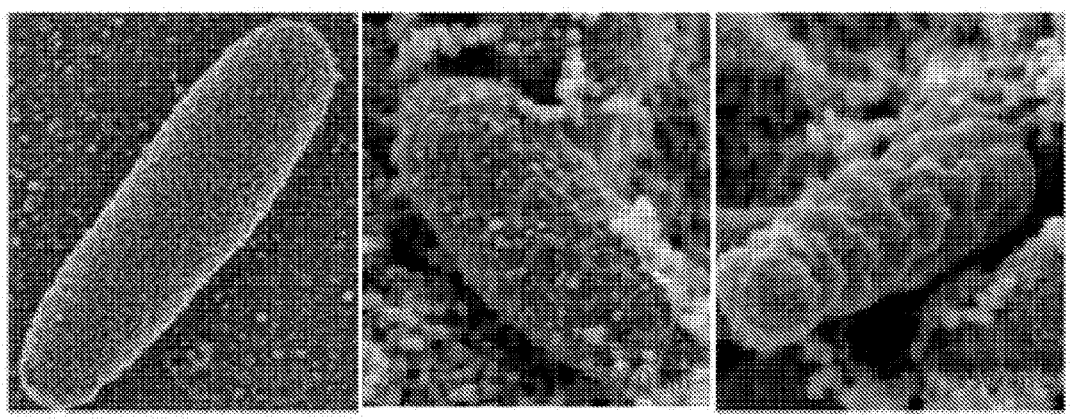
FIG. 22A   FIG. 22B   FIG. 22C

SILICA ENCAPSULATED BIOMATERIALS

This application is a U.S. National Stage Filing under 35 U.S.C. 371 from International Application No. PCT/US2012/026031, filed on 22 Feb. 2012, and published as WO 2012/116013 A2, on 30 Aug. 2012, which claims priority under 119(e) to U.S. Provisional Patent Application Ser. No. 61/445,204, filed 22 Feb. 2011, which applications and publications are incorporated herein by reference in their entirety.

STATEMENT OF GOVERNMENT SUPPORT

This invention was made with government support under grant number 0644784 awarded by the National Science Foundation (NSF). The government has certain rights in this invention.

BACKGROUND OF THE INVENTION

Biomaterials often exhibit properties that can have utility in a wide variety of applications. The metabolic functionality of biomaterials can have extensive applications in biotechnology (e.g. biosensing, biocatalysis, bioremediation, and bioreactors), medicine (e.g. regenerative medicine, tissue engineering, and recombinant protein production), and in new hybrid materials with improved functional and structural properties. One example of a useful property exhibited by biomaterials is the catalytic activity exhibited by enzymes. For example, the catalytic activity of enzymes can be useful for chemical transformations on a small-scale in a chemistry lab, in large-scale industrial chemical manufacturing or purification operations, in agricultural settings, in food products, and in water treatment.

Biomaterials are frequently difficult to utilize in their natural state. The useful applications described above are difficult to achieve without some way to immobilize the biomaterial. Without immobilization, enzymes with a useful activity or microorganisms that express an enzyme with useful activity can be easily washed away from a desired site of application. Immobilization can allow repeated use without requiring separation and purification of the enzyme or addition of new catalysts. However, to enable practical application of their useful activities, successful immobilization of microorganisms depends on a highly biocompatible encapsulation material of sufficient mechanical robustness that permits the entry of small molecules such as $O_2$, nutrients, electrolytes, and exit of toxic metabolites, hormones, and other bioactive compounds. While the immobilization of microorganisms has been attempted using various substrates and techniques, traditional materials used for cell encapsulation have limited the development of biotechnology and medical applications due to the instability of the biomaterial over long periods of time. Problems with stability can include limited or no catalytic activity expressed by an immobilized enzyme or by an immobilized microorganism that expresses the particular enzyme. Problems with stability can also sometimes include death of the microorganism, although short- or long-term survival of the microorganism is not always required in all applications. Additionally, the mechanical properties of polymeric synthetic and natural materials used for cell encapsulation can be drastically altered by the metabolically active encapsulated cells.

In the past, many problems have been experienced in immobilization of macromolecules, specifically, microorganisms. For example, when immobilizing microorganisms using silica nanoparticles, the proteins from the microorganisms can be adsorbed into the silica nanoparticles, which can cause denaturation and aggregation of the adsorbed proteins and therefore loss of structure and catalytic activity. Traditional microorganism immobilization protocols can also lead to adsorption and denaturation when temperatures are increased. When encapsulation procedures include hydrolysis or condensation steps, the procedure can require additional steps to remove the byproducts of the hydrolysis or condensation reactions. When encapsulation procedures include the use of colloidal precursors such as sodium or potassium silicate, the removal of the sodium or potassium ions can be required.

Atrazine is a widely used herbicide. As a result, atrazine can be found in soil, groundwater and surface water. There is currently extensive interest in identifying an efficient way to transform atrazine into hydroxyatrazine. Hydroxyatrazine is not regulated, it adsorbs more tightly to soil particle than atrazine, and also degrades more rapidly in the environment. The approaches for atrazine remediation are very diverse and include use of free enzymes (atrazine chlorohydrolase) or the microorganisms that express these enzymes. When enzymes or microorganisms are used they are usually added into the soil to eliminate the contaminants. However, this approach is not practical for water treatment applications. A method that can immobilize microorganisms while maintaining their enzymatic abilities is needed.

SUMMARY OF THE INVENTION

The present invention provides compositions for encapsulation of biomaterials in a silica-matrix. The present invention also provides methods of making silica-matrix encapsulated biomaterials, and methods of using silica-matrix encapsulated biomaterials.

The present invention provides certain surprising and advantageous aspects over past compositions and methods for encapsulation of biomaterials. For example, the biomaterials encapsulated by the compositions and methods of the present invention retain their useful activity after encapsulation for extended periods of time, which can enable useful and practical application of the biomaterials. Embodiments of the compositions and methods of the present invention help to avoid denaturation and deactivation of the encapsulated biomaterials. In some embodiments of the present invention, silica-matrix encapsulated microorganisms and the compounds therein retain their structure and activity even at harsh conditions of pH or temperature. Some embodiments of the present invention can avoid additional steps of removing hydrolysis or condensation byproducts. Some embodiments of the present invention can avoid additional steps of removing ions such as sodium or potassium. In an embodiment of the present invention, a microorganism that can express the enzyme that chemically transforms atrazine into other compounds, can be immobilized with retention of the useful enzymatic activity, allowing practical use of the enzyme for decreasing the atrazine-content in water or other media.

The present invention provides a composition for formation of a silica-matrix encapsulated biomaterial. The composition includes a reactive silicon compound. The composition also includes a biomaterial. The biomaterial has a catalytic activity prior to encapsulation. The composition of the present invention is such that when the biomaterial is encapsulated in the silica-matrix, the biomaterial at least partially retains the catalytic activity it had prior to encapsulation.

The present invention provides a method for making a silica-matrix encapsulated biomaterial. The method includes providing a reactive silicon compound. The method also includes adding a biomaterial. The biomaterial has a catalytic activity prior to encapsulation. The method also includes forming a silica-encapsulated biomaterial from the reactive silicon composition. The silica-encapsulated biomaterial at least partially retains the catalytic activity it had prior to encapsulation.

The present invention provides a composition for formation of a silica-matrix encapsulated bacteria. The composition includes a reactive silicon compound. The composition also includes bacteria. The bacteria have a catalytic activity prior to encapsulation. The catalytic activity of the bacteria can be due, for example, to an enzyme expressed by the bacteria. The composition also includes an organic precursor. The organic precursor includes at least one of a synthetic polymer or monomer, a natural polymer or monomer, an amino acid, a saccharide, or a polysaccharide. The pH of the composition is adjusted sufficiently to allow formation of the silica-matrix encapsulated bacteria. The silica-matrix encapsulated bacteria can form within about 5 minutes to about 24 hours. The silica-encapsulated bacteria totally or partially retains the catalytic activity they had prior to encapsulation.

The present invention provides a composition for formation of a silica-matrix encapsulated bacteria. The composition includes a reactive silicon compound. The composition also includes bacteria. The bacteria express the enzyme atrazine chlorohydrolase. The bacteria have a catalytic activity prior to encapsulation. The catalytic activity of the bacteria can be due to the atrazine chlorohydrolase enzyme expressed by the bacteria. The composition also includes an organic precursor. The organic precursor includes at least one of a synthetic polymer or monomer, a natural polymer or monomer, an amino acid, a saccharide, or a polysaccharide. The pH of the composition can be adjusted sufficiently to allow formation of the silica-matrix encapsulated bacteria. The silica-matrix encapsulated bacteria can form within about 5 minutes to about 24 hours. The silica-encapsulated bacteria at least partially retains the catalytic activity it had prior to encapsulation.

The present invention provides a method of making a silica-matrix encapsulated bacteria. The method includes providing a reactive silicon compound. The method also includes adding an organic precursor. The organic precursor includes at least one synthetic polymer or monomer, a natural polymer or monomer, an amino acid, a saccharide, or a polysaccharide. The method also includes adding bacteria. The bacteria have catalytic activity prior to encapsulation. The catalytic activity of the bacteria can be due to, for example, to enzymes expressed by the bacteria. The method includes adjusting the pH of the reactive silicon compound composition sufficiently to allow gelation of the composition within about 5 min to about 24 hours. The method also includes forming silica-encapsulated bacteria from the reactive silicon composition. The silica-encapsulated bacteria at least partially retains the catalytic activity it had prior to encapsulation.

The present invention provides a method of treating a medium. The method includes exposing a medium containing a chemical to a biomaterial. The biomaterial has a catalytic ability that includes conversion of the chemical to a different chemical. The contacting sufficient to transform at least some of the chemical to a different chemical. The biomaterial is encapsulated in a silica matrix. Specific examples of the medium include water or gas, or combinations thereof. Specific examples of the method of treating a medium include a method of treating atrazine-containing water, fracking water, or a method of treating a gas, including a gas included in a mixture of gases or a gas dissolved in a liquid.

The present invention provides a method of treating water. The method includes exposing water to a biomaterial with a catalytic ability. The catalytic ability includes conversion of a chemical to a less toxic compound. The biomaterial is encapsulated in a silica-matrix.

The present invention provides a method of treating fracking water. The method includes exposing fracking water to a biomaterial with a catalytic ability. The catalytic ability includes conversion of a fracking chemical to a less toxic compound. The biomaterial is encapsulated in a silica-matrix.

The present invention provides a method of treatment of atrazine-containing water. The method includes exposing atrazine-containing water to bacteria. The bacteria express the enzyme atrazine chlorohydrolase. The exposure of the atrazine-containing water to the atrazine-degrading bacteria is sufficient to reduce the atrazine content of the water. The bacteria is encapsulated in a silica-matrix.

The present invention provides a method of treating a gas. The method includes exposing a gas to a biomaterial with a catalytic ability. The catalytic ability includes conversion of a gas to a less flammable, less explosive, or less toxic compound. The biomaterial is encapsulated in a silica-matrix.

BRIEF DESCRIPTION OF THE FIGURES

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

The patent or application file contains at least one drawing executed in color. Copies of this patent or patent application publication with color drawing(s) will be provided by the Office upon request and payment of the necessary fee.

FIG. 21 illustrates the v-$CH_2$ peak position of encapsulated *E. coli* expressing AtzA in silica gels, in accord with various embodiments.

FIGS. 22A, B, and C illustrate electron microscopy images of *E. coli* expressing AtzA, in accord with various embodiments.

DETAILED DESCRIPTION OF THE INVENTION

Figure 1A:
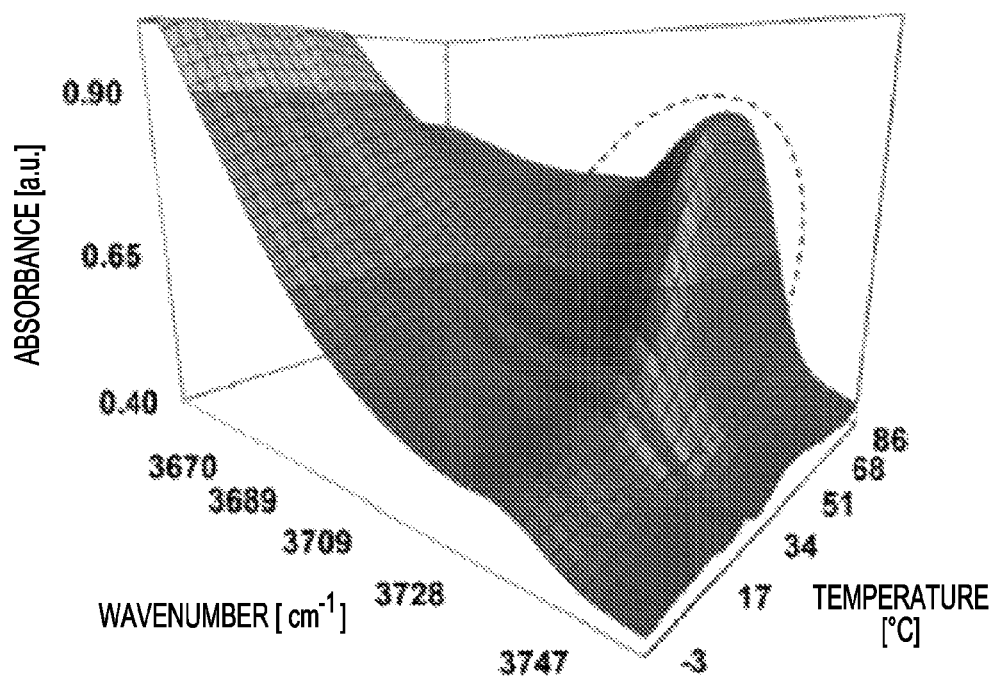
FIG. 1A illustrates the presence of silanol (—SiOH) groups on the surface matrix, in accord with certain embodiments.

Reference will now be made in detail to certain claims of the disclosed subject matter, examples of which are illustrated in the accompanying drawings. While the disclosed subject matter will be described in conjunction with the enumerated claims, it will be understood that they are not intended to limit the disclosed subject matter to those claims. On the contrary, the disclosed subject matter is intended to cover all alternatives, modifications, and equivalents, which can be included within the scope of the presently disclosed subject matter as defined by the claims.

References in the specification to "one embodiment", "an embodiment", "an example embodiment", etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a concentration range of "about 0.1% to about 5%" should be interpreted to include not only the explicitly recited concentration of about 0.1 wt % to about 5 wt %, but also the individual concentrations (e.g., 1%, 2%, 3%, and 4%) and the sub-ranges (e.g., 0.1% to 0.5%, 1.1% to 2.2%, 3.3% to 4.4%) within the indicated range.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited. Recitation in a claim to the effect that first a step is performed, then several other steps are subsequently performed, shall be taken to mean that the first step is performed before any of the other steps, but the other steps can be performed in any suitable sequence, unless a sequence is further recited within the other steps. For example, claim elements that recite "Step A, Step B, Step C, Step D, and Step E" shall be construed to mean step A is carried out first, step E is carried out last, and steps B, C, and D can be carried out in any sequence between steps A and E, and that the sequence still falls within the literal scope of the claimed process. A given step or sub-set of steps can also be repeated.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The following documents are hereby incorporated by reference: "Atrazine removal in agricultural infiltrate by bioaugmented polyvinyl alcohol immobilized and free *Agrobacterium* radiobacter J14a: A sand column study," S. Siripattanakul, W. Wirojanagud, J. M. McEvoy, F. X. M. Casey, E. Khan, Chemosphere 74 (2009) 308-313, "Entrapment of atrazine chlorohydrolase in sol-gel matrix," C. Kauffmann, R. Mandelbaum, Journal of Biotechnology 62 (1998) 169-176, "Novel Methodology for enzymatic removal of atrazine from water by CBD-fusion protein immobilized on cellulose," C. Kauffmann, O. Shoseyov, E. Shpigel, E. A. Bayer, R. Lamed, Y. Shoham, R. T. Mandelbaum, Environ. Sci. Technol. 2000. 34, 1292-1296, "Kinetics of atrazine degradation by suspended and immobilized mixed microbial cells cultivated in continuous systems," A. Tafoya-Garnica, A. Marcias-Flores, N. Ruiz-Ordaz, Cleotilde Juarez-Ramirez, Juvencio Galindez-Mayer, J. Chem. Technol. Biotechnol 2009, 84, 982-991, "The research of immobilized atrazine degrading bacteria degrading characteristics," Y. Mao, Y. Ma, Z. Jiang, R. Wang, Y. Zhang, 2009 International Conference on Environmental Science and Information Application Technology, "Designer Bacteria degrades toxin," J. R. Kirby, Nature Chemical Biology, 2010, Vol 6, 398-399, "Mixed bacterial culture for atrazine degradation," Inventors: D. Hrsak, M. Havriluk, U.S. Pat. No. 7,658,850 B2, February 2010, "Enhancement of atrazine degradation by crude and immobilized enzymes in two agricultural soils," T. Ma, L. Zhu, J. Wang, J. Wang, H. Xie, J. Su, Q. Zhang, B. Shao. Eviron. Earth Sci: DOI 10.1007/s12665-011-0910-6.

Definitions

The singular forms "a," "an" and "the" can include plural referents unless the context clearly dictates otherwise.

The term "about" can allow for a degree of variability in a value or range, for example, within 10%, or within 5% of a stated value or of a stated limit of a range.

The term "independently selected from" refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "cell" as used herein refers to bacteria, archaea, protist, or fungi.

The term "microorganism" as used herein refers to bacteria, archaea, protist, or fungi.

The term "biomaterial" refers to one or more microorganisms, cells, or enzymes such as enzymes within a cell or microorganism or enzymes not within a cell or microorganism (free enzymes). As used herein, the term "biomaterial" does not include mammalian cells. Examples of biomaterials include enzymes, macromolecules, and non-mammalian cells, such as for example bacteria, archaea, protists, or fungi.

The term "pore" as used herein refers to a depression, slit, or hole of any size or shape in a solid object. A pore can run all the way through an object or partially through the object. A pore can intersect other pores.

The term "silicate" as used herein refers to any silicon-containing compound wherein the silicon atom has four bonds to oxygen, wherein at least one of the oxygen atoms bound to the silicon atom is ionic, such as any salt of a silicic acid. The counterion to the oxygen ion can be any other suitable ion or ions. An oxygen atom can be substituted with other silicon atoms, allowing for a polymer structure. One or more oxygen atoms can be double-bonded to the silicon atom; therefore, a silicate molecule can include a silicon atom with 2, 3, or 4 oxygen atoms. Examples of silicates include aluminum silicate. Zeolites are one example of materials that can include aluminum silicate. A silicate can be in the form of a salt, ion, or a neutral compound.

The term "silica" as used herein can refer to silicon dioxide ($SiO_2$) of any particle size, shape, particle size distribution, shape distribution and surface functionality, including chemically treated silicas. It can also refer to a polysiloxane.

The term "silica gel" or "silica matrix" as used herein can refer to a substance that includes silica or a polysiloxane. The polysiloxane includes at least in part a silicon-oxygen-silicon (silicon atom bonded to oxygen atom bonded to silicon atom) chemical structure, wherein the compound can be a polymer of any length or degree of branching. The silica gel or matrix can include polysiloxanes in 30%, 50%, 80%, 90%, 95%, 99%, 99.5%, 99.9%, or in any suitable percent composition (wt %). A silica gel or silica matrix also can refer to a substance that includes at least in part a silicon-oxygen-carbon chain-oxygen-silicon chemical structure, wherein the compound can be a polymer of any length or degree of branching.

The term "acid" as used herein refers to hydrochloric acid, phosphoric acid, nitric acid, sulfuric acid, acetic acid, citric acid, formic acid, propionic acid, oxalic acid, carbonic acid, or any other inorganic or organic aqueous acid.

The term "fracking water" as used herein refers to water used in or produced from a hydraulic fracturing process. For example, fracking water includes any water that are released, or polluted at any time during hydraulic fracturing for oil or gas.

The term "fracking chemical" as used herein refers to any chemical compound used (e.g. added to the water to enhance the fracking process), produced, or absorbed during a fracking process that can be dissolved, suspended, or forming multiple phases with the fracking water before, during, or after the fracking process is performed.

The term "gas abatement" as used herein refers to a process that transforms a gas into another material that is less flammable, less toxic, or less explosive than the starting material gas.

Description

The present invention provides compositions for encapsulation of biomaterials in a silica-matrix. The present invention also provides methods of making silica-matrix encapsulated biomaterials, and to methods of using silica-matrix encapsulated biomaterials.

The present invention can enable new and useful application of biomaterials in biotechnology (e.g. biosensing, biocatalysis, bioremediation, and bioreactors) and medicine (e.g. regenerative medicine, tissue engineering, and recombinant protein production), and in new hybrid materials with improved functional and structural properties.

Methods of Forming the Silica-Matrix Encapsulated Biomaterial

There are two primary methods to form silica the reactive silicon compound.

Hydrolysis Route.

The route includes hydrolysis of alkoxide precursors under acidic or basic conditions in the presence of water. The water/alkoxide molar ratios may vary from 2 to 50. Hydrolysis of the alkoxide leads to the formation of silanol moieties (Si—OH) that are very reactive.

A hydrolysis reaction can be illustrated as follows:

≡Si—OR+H$_2$O ↔ ≡Si—OH+R—OH.

Wherein ≡ represents three total bonds, and not necessarily a triple bond.

Alkali Metal Silicate Route.

The route includes the acid treatment of silicate solutions. Typically, sodium silicate solutions with SiO$_2$ content between 27 to 30% are used. A dilution in water of the metal silicate can be prepared first in order to reduce the amount of acid that needs to be added. Acid treatment of silicates leads to the formation of silanol moieties (Si—OH) that are very reactive.

After formation of the reactive silicon compound, condensation reactions can occur to form the silica-matrix in a gelation process. Through condensation, these silanol moieties react further and form siloxanes (—Si—O—Si—). Additionally, silica nanoparticles of different sizes (e.g., Ludox® or Nyacol®) can also be added to the sodium silicate solution to increase the stiffness of the silica matrix.

Through condensation of silanol with other silanols and/or siloxanes, an interconnected rigid network with pores of submicrometer dimensions and polymeric chains of SiO$_2$ is formed (gelation). There is very little or no heat absorption or release at the gel point; only the sudden increase in viscosity. The initial gel has a high viscosity but low elasticity. Following gelation, further crosslinking and chemical inclusion of isolated sol particles into spanning cluster continues (aging), leading to an increase in the elasticity of the sample. In the bio-confinement process, the biomolecules or cells are usually added after the hydrolysis step, therefore, the cells are confined in a 3-D nanoporous network after the condensation reactions.

In one example, an alkoxysilane can condense with a silanol to give an SiO2 bond with generation of an alcohol, illustrated as follows:

≡Si—OR+HO—Si≡ ↔ ≡Si—O—Si≡+R—OH.

Wherein ≡ represents three total bonds, and not necessarily a triple bond.

Similarly, a silanol can condense with any hydroxyl- or alkoxy-bearing group to give water or an alcohol, respectively.

In another example, a silanol can condense with another silanol, illustrated as follows:

≡Si—OH+HO—Si≡ ↔ ≡Si—O—Si≡+H$_2$O.

Wherein ≡ represents three total bonds, and not necessarily a triple bond.

Table 1 below shows a non-limiting list of preferred sources ("inorganic precursors") that can be used for the preparation of a reactive silicon compound using the hydrolysis or the alkali metal silicate route. In general, any alkoxide precursor that has hydrolysable groups can be used to form a reactive silicon compound via hydrolysis. In general, any metal silicate can be used for to give a reactive silicon compound with treatment with acid. Examples of preferred metals include sodium and potassium.

TABLE 1

Examples of Typical Inorganic Precursors

| Chemical Name | Acronym | Molecular Formula | Reactive Groups | Non-reactive group |
| --- | --- | --- | --- | --- |
| Network Formers | | | | |
| Tetramethylorthosilicate | TMOS | Si(OCH$_3$)$_4$ | —OH | — |
| Tetramethylorthosilicate | TEOS | Si(OC$_2$H$_5$)$_4$ | —OH | — |
| Tetrakis(2-hydroxyethyl)orthosilicate | THEOS | Si(OCH$_2$CH$_2$OH)$_4$ | —OH | — |
| Methyldiethoxysilane | MDES | C$_5$H$_{14}$O$_2$Si | —OH | —CH3, —H |
| 3-(Glycidoxypropyl)triethoxysilane | GPMS | C$_9$H$_{20}$O$_5$Si | —OH, epoxy ring | — |
| 3-(Trimethoxysilyl)propylacrylate | TMSPA | H$_2$C=CHCO$_2$(CH$_2$)$_3$Si(OCH$_3$)$_3$ | —OH, acrylate group | — |
| N-(3-Triethoxysilylpropyl)pyrrole | TESPP | | —OH, pyrrole group | — |
| Vinyltriethoxysilane | VTES | H$_2$C=CHSi(OC$_2$H$_5$)$_3$ | —OH, vinyl group | — |
| Methacryloxypropyltriethoxysilane | TESPM | | —OH, methacryloxy group | — |
| Silica Nanoparticles (e.g. Ludox ® or Nyacol ®) | | SiO$_2$ | —OH | — |
| Sodium Silicate (e.g., 27% Silicic Acid 10% NaOH | Water Glass | | —OH | — |
| Diglycerylsilane | DGS | | —OH | — |
| Structure Modifiers | | | | |
| Methyltriethoxysilane | MTMOS | CH$_3$Si(OCH$_3$)$_3$ | —OH | —CH3 |
| Trimethylmethoxysilane | TMMS | CH$_3$OSi(CH$_3$)$_3$ | —OH | —CH3 |
| Ethyltriethoxysilane | TEES | C$_2$H$_5$Si(OC$_2$H$_5$)$_3$ | —OH | —C2H5 |
| n-propyltriethoxysilane | TEPS | C$_2$H$_5$O)$_3$SiCH$_2$CH$_2$CH$_3$ | —OH | —C3H7 |
| n-butyltriethoxysilane | TEBS | C$_{10}$H$_{24}$O$_3$Si | —OH | —C4H9 |
| 3-aminopropyltriethoxysilane | APTS | H$_2$N(CH$_2$)$_3$Si(OC$_2$H$_5$)$_3$ | —OH, NH2 | |
| 3-(2,4-Dinitrophenylamino)propyl-triethoxysilane | | | —OH, Dinitropropylamino | |

TABLE 1-continued

Examples of Typical Inorganic Precursors

| Chemical Name | Acronym | Molecular Formula | Reactive Groups | Non-reactive group |
|---|---|---|---|---|
| Mercaptopropyltriethoxysilane | TEPMS | $HS(CH_2)_3Si(OCH_2CH_3)_3$ | —OH, Thiol | |
| 3-(2-Aminoethylamino)propyl-triethoxysilane | | $(CH_3O)_3Si(CH_2)_3NHCH_2CH_2NH_2$ | —OH, NH2 | |
| Isocyanatopropyltriethoxysilane | | $C_{10}H_{21}NO_4Si$ | —OH, Isocyanato | |
| Hydroxyl-terminated polydimethylsiloxane | PDMS | | —OH | —CH3 |
| triethoxysilyl-termonated polydimethylsiloxane | PDMS | | —OH | —CH3 |
| Methyltriethoxysilane | MTES | $CH_3Si(OC_2H_5)_3$ | —OH | —C2H5 |
| Triethoxysilyl-terminated poly(oxypropylene) | | | —OH | |

Generally, confinement of biomaterials can be carried out using variations of the hydrolysis and the alkali metal silicate methods of generating a reactive silicon compound. For the hydrolysis route, after the hydrolysis step of the alkoxide is completed, the method can include at least partial removal of the byproduct alcohol. In such a method, an alkoxide (TEOS or TMOS) is hydrolyzed first in the presence of water and HCl. A typical mixture of 1 mL of TEOS, 1 mL of water and 0.001M HCl is sonicated for 10 to 15 min to ensure uniform mixture. The resultant product can be at low acidic pH (~2), which can maximize the rate of hydrolysis while limiting condensation. Next, evaporation of the alcohol is achieved by any suitable means, for example rotoevaporation for 10 min. The mixture may then be tested with chromic acid to ensure the absence of alcohol. Next, a microorganism solution can be added and mixed, wherein the mixing can occur by any suitable means, for example by vortexing. Prior to addition, the microorganism solutions can be prepared in a potassium buffer or water at about neutral pH. The gelation process can take place within few minutes. Studies of E. coli encapsulated using this method show that cells can both survive the confinement process and remain metabolically active, see Examples. A variation of this protocol can be used that includes coating living microorganisms with at least one layer of $SiO_2$ produced by treatment with flux of gaseous silicon alkoxides. The at least one layer of $SiO_2$ can reduce exposure to alcohol and other by-products.

Another protocol includes the use of a colloidal silica. In this method silica gels can be prepared by mixing sodium silicate (27 w % $SiO_2$, 10 w % NaOH) with colloidal silica nanoparticles (e.g. 12 nm diameter). Acid is added to the mixture to form the reactive silicon compounds, e.g. silanols. The mixture is homogenized by stirring by any suitable means and mixed with a microorganism suspension. Gelation can occur within few minutes at room temperature. The colloidal silica route is preferred for the confinement of microorganisms since better viability and metabolic activity of confined prokaryotic can be are obtained. The aqueous route has potential for eukaryotic cells, which can remain viable for 1 to 2 days after confinement in silica nanoparticles.

Encapsulation of Microorganisms

Traditional encapsulation techniques of microorganisms suffer problems and difficulties. For example, in some encapsulation techniques, the microorganisms do not survive. In some encapsulation techniques, the activity the microorganism had prior to encapsulation is not preserved once the microorganism is encapsulated.

The present invention avoids some problems encountered in traditional encapsulation techniques of cells. The present invention uses sol-gel technology for the immobilization of E. coli cells that express the gene encoding a particular protein. In one example, the gene is the atzA gene which encodes for the atrazine-degrading enzyme atrazine chlorohydrolase. After encapsulation the cells are still metabolically active and can still express the AtzA protein for the conversion of atrazine into hydroxyatrazine. The present invention includes hybrid silicon oxide materials from a combination of reactive silicon compounds (formed from a variety of precursors) and organic polymers that can produce a nanoporous or macroporous material for the immobilization of the cells. The protocol developed is biocompatible and the cells show good tolerance (cells have metabolic activity and enzymatic activity after encapsulation) to the byproducts produced during the gel synthesis.

The present invention provides surprising new and significant characteristics. Additionally, silica nanoparticles themselves can be used as an encapsulation agent, allowing the use of a completely biocompatible coalescence mechanism of gel formation. The composition and method has substantial flexibility in terms of properties of the encapsulated biomaterial including the mechanical properties, surface chemistry, and porosity, and the present method can provide facile scale up. The present invention can provide a method of atrazine remediation that encompasses the use of genetically engineered cells with a mild synthesis of a nanoporous or macroporous hybrid silicon oxide material. The present invention can produce a remarkable rate of conversion of atrazine into hydroxyatrazine when atrazine chlorohydrolase-expressing cells are encapsulated in the gel (nanoporous case), see Examples.

Figure 1B:
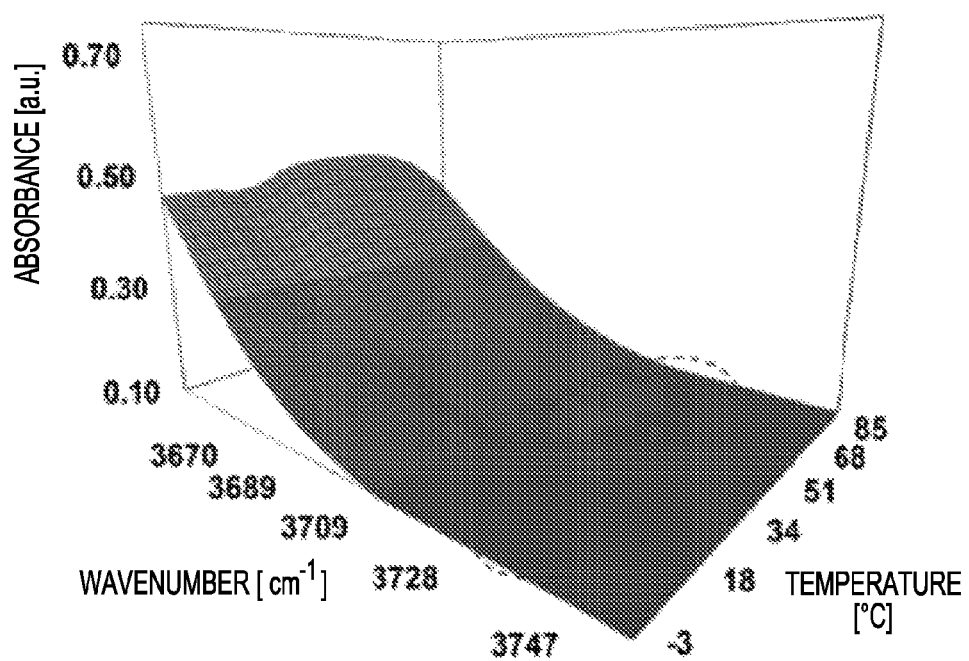
FIG. 1B illustrates the lack of silanol (—SiOH) groups on the surface of the matrix due to the presence of trehalose, in accord with certain embodiments.
Figure 1C:
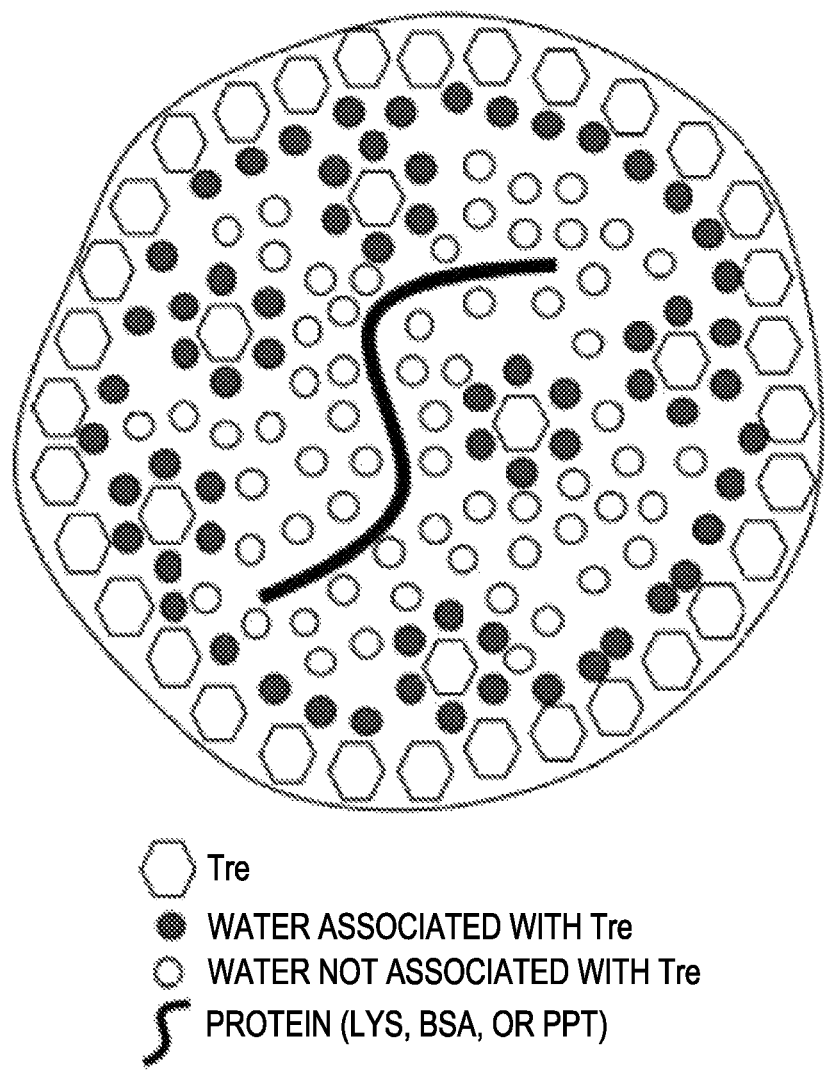
FIG. 1C illustrates a proposed interaction between the silica-matrix and trehalose, in accord with certain embodiments.

The present invention can include the use of silica nanoparticles at different concentrations. This allows destabilization and gelation of the colloidal suspension of silica nanoparticles by changing the pH to a neutral or close to neutral value. Gelation can also be inducing by dialyzing first the colloidal suspension against water for at least 24 h. In dialyzing, the colloidal suspension is held on one side of a membrane and water is held on the other, changing the pH of the colloidal suspension. Then, trehalose in powder form can be dissolved in the colloidal suspension in concentrations of, in some examples, up to 0.5 M. The use of trehalose can reduce the concentration of silanol moieties at the surface of the silica-matrix, as shown in FIGS. 1A and 1B, which can modify interactions between the silica-matrix and the organism, as shown in FIG. 1C. After stirring for 5 minutes in a vortex machine, or until the sample becomes a transparent and uniform mixture, the microorganism solution can then be added and mixed. This mixing can be performed by any suitable means, for example in a vortex machine. Gelation can take place immediately and the samples can then be left to age for 24 hrs at different relative humidity conditions (while the temperature is kept constant). The preparation and analysis of samples prepared in this fashion are included the Example section.

Figure 2:
FIG. 2 illustrates an overview of the microorganism encapsulation composition and method in one embodiment of the present invention.

For the encapsulation of cells the present invention provides compositions and techniques that allow the incorporation of cells in either mesoporous or macroporous hybrid silica matrices. FIG. 2 is an overview of the process of encapsulation. In general, it starts with a source of reactive silicon compound (for example, the "inorganic precursors" given in Table 1) that are hydrolyzed in an acid solution (e.g. acetic acid or HCl) to give a reactive silicon compound, e.g. silanols. Then the organic component (for example, see "organic precursors" given in Table 2, below) is added is added and mixed until a homogeneous mixture is obtained. In one example, PEG 600 Da can be used for a nanoporous material and PEG 10 kDa can be used for a macroporous material. Finally cells are added and gently mixed with mild stirring or pipetting. The gel will form between minutes to hours depending on the composition initially chosen.

TABLE 2

Examples of Typical Organic Precursors

| Chemical Name | Acronym | Type of Interaction with Silica | Origin |
| --- | --- | --- | --- |
| Polyethylene glycol | PEG | HB | Synthetic |
| Polyvinyl alcohol | PVA | HB | Synthetic |
| Polyacrylicacid | HPAA | Electrostatic | Synthetic |
| Polymethyl methacrylate | PMMA | HB | Synthetic |
| PHEMA | PHEMA | HB | Synthetic |
| Pluronic F127, P123 | PEO-PE-PEO | HB | Synthetic |
| Aminoacids | A, G, Y, ... | HB, electrostatic | Synthetic |
| Peptide sequences | — | HB, electrostatic | Synthetic |
| Mono peptide sequences | — | HB, electrostatic | Synthetic |
| Alginate | — | HB, electrostatic | Natural |
| Gelatin | — | HB, electrostatic | Natural |
| Chitosan | — | HB, electrostatic | Natural |
| Sucrose | — | HB | Natural |
| Trehalose | — | HB | Natural |
| Dextran | — | HB | Natural |
| Casein | — | HB, electrostatic | Natural |
| Bovine serum | — | HB, electrostatic | Natural |
| Collagen | — | HB, electrostatic | Natural |

In various embodiments, long- or medium-term viability of the encapsulated biomaterial can occur, such that significant population of biomaterial survives and/or remains metabolically active for greater than about 1 week, 2 weeks, 3 weeks, 4 weeks, 2 months, 3 months, 4 months, 8 months, or about 1 year or more. In other embodiments, long- or medium-term viability of the encapsulated biomaterial does not occur, such that the majority of biomaterial is dead within less than about 1 week, 6 days, 5 days, 4 days, 3 days, 2 days, or in less than about 1 day. In some embodiments, such as in some embodiments involving atrazine remediation, long- or medium-term viability of the encapsulated biomaterial in not needed to achieve the desired effect, due to for example retained catalytic activity of the materials produced by the biomaterial after the biomaterial has ceased to live. In other embodiments, keeping the biomaterial alive can be important for achieving the desired effect, for example when the biomaterial loses the valuable property once it has died or soon thereafter.

In some embodiments, the encapsulation of the biomaterial can advantageously guard the biomaterial from predation. In some embodiments, the encapsulation of the biomaterial can advantageously cause the biomaterial to be less susceptible to temperature fluctuations, pH changes, or changes in salinity as compared to the respective unencapsulated biomaterial.

Nanoporous and Macroporous Silica-Matrix Synthesis

The compositions and methods of the present invention for forming a nanoporous or macroporous silica-matrix can be chosen to maximize the viability and metabolic activity of cells encapsulated by the matrix. Viable and active cells after encapsulation can allow using the cells as metabolic factories for cell-based biochemistry processes such as: biosensing, biocatalysis, bioreactive coatings, and the like.

Compositions and methods for forming nanoporous silica-matrixes include all compositions and methods for forming silica-matrix encapsulated biomaterials described herein, as well as the specific procedure described here. For formation of nanoporous silica-matrixes, a step can include treating a silicate-containing solution with acid to create a reactive silicon compound (e.g. silanols). As described above, condensation of silicate-containing colloidal suspensions of silica nanoparticles (between 10% to 50% wt %) can occur by acidification (to give e.g. silanols). A strong acid can be preferable (e.g., HCl), which can reduce the amount of acid needed, and avoids changing the molar ratios between silica and water. After formation of the reactive silicon compound via acidification of silicates, a highly reactive (e.g. silanol-containing) hydrolyzed silane solution can be added to facilitate crosslinking or to allow surface chemistry modification (see Table 1 for list of silane precursors, "inorganic precursors"). The ratios of colloidal nanoparticles and silane crosslinking agents can be chosen according to the mechanical, chemical, or optical properties desired. The next step can include the addition of an organic precursor, such as those shown in Table 2. The organic precursor can be a synthetic polymer, natural polymer or monomer, or amino acid. The concentrations of incorporation can be in mass or volume ratios with respect to the silica content and may vary from 1% up to 50% in mass or volume. By incorporating the organic component, the following are examples of the effects can occur: (1) reduction of the silica surface (e.g. SiOH) interactions with cell membranes, which interactions can be detrimental to the preservation of valuable activity of the biomaterial for long-term encapsulation, (2) post-gelation surface modification can occur with organic or inorganic chemistry conjugation techniques (e.g. modification or addition of the functional groups at the surface), (3) reduction of shrinkage during aging of the gel, and (4) increased mesoporosity of the gel. Before or after incorporation of the organic component, the microorganism can be incorporated into the mixture. Cells can be suspended in their own media, salt solutions or in water. The cell solution of choice it is only limited to the cell type (e.g. bacterial, yeast). At this step the final pH needs to checked and in some cases may need to be adjusted with a strong base (e.g. sodium hydroxide). Gelation will take place in few minutes to hours depending on the compositions and precursors chosen.

Compositions and methods for forming macroporous silica-matrixes include all compositions and methods for forming silica-matrix encapsulated biomaterials described herein, as well as the specific procedure described here. For formation of macroporous silica-matrixes, the method can include inducing a controlled phase separation along with the sol-gel transition of the solution components. In general, a hydrophilic organic polymer can be mixed in water under acidic conditions (e.g. polyethylene glycol, polyvinyl alcohol, polyacrylic acid). The acid concentration can be chosen from about $10^{-3}$ M to about 1 M (e.g. 0.01 M, e.g. acetic acid, HCl, HNO$_3$) to favor the hydrolysis or condensation process when the silica precursor is added. After a clear transparent mixture is obtained the remaining part of the process can be carried out at any suitable temperature, for example about 0° C. The silica precursor can be added after the removal of the byproduct of hydrolysis when required (e.g. for TMOS or TEOS a rotating evaporator ("rotovap") was used); otherwise; the silica precursor can be added to the acidic polymeric solution (e.g., THEOS, sodium silicate, silica nanoparticles). At this step the pH can be raised to a suitable value, for example a pH of 6. Prior to the addition of the cells (e.g. *E. coli*), polymeric polyelectrolytes (e.g. chitosan, alginate) can be attached to the cell's membrane. Four to six layers of polymers can be deposited. The final layer of the polyelectrolyte was negative. Then, the coated cells can be added to the solution previously described at 0° C. In the final step, the working solution can be deposited on the desired molds and cast at various temperatures, for example, room temperature or a lower temperature, 30° C., 37° C., 40° C., 45° C., or a higher temperature. The temperature used can depend on the type of structure desired and also can depend on the type of microorganism used. The gelling and aging times for the material can be any suitable time, for example, 4, 6, 12, 18, and 24 hours. Aging can be conducted while the material is wet or dry, e.g. hydrated or dehydrated. After the aging step the gels can be rehydrated and stored at any temperature, including, for example, 4° C., or room temperature.

Modification of the Properties of the Silica-Matrix Encapsulated Biomaterial

The use of hybrid materials (silicon oxide plus organic polymers or monomers) can cause a synergistic interaction of the organic and inorganic groups of the component materials that can provide a diverse set of materials with novel properties. Mechanical, optical, and chemical properties of the resulting silica-matrix encapsulated biomaterials can be tailored. Porosity, mechanical, optical, and surface chemistry properties can be modified in a versatile and facile manner that allow the creation of functional biohybrid materials.

For example, in applications where high rates of diffusion through the material are required (e.g. biocatalysis, bioremediation) the porosity of the silica gel matrix can be a key issue to help ensure high rates of biochemical conversion or purification. In the nanoporous gel when an organic polymer or monomer is included during synthesis the mesoporosity of the material can be increased. In addition, added organic polymers or monomers can interact with the surface silanol or siloxane silica groups, which can reduce the possibilities of damaging the structure and functionality of the biomaterials. The incorporation of these groups can occur after an alkoxysilane hydrolysis step, which can provide a uniform mixture of the organic compound through the silica material. Polyethylene glycol or disaccharides can be used increase the mesoporosity, as shown in the Examples.

The Examples also show methods of modification of the mechanical and surface chemistry properties.

Treatment of Water

The encapsulated biomaterial of the present invention can be used for treatment of water, wherein the biomaterial can transform one or more chemicals in the water into other chemicals, such as chemicals that are less toxic. Any suitable biomaterial that is encapsulated can be used to treat water. A specific example includes the treatment of atrazine-containing water, to covert at least some of the atrazine therein to a different chemical. Another specific example includes the treatment of water that contains pesticides, herbicides, fungicides, insecticides, or other pollutants, for example pollutants from industrial processes or oil and gas drilling processes.

In various embodiments, the present invention provides an encapsulated biomaterial, wherein the biomaterial can degrade chemicals that can be present in fracking water. In various methods, the present invention provides a method of degrading chemicals in fracking water, for example to decontaminate the water or to make the water less toxic. Hydraulic fracturing is a process used to recover natural gas from deep shale formations. Large amounts of water, sand and additives are pumped under high pressure to create fractures, which allow the gas to travel to the surface for collection. Fracking creates jobs, stimulates the economy and decreases foreign fuel dependency. While fracking increases access to natural gas in shale formations, water pollution is a concern. Millions of gallons of water containing numerous additives are used to hydraulically fracture each well. Poorly constructed transportation pipelines and overflow of evaporation pools due to rainfall contaminate ground water.

Hydraulic fracturing fluid contains many materials, including for example acids, biocides, breakers, clay stabilizers, corrosion inhibitors, crosslinkers, defoamers, foamers, friction reducers, gellants, pH control, proppants, scale control and surfactants. Table 3 below lists examples of toxic chemicals used in hydraulic fracturing. In the Table, a carcinogen designated as agent or substance that can cause cancer, RC indicates a chemical regulated by the EPA via the Safe Drinking Water Act (SDWA), and HAP designates a hazardous air pollutant.

TABLE 3

Toxic chemicals found in hydraulic fracturing.

| Chemical Name | Chemical Category |
| --- | --- |
| Methanol (Methyl alcohol) | HAP |
| Ethylene glycol (1,2-ethanediol) | HAP |
| Diesel | Carcinogen, RC, HAP |
| Naphthalene | Carcinogen, HAP |
| Xylene | RC, HAP |
| Hydrogen chloride (Hydrochloric acid) | HAP |
| Toluene | RC, HAP |
| Ethylbenzene | RC, HAP |
| Diethanolamine (2,2-iminodiethanol) | HAP |
| Formaldehyde | Carcinogen, HAP |
| Sulfuric acid | Carcinogen |
| Thiourea | Carcinogen |
| Benzyl chloride | Carcinogen, HAP |
| Cumene | HAP |
| Nitrilotriacetic acid | Carcinogen |
| Dimethyl formamide | HAP |
| Phenol | HAP |
| Benzene | Carcinogen, RC, HAP |
| Di (2-ethylhexyl) phthalate | Carcinogen, RC, HAP |
| Acrylamide | Carcinogen, RC, HAP |
| Hydrogen fluoride (Hydrofluoric acid) | HAP |
| Phthalic anhydride | HAP |
| Acetaldehyde | Carcinogen, HAP |
| Acetophenone | HAP |
| Copper | RC |

TABLE 3-continued

Toxic chemicals found in hydraulic fracturing.

| Chemical Name | Chemical Category |
|---|---|
| Ethylene oxide | Carcinogen, HAP |
| Lead | Carcinogen, RC, HAP |
| Propylene oxide | Carcinogen, HAP |
| p-Xylene | HAP |

Chemical components of hydraulic fracturing can include chemicals selected from, for example, benzene, toluene, 1-fluoro-4-iodobenzene, 1-bromo-4-iodobenzene, 1-bromo-2,3-difluorobenzene, 1,3-dibromobenzene, benzonitrile, propoxybenzene, 4-fluorotoluene, 4-chlorotoluene, 2-iodotoluene, 4-iodotoluene, 3-bromotrifluoromethyltoluene, (2-bromoethyl)benzene, (2-azidoethyl)benzene, phenethyl alcohol, (2-cyanoethyl)benzene, (2-thiocyaniethyl)benzene, (2-acetoxyethyl)benzene, 2-(2-bromoethyl)bromobenzene, 2-chlorostyrene, 3-chloro styrene, 4-chloro styrene, 2-bromostyrene, ethynylbenzene, 1,3-dimethylbenzene, 1,4-dimethylbenzene, ethylbenzene, phenylethanol, acetophenone, trifluorotoluene, trifluoromethoxybenzene, anisole, styrene, trans-β-bromostyrene, cis-β-bromostyrene, trans-cinnamonitrile, 1,2-dichlorobenzene, 1,3-dichlorobenzene, 1,4-dichlorobenzene, 4-bromotoluene, fluorobenzene, 2-methylphenol, 3-methylphenol, 4-methylphenol, methyl p-tolyl sulfide, 2-nitrotoluene, 3-nitrotoluene, 4-nitroluene, ethyl phenyl sulfide, p-methoxyphenyl sulfide, methyl p-nitrophenyl sulfide, methyl phenyl sulfide, 2-methoxynaphthalene, biphenyl, 2-methoxybiphenyl, 2,3-dimethoxybiphenyl, 1,2-methylenedioxybiphenyl, 2-chlorobiphenyl, 3-chlorobiphenyl, 4-chlorobiphenyl, cis-1-chloro-1-propene, trans-1-chloro-1-propene, cis-1-bromo-1-propene, trans-1-bromo-1-propene, cis-2-chloro-2-butene, trans-2-chloro-2-propene, 1-chloro-2-methylpropene, 1,1-dichloro-1-propene, trichloroethylene, cis-1,4-dichloro-2-butene, trans-1,4-dichloro-2-butene, 1,1-dichloroethene, cis-1,2-dichloroethene, trans-1,2-dichloroethene, cis-1,2-dibromoethene, trans-1,2-dibromoethene, 3,4-dichloro-1-butene, indane, indene, indole, 1,2-dihydroxynaphthalene, benzocyclohept-1-ene, phenetole, chlorobenzene, bromobenzene, phenanthrene, fluorine, naphthalene, 2-naphthoic acid, 2,6-dimethylnaphthalene, 2,3-dimethylnaphthalene, 1-methylnaphthalene, 2-nitronapthalene, 2-hydroxymethylnaphthalene, 6-amino-2-naphthalenesulfonic acid, 5-fluoroindole, 5-methoxyindole, 5-nitroindole, 6-fluoroindole, 1-indanone, 2-indanone, 1-indenol, 1-indanol, 1,2,4-trimethylbenzene, 3-methylbenzothiophene, carbazole, 1,2-dihydronaphthalene, indoline, phenetole, N-methylindole, N-methylaniline, N,N-dimethylaniline, ethylphenyl sulfide, p-methoxyphenyl methyl sulfide, methyl p-nitrophenyl sulfide, 2-methylbenzo-1,3-dithiole, 3-methylbenzothiophene, dibenzthiophene, monohydroxy-fluoranthene, cis-1,2-fluoranthene dihydrodiol, 1,2-dihydroxy-fluoranthene, 1,2-dimethoxy-fluoranthene, 9-fluorenol-1-carboxy-3-propenyl-2-one, 9-fluorene-1-(carboxy-2-hydroxy-1-propenol), 9-fluorenol-1-carboxylic acid, 9-fluorenone-1-carboxylic acid, 9-fluorenol, 9-fluorenone, 1,9a-dihydroxy-8,8a,9,9a-tetrahydro-1H-fluorene-9-one, 6-hydroxy-8-oxatricyclotetradeca-1(14),2,4,12-tetraen-9-one, 2',3'-dihydroxy-biphenyl-2-carboxylic acid, 2-[(2Z,4E)-5-carboxy-5-hydroxypenta-2,4-dienoyl]benzoic acid, cis-1,9a-dihydroxy-1-hydro-1-fluorene-9-one-8-carboxylic acid, 2',3'-dihydroxybiphenyl-2,3-dicarboxylic acid, 9-hydroxy-3,4-benzocoumarin-1-carboxylic acid, 3-[(2Z,4E)-5-carboxy-5-hydroxypenta-2,4-dienoyl]benzene-1,2-dicarboxylic acid, 1,2,3-benzene tricarboxylic acid, phthalate, cis-2,3-fluoranthene dihydrodiol, 2,3-dihydroxy-fluoranthene, 2,3-dimethoxy-fluoranthene, 9-carboxymethylene-9H-fluorene-1-carboxylic acid, cis-7,8-fluoranthene dihydrodiol, 7,8-dihydroxy-fluoranthene, 2-hydroxy-4-(2-oxo-acenaphthylen-1(2H)-ylidene)but-2-enoic acid, 7,8-dimethoxy-fluoranthene, 2-(hydroxymethyl)-2H-acenaphthylen-1-one, 2-oxo-acenaphthene-carboxylic acid, acenaphthylene-1(2H)-one, 1H,3H-benzo[de]isochromen-1-one, 2-hydroxy-1,2-dihydroacenaphthylene-1-one, naphthalene-1,8-dicarboylic acid, 2-[(1Z)-2-carboxyeth-1-en-1-yl]acenaphthylene-1-carboxylic acid, 2-(hydroxymethyl)acenaphthylene-1-carboxylic acid, 2-(methoxymethyl)acenaphthylene-1-carboxylic acid, 2-formylacenaphthylene-1-carboxylic acid, acenaphthylene, acenaphthylene-1-ol, 1,2-dihydroacenaphthylene-1,2-diol, 1,2-dihydroxy-acenaphthylene, acenaphthoquinone, 1,8-naphthalic anhydride, cis-8,9-fluoranthene dihydrodiol, 8,9-dihydroxy-fluoranthene, 8,9-dimethoxy-fluoranthene, acenaphthene, 1,2-dihydroacenaphthylen-1-ol, 1,2,4,5-tetrahydroacenaphthylene-4,5-diol, 1,2-dihydroacenaphthylene-4,5-diol, 4,5-dihydroacenaphthylene-4,5-dione, 4,5-dihydroacenaphthylene-4,5-diol, 1,2,4,5-tetrahydroacenaphthylene-4,5-dione, acenaphthylene-4,5-diol, pyrene, 4,5-dihydropyrene-4,5-diol, pyrene-4,5-diol, pyrene-4,5-oxide, trans-4,5-dihydroxy-4,5-dihydropyrene, pyrene-1,2-oxide, trans-1,2-dihydroxy-1,2-dihydropyrene, pyrene-4,5-dione, 1,2-dihydropyrene-1,2-diol, pyrene-1,2-diol, 2-methoxy-1-hydropyrene, 1-methoxy-2-hydropyrene, 1,2-methoxypyrene, phenanthrene-4,5-dicarboxylic acid, phenanthrene-4-carboxylic acid, methyl phenanthrene-4-carboxylate, 5-hydroxyphenanthrene-4-carboxylic acid, 4-oxa-pyren-5-one, 3,4-dihydroxy-3H-phenanthrene-4-carboxylic acid, phenanthrene-3,4-diol, (3Z)-4-(1-hydroxynaphthalen-2-yl)-2-oxobut-3-enoic acid, 1-hydroxynaphthalene-2-carbaldehyde, 1-hydroxynaphthalene-2-carboxylic acid, phenanthrene-1,2-dihydrodiol, phenanthrene-1,2-diol, 2-methoxy-1-hydroxyphenanthrene, 1-methoxy-2-hydroxyphenanthrene, 1,2-dimethoxyphenanthrene, 3,4-dihydrophenanthrene-3,4-diol, phenanthrene-9,10-dihydrodiol, phenanthrene-9,10-diol, 2-(2-carboxyphenyl)benzoic acid, 2-[(1Z)-3-carboxy-3-oxoprop-1-en-1-yl]naphthalene-1-carboxylic acid, naphthalene-1,2-dicarboxylic acid, benzo[h]chromen-2-one, 5,9,10-trihydroxy-9,10-dihydrophenanthrene-4-carboxylic acid, 5,9,10-trihydroxyphenanthrene-4-carboxylic acid, 2-(2-carboxy-6-hydroxyphenyl)benzene-1,3-dicarboxylic acid, 2-(2-carboxyphenyl)-3-hydroxybenzoic acid, 2-(2-carboxy-6-hydroxyphenyl)-3-hydroxybenzoic acid, naphthalen-1-ol, 2-[(1Z)-3-carboxy-3-oxoprop-1-en-1-yl]benzoic acid, 2-(hydroxymethyl)benzoic acid, benz[a]anthracene, benz[a]anthracene-cis-1,2-dihydrodiol, 1,2-dihydroxybenz[a]anthracene, (3Z)-4-(1-hydroxyanthracen-2-yl)-2-oxobut-3-enoic acid, benz[a]anthracene-7,12-dione, 1-[(2-hydroxyphenyl)carbonyl]naphthalene-2-carboxylic acid, 1-benzoylnaphthalene-2-carboxylic acid, benz[a]anthracene-cis-5,6-dihydrodiol, 5,6-dihydroxybenz[a]anthracene, 3-(2-carboxyphenyl)naphthalene-2-carboxylic acid, 5,6-dimethoxybenz[a]anthracene, benz[a]anthracene-cis-10,11-dihydrodiol, 10,11-dihydroxybenz[a]anthracene, 10-hydroxy-11-methoxybenz[a]anthracene, 1,2-dimethoxybenz[a]anthracene, 2-oxo-3-[(2Z)-3-oxophenanthren-2-ylidene]propanoic acid, 3-[(2Z)-3-hydroxy-3H-phenanthren-2-ylidene]-2-oxopropanoic acid, anthracene, anthracene cis-1,2-dihydrodiol, 1,2-dihydroxyanthracene, 1-methoxy-2-hydroxyanthracene, 9,10-anthraquinone, 3-[(1Z)-2-carboxyeth-1-en-1-yl]naphthalene-2-carboxylic acid, (3Z)-

4-(3-hydroxynaphthalen-2-yl)-2-oxobut-3-enoic acid, 3-hydroxynaphthalene-2-carboxylic acid, 2,3-dihydroxynaphthalene, benzo[g]chromen-2-one, naphthalene cis-1,2-dihydrodiol, 1,2-dihydroxynaphthalene, naphthalene-1,2-dione, 2-[(1Z)-2-carboxyeth-1-en-1-yl]benzoic acid, 2-formylbenzoic acid, naphthalene-1,2-epoxide, naphthalene trans-1,2-dihydrodiol, cis-o-hydroxybenzlpyruvate, 2-hydroxybenzaldehyde, salicylate, catechol, glutaraldehyde, acrylamide, acrylonitrile, acrylic acid, biphenyl-cis-2,3-dihydrodiol, 2,3-dihydroxybiphenyl, 2-hydroxy-6-keto-6-phenylhexa-2,4-dienoic acid, benzoic acid, 4-hydroxybiphenyl, 4-hydroxybiphenyl-cis-2,3-dihydrodil, 3-(4-hydroxyphenyl)benzene-1,2-diol, (2E,4Z)-2-hydroxy-6-(4-hydroxyphenyl)-6-oxohexa-2,4-dienoic acid, 4-hydroxybenzoic acid, benzo[a]pyrene, benzo[a]pyrene cis-9,10-dihydrodiol, 9,10-dihydroxybenzo[α]pyrene, (3Z)-4-(1-hydroxypyren-2-yl)-2-oxobut-3-enoic acid, 10-oxabenzo[a]chrysen-9-one, 2-(hydroxymethyl)pyren-1-ol, 1-hydroxypyrene-2-carboxylic acid, benzo[a]pyrene cis-4,5-dihydrodiol, 4,5-dihydroxybenzo[a]pyrene, chrysene-4,5-dicarboxylic acid, chrysene-4-carboxylic acid, chrysene-5-carboxylic acid, benzo[a]pyrene cis-11,12-dihydrodiol, 11,12-dihydroxybenzo[a]pyrene, benzo[a]pyrene-11,12-epoxide, benzo[a]pyrene trans-11,12-dihydrodiol, hydroxymethoxybenzo[a]pyrene, demethoxybenzo[a]pyrene, phthalate-3,4-cis-dihydrodiol, 3,4-dihydroxyphthalate, protocatechuate, benzoate, 4-hydroxybenzoate, 4-hydroxyphthalate, beta-carboxy-cis,cis-muconate, gamma-carboxymucono-lactone, beta-ketoadipate enol-lactone, beta-ketoadipate, methane, ethane, propane, ethane, propene, butane, butane, methylcyclopropane, pentane, vinylidene chloride, 1,2-dichloroethane, 1,2,3-trichloropropane, chloroacetic acid, fluoroacetic acid, methanol, ethylene glycol, ethanol, 1,4-dimethylcyclohexane, 1,3-dimethylcyclohexane, methylene cyclohexane, heptanes, neopentane, 2-methylpropane, 2,3-dimethylpentane, adamantine, cyclopropylbenzene, coumarin, and acridine.

There are naturally occurring non-mammalian organisms capable of degrading chemicals that can occur in fracking water. By degrading the chemicals, the water can be made less toxic. Various examples of these organisms are given in Table 4 along with examples of the chemicals they can degrade.

TABLE 4

Microorganisms for the biodegradation of toxic compounds.

| Organism | Degrades |
|---|---|
| *Pseudomonas putida* F1 | Benzene, Toluene, ethylbenzene, p-cymene and 104 other chemicals |
| *Pseudomonas putida* NCIB 9816 | Naphthalene and 75 other chemical |
| *Mycobacterium flavescens* | Many high-molecular-weight polycyclic aromatic hydrocarbons (pyrene, phenanthrene, fluoranthene, |
| *Nocardia* JH7Y | Biphenyl, naphthalene |
| *Nocardia butanica* (*Rhodococcus rhodochrous*) ATCC 21197 | Trichloroethylene, vinyl chloride, dichloroethylene |
| *Burkholderia xenovorans* LB400 | Biphenyl, many polychlorinated biphenyls |
| *Burkholderia cepacia* G4 | Toluene, trichloroethylene |
| *Mycobacterium vanbaalenii* PYR-1 | Many high-molecular-weight polycyclic aromatic hydrocarbons (phenanthrene, anthracene, fluoranthene, pyrene, benzo[a]pyrene, benz[a]anthracene, and 7,12-dimethylbenz[a]anthracene) |
| *Deinococcus radiodurans* | Chromate, uranate, pertechnate |
| *Methylosinus trichosporium* OB3b | Methane, ethane, propane, ethene, propene, vinyl chloride, dichloroethene, trichloroethylene, methanol, formaldehyde, formic acid |
| *Methanobacterium* DM4 | Methanol, formaldehyde, formic acid, methylamine, dimethylamine, dichloromethane, dibromomethane. diiodomethane, chlorobromomethane, fluorochloromethane |
| *Methylomonas methanica* 68-1 | Methane, naphthalene, trichloroethylene |
| *Methylobacterium organophilum* xx | methanol |
| *Methylococcuus capsulatus* (Bath) | Methane, benzene, toluene, dimethyl ether, ethane, hexane |
| *Methylocystis* sp. *Parvis* | Methane |
| *Methylobacterium ethanolicum* | Methane |
| *Methylocella silvestris* BL2 | Methane, methanol |
| *Methylobacterium* sp. strain CRL26 | methane |
| *Pseudomonas butanovora* | Butane |
| *Pseudomonas chlororaphis* BA23 | Acrylonitrile, acrylamide, butyronitrile |
| *Pseudomonas* sp. ADP | Atrazine, simazine, terbuthylazine, hydroxyatrazine, N-isopropylammelide, N-ethylammelide |
| *Arthrobacter aurescens* TC1 | Atrazine, simazine, terbuthylazine, hydroxyatrazine, N-isopropylammelide, N-ethylammelide, ametryn, atratone, propetryn |
| *Agrobacterium* sp. J14A | Atrazine, simazine, terbuthylazine, hydroxyatrazine, N-isopropylammelide, N-ethylammelide |
| *Alcaligenes* sp. SG1 | Atrazine, simazine, terbuthylazine, hydroxyatrazine, N-isopropylammelide, N-ethylammelide |

TABLE 4-continued

Microorganisms for the biodegradation of toxic compounds.

| Organism | Degrades |
|---|---|
| *Rhodococcus rhodochrous* J1 | Benzonitrile |
| *Rhodococcus* sp. strain WU-0103 | Benzthiophene |
| *Rhodococcus* sp IGTS8 | Benzyl sulfide |
| *Pseudomonas putida* | Caffeine, theobromine, paraxanthine, 7-methylxanthine, xanthine, 3,7-dimethyl uric acid |
| *Pseudomonas aeruginosa* | Caprolactam |
| *Pseudomonas* sp. C4 | Carbaryl, 1-naphthol |
| *Pseudomonas* sp. CA10 | Carbazole |
| *Pseudomonas stutzeri* OM1 | Carbazole |
| *Sphingomonas* sp. CB3 | Carbazole |
| *Novosphingobium* sp. FND-3 | Carbofuran |
| *Burkholdera cepacia* CAA2 | 3-Chloroacrylic acid |
| *Pseudomonas* sp. JS150 | Chlorobenzene |
| *Pseudomonas pseudoalcaligenes* KF707 | 4-Chlorobiphenyl |
| *Pseudomonas alcaligenes* NCIB9867 | m-Cresol |
| *Pseudomonas putida* N19-2 | N-Cyclohexylisocyanide |
| *Pseudomonas* sp. | Cyclohexylsulfamate |
| *Sphingomonas* sp. RW1 | Dibenzo-p-dioxin |
| *Rhodococcus* sp IGTS8 | Dibenzothiophene |
| *Xanthobacter autotrophicus* GJ10 | 1,2-Dichloroethane, 1,2-dibromoethane, chloroacetic acid, bromoacetic acid |
| *Alcaligenes eutrophus* | 2,4-Dichlorophenoxyacetic acid |
| *Arthrobacter* strains AD2 | 1,2,3-Trichloropropane, 1,3Dichloro-2-propanol, epichlorohydrin |
| *Nitrosomonas europea* | Dimethyl ether, diethyl ether, butylmethyl ether, butylethyl ether |
| *Pseudonocardia dioanivorans* CB1190 | 1,4-Dioxane |
| *Pseudomonas oleovorans* | Dodecyl sulfate |
| *Pseudomonas putida* Fu1 | Furfural |
| *Agrobacterium* sp 35S | 4-Hydroxypyridine |
| *Mycobacterium austroafricanum* IFP 2173 | Isooctane |
| *Arthrobacter* sp. | Malathion |
| *Mycobacterium vaccae* JOB5 | Methyl tert-butyl ether |
| *Mycobacterium austroafricanum* IFP 2012 | Methyl tert-butyl ether |
| *Pseudomonas* sp. C22 | Naphthtalene-1sulfonate |
| *Chelatobacter heintzii* ATCC 29600 | Nitrilotriacetic acid |
| *Pseudomonas putida* II-B | Nitroglycerin |
| *Pseudomonas* sp NK87 | Nylon |
| *Pseudomonas alcaligenes* | N-oleoyl-N-methyltaurine |
| *Flavobacterium* sp ATCC 39723 | Pentachlorophenol, 2,3,4,5-Tetrachlorophenol |
| *Dechlorosoma suillum* | Perchlorate, chlorate, chlorite, hypochlorite |
| *Nocardia simplex* FJ2-1A | 2,4,6-Trinitrophenol |
| Anaerobic consortium | Tetrabromobisphenol A |
| *Moorella thermoacetica* ATCC 39073 | Cyanuric acid |

The present invention provides a method of encapsulating biomaterials that can degrade chemical in fracking water within a silica-matrix. By encapsulating biomaterials that can degrade fracking-water chemicals, various embodiments of the present invention can provide a way of exposing fracking water to the organisms, allowing efficient degradation of the chemicals in the fracking water. In addition, the encapsulation of the biomaterials can, in some embodiments, provide protection from environmental stress, such as for example pH. Thus, the present invention provides a method of using the biomaterials encapsulated within the silica-matrix to degrade chemicals in fracking water. Various embodiments of the present invention can provide an efficient way to degrade chemicals in fracking water. Embodiments encompass any degree of chemical degradation of the fracking water. Thus, in some embodiments, only certain chemicals in the fracking water are degraded, while other chemicals are not degraded. In some embodiments, not all of a particular compound is degraded by the encapsulated biomaterial. For example, in certain embodiments about 0.01 wt % of a particular chemical can be degraded, or about 0.1 wt %, 1 wt %, 2 wt %, 5 wt %, 10 wt %, 20 wt %, 30 wt %, 40 wt %, 50 wt %, 60 wt %, 70 wt %, 80 wt %, 90 wt %, 95 wt %, 98 wt %, 99 wt %, 99.9 wt %, or about 99.99 wt % or more of the particular chemical can be degraded. In some embodiments, the chemical can be degraded to another chemical. The chemical product of the degradation can, in some embodiments, still be regarded as a toxic chemical. In other embodiments, the chemical product of the degradation is a non-toxic compound. Preferably, the chemical product of the degradation is less toxic than the chemical being degraded. Any suitable number of chemicals can be degraded by the process. In various embodiments, suitable combinations of any suitable number and amount of biomaterials can be encapsulated, together or separately, such that the desired type and amount of chemical degradation occurs as the fracking water is contacted with the encapsulated organisms.

In various embodiments, any of the compositions and methods described for atrazine removal can serve as suitable compositions and methods for degradation of chemicals in fracking water. In some embodiments, the compositions and methods that work best for treatment of fracking water can be different than optimal compositions and methods for atrazine degradation. For example, in various embodiments atrazine compositions can include TMOS with MTOS, whereas fracking compositions can include TMOS without MTOS. In some embodiments, the cells and silica nanoparticles for atrazine degradation can be diluted in water and stored in water, while in other embodiments, they can be diluted or stored in any suitable way, such as in a solvent other than water. In some examples, the cells and silica nanoparticles for fracking water treatment can be diluted or stored in organic solvent, while in other embodiments, they can be diluted or stored in any suitable way, such as in a solvent other than an organic solvent.

Mitigation of Gas Release

Various embodiments provide a silica-matrix encapsulated biomaterial wherein the biomaterial can consume low molecular weight gases, such as methane, ethane, propane, dimethyl ether, or a combination thereof. Various embodiments provide a method of encapsulating the biomaterial in a silica-matrix.

Methane is explosive and is a potent greenhouse gas. Thus, in situations where methane leakage is a problem, the biosilica can be used as a product to soak up methane (e.g. from air and/or water) and protect against explosions and atmospheric deposition. An example of a major market for use of this product would be in the gas industry where fracking is used to release natural gas, or methane, from shale. It is documented that leaks occur and that might lead to regulations given the concern over global warming. Moreover, companies have dealt with lawsuits from apparent leaks into water supplies and an explosion in Pennsylvania resulted in stiff fines.

Embodiments of the present invention that can consume gases can be used, for example, anywhere where natural gas leaks can occur. This can include, for example, home stoves and heaters, homeowner wells and faucets, bus fleets that run on methane, and in the oil and gas industry. The form of the encapsulated microorganism could be, for example, in the form of a mesh filter or packing around areas where leakage might occur. Another application could be in protecting against carbon monoxide poisoning from faulty heaters. At least 500 Americans die annually from this, many more worldwide and this could be prevented with an adequate system for degrading carbon monooxide where it might leak.

In some embodiments, the biomaterial can transform a flammable, explosive, or toxic gas into a gas that is non-flammable, nonexplosive, or nontoxic. In some embodiments, the gas can be transformed into a gas that is less flammable, less explosive, or less toxic than the starting material gas. In one example, the encapsulated biomaterial can oxidize methane gas to carbon dioxide gas.

Long-Term Catalytic Activity

In some embodiments, the encapsulated biomaterial can retain its catalytic activity for medium or long amounts of time, such as greater than about 1 week, 2 weeks, 3 weeks, 4 weeks, 2 months, 3 months, 4 months, 8 months, or about 1 year or more. In various embodiments, long- or medium-term viability of the encapsulated biomaterial can occur, such that significant population of biomaterial survives for greater than about 1 week, 2 weeks, 3 weeks, 4 weeks, 2 months, 3 months, 4 months, 8 months, or about 1 year or more. In some embodiments, the biomaterial remains viable (survives) in order to provide the continued activity. In some embodiments, the biomaterial can provide the continued activity without surviving. Such long term retention of catalytic activity can be highly advantageous over other methods of immobilization of biomaterials. In embodiments with non-living biomaterials retaining catalytic activity, this is contrasted with the common knowledge that bacteria that are not dividing and that are being stored at temperatures above freezing will lyse and their internal enzymes will inactivate due to proteolysis or inactivation. In embodiments with living biomaterials retaining catalytic activity, it is surprising that cells are able to survive within a silica-matrix for such long periods. The observation of very long-term stability is surprising and highly useful.

Long term retention of catalytic activity can be extremely valuable and advantageous. For example, in the case of biodegradation, the chemical being transformed is typically an organic molecule that has some toxic or other undesirable property. The enzyme-catalyzed reactions transform the chemical to either a less toxic, less flammable, or less explosive organic compound. In the case of a biotransformation, a chemical can be acted upon by the enzyme catalysts to make a more valuable, saleable chemical. In embodiments, the cost of the biotechnology is largely dependent on the cost of the catalyst, or enzyme. If the catalyst needs to be replaced frequently, the process cost will be higher. If the catalyst lifetime is long, the process can be less expensive and more practical to perform commercially. Thus, prolonging the duration of catalytic activity can be valuable to industry applications of encapsulated biomaterials involving biotransformation and biodegradation.

Various forms of the silica-matrix can be used to achieve medium- or long-term retention of catalytic activity. For example, the silica-matrix can be a bead, a fibrous network, a sheet or any other shape or form that meets the needs of the biodegradation task to be carried out. The inert material can impart stability to the bacterium and protection against predation, desiccation, pH, and temperature.

Various embodiments can be useful for cleaning up chemicals from spills, effluents from factories, processing facilities, or other situations where chemicals need to be removed or transformed. In other examples, embodiments can be in fermentors or bioreactors. Bioreactors are often run in batch mode and the cells or enzymes are replaced frequently. By using various embodiments, the lifetime of the catalyst can be increased and costs can be correspondingly decreased, opening new opportunities for biotechnology to be used in chemical manufacture Various processing methods can be used to impart long-term catalytic activity to the resulting encapsulated biomaterial. In some embodiments, cells can be stabilized using additives put into cell mixtures prior to encapsulation. In some embodiments, stabilization can be imparted by forming spherical biomaterials by dropping mixed cells and materials into mineral oil which causes the immediate formation of spherical structures. In some examples, the spherical structures can then be stored in mineral oil until needed. Alternatively, the genetics of the biomaterial can be modified to impart stability, for example by controlling the biosynthesis of osmotic protectants or quorum sensing agents.

Various processing methods can include variations of dropping the bio-silica material into a hydrophobic liquid via gravity. For example, two or more streams can be mixed from jets simultaneously. In some embodiments, more than two materials can be mixed simultaneously. In some embodiments, electrospinning can be used to make a bacterial-encapsulated silica mesh. Electrospinning can be used to conveniently generate a form useful for use as a filter, such as a mesh, including shapes that can be wrapped around a pipe or other potentially leaky device, for example for gas abatement applications.

EXAMPLES

The present invention can be better understood by reference to the following examples which are offered by way of illustration. The present invention is not limited to the examples given herein.

Example 1. Preparation of Nanoporous Silica-Matrix Encapsulated Biomaterials

The materials included 1 ml of TMOS (≥98%, from Fluka Analytical); 3 M Hydrochloric acid (28% to 30%, from Mallinckrodt); Silica nanoparticles (SNPs): 22 nm, or 85 nm (30% to 40%, from Sigma and Nyacol); Polyethylene glycol (PEG, Mw=600 Da, from Sigma); Bacterial solution: 400 μl. At a concentration of 0.1 g/ml; Distilled water.

First, TMOS was hydrolyzed with water in the presence of HCl (1/1/0.060 v/v/v) (for 1 ml of TMOS add 1 ml of water and 60 μl of 3M HCl). The hydrolysis process can be done using an ultrasonic or magnetic stirrer mixer. The byproduct of the hydrolysis can be removed using rotoevaporation or heating the mixture. Next, a water dilution of silica nanoparticles (SNPs) was prepared. For 22 nm SNPs, a dilution of 3.11 M can be prepared, for example. For 85 nm (SNPs) a dilution of 2.88 M can be prepared, for example. Next, 200 μl of hydrolyzed TMOS was mixed with 400 μl appropriate SNPs dilution, then add 100 μl of PEG was added. A silica-matrix can also be prepared without the addition of PEG. Next, 400 μl of cell solution is added by gently pipetting the mixture. Next, the mixture was transferred to the desired containers for casting the gel. Gelation took place in 5 to 10 min. The gel can be aged for 1 to 2 hr. Then, water can be added.

Figure 3A:
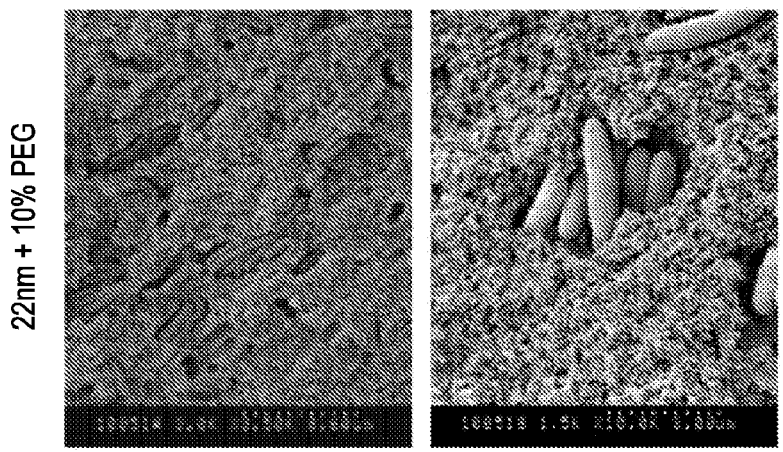
FIG. 3A-C illustrates nanoporous silica-matrix encapsulated bacteria of one embodiment of the present invention.
Figure 3B:
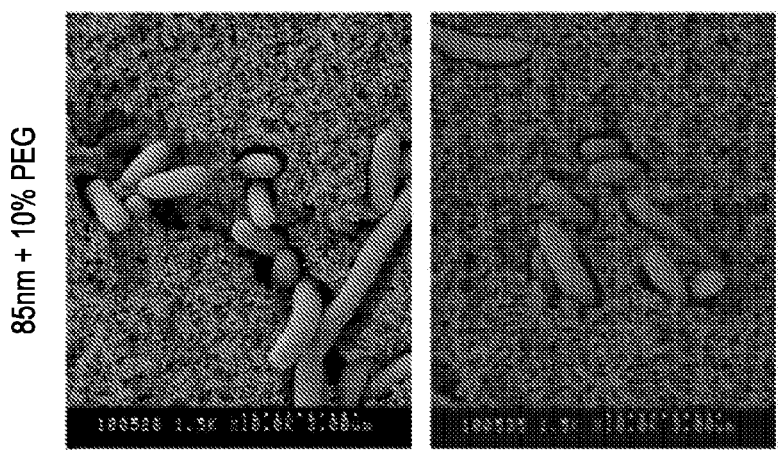
Figure 3C:
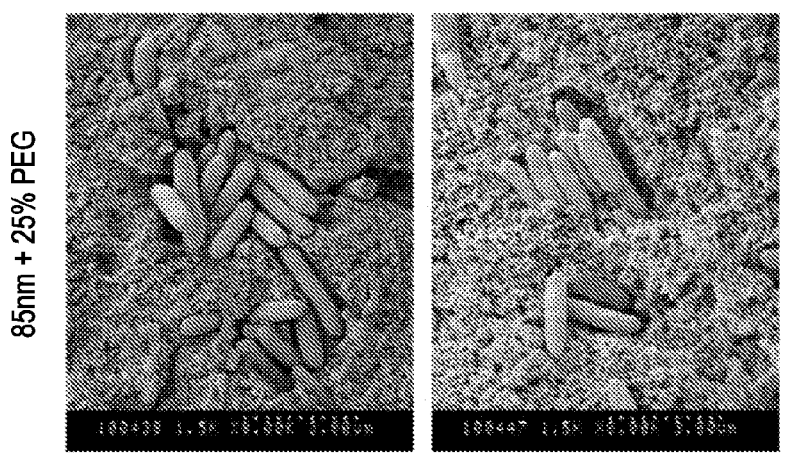
Figure 4:
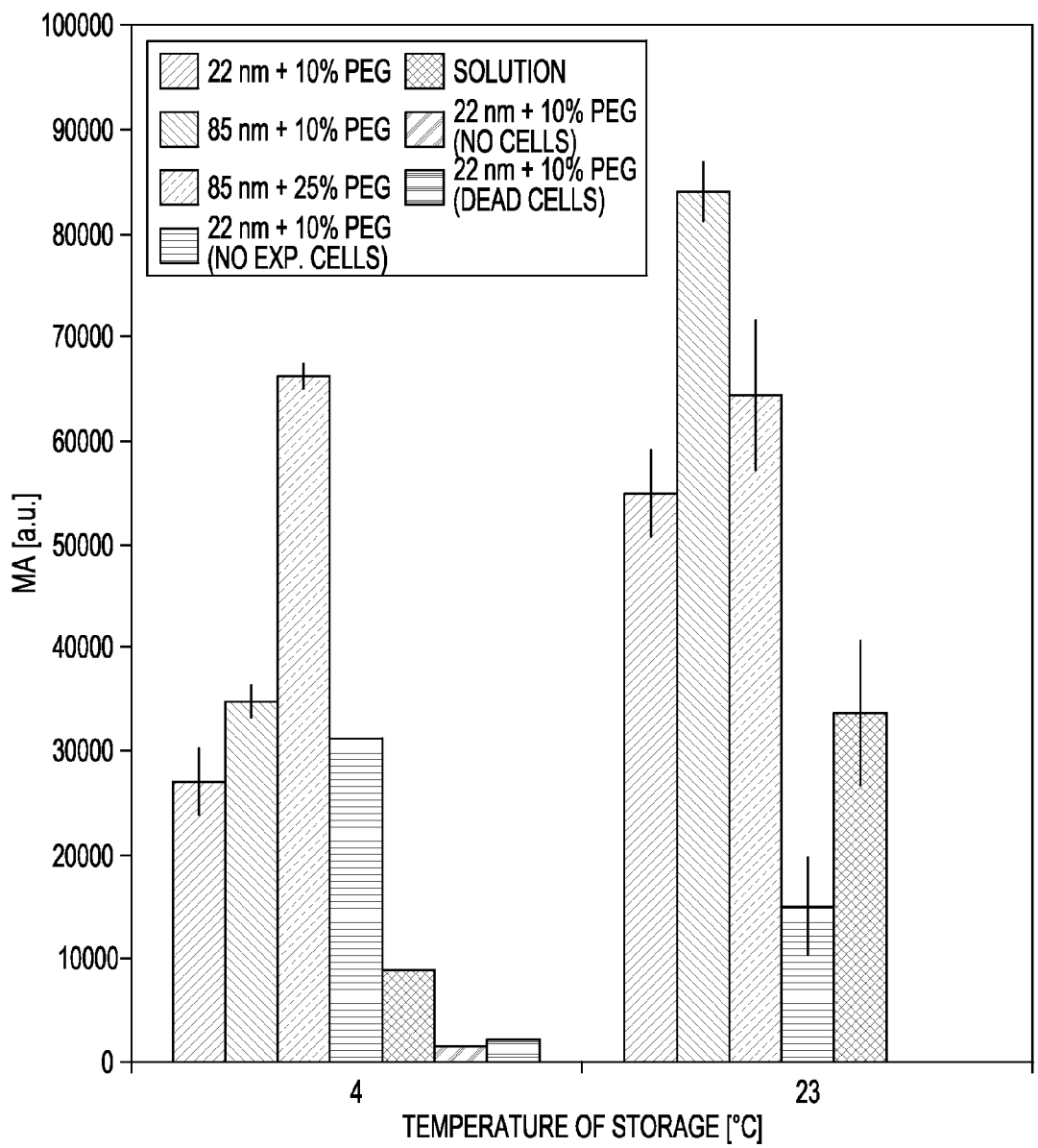
FIG. 4 illustrates the metabolic activity of silica-matrix encapsulated *E. coli* of one embodiment of the present invention at different temperatures.

FIG. 3 shows a typical structure prepared with cells. Three different reactive materials are shown, where the composition of the inorganic and organic part of the biomaterial was changed from 3.5% to 6.7% (silicon oxide) for the inorganic part and 10% to 25% (polyethylene glycol) for the organic part. FIG. 4 shows the metabolic activity of encapsulated cells over a period of two weeks. As it can be observed the activity of the cells in the gel increased. Without being bound to any theory of operation, it is postulated that over time the cell walls allowed the more facile exposure of the chemical-to-be-transformed to the enzyme that caused the chemical transformation.

Example 2. Preparation of Nanoporous Silica-Matrix Encapsulated Biomaterials

The materials included TMOS (1 ml); Hydrochloric acid (3 M); Polyethylene glycol (PEG), Mw=600 Da; Bacterial solution: 667 μl; Distilled water.

First, TMOS was hydrolyzed using HCl, with proportions such that for 1 ml of TMOS, 1 ml of water was added and 60 μl of 3M HCl was added. Next, 333 μl of hydrolyzed TMOS was mixed with 100 μl of PEG. A silica-matrix can also be prepared without the addition of PEG. Next, 667 μl of cell solution was gently pipetted into the mixture. Next, the mixture was transferred to desired containers for casting the gel. The gelation took place in 5 to 10 minutes. The gel was allowed to age for 1 to 2 hours and then water was added.

Example 3. Preparation of Macroporous Silica-Matrix Encapsulated Biomaterials

The materials included 400 mg of polyethylene glycol (PEG, Mw=10 kDa, from Sigma), 4 ml of 0.0125 M Acetic acid (99.9%, from Mallinckrodt), TMOS (2.5 ml), Bacteria Solution in water (1 ml). Cell concentration up to 0.4 g/ml.

Figure 5:
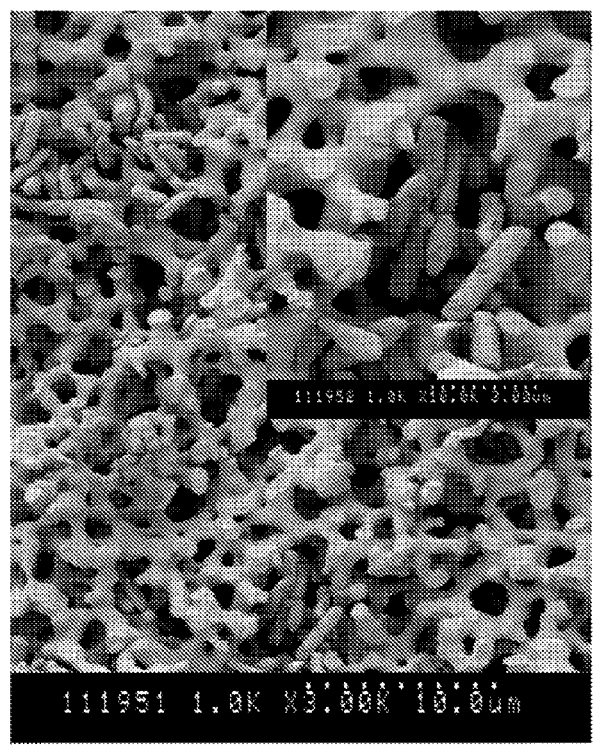
FIG. 5 illustrates macroporous silica-matrix encapsulated bacteria of one embodiment of the present invention.

First, PEG and acetic acid were added the container and stirring was maintained until a uniform mixture is achieved. The stir rate and time were 1200 RPM between 5 to 10 minutes. Next, the temperature of the container was lowered to 0° C. TMOS was added in a drop-wise manner, and keep stirring for additional 30 minutes. Next, the stirring was stopped, the stirrer was removed, and then 1 ml of bacterial solution was added. Next, samples were removed and pipette into the appropriate containers. The samples were allowed to gel and age at 40° C. for 18 to 24 hours. Then, the samples were removed from 40° C. and water was added at room temperature or 4° C. FIG. 5 shows a typical macroporous silica structure with bacteria (*E. coli*).

Example 4. Preparation of Macroporous Silica-Matrix Encapsulated Biomaterials

The materials included 740 mg of Pluronic P123® (Mw=6 kDa, from Sigma); Hydrochloric acid 0.014 M (6 ml); 6.25 ml of THEOS (>90%, from Gelest); and a bacteria solution in water (1 ml).

First, the container was prepared at 0° C. for mixing the materials. Next, P123 and HCl were poured in the container and stirring was maintained until a uniform mixture was achieved, at 1200 RPM for approximately 5 to 10 minutes was adequate. THEOS was added in a drop-wise manner, and stirring was maintained for 30 min. The stirring was stopped, the stirrer was removed, and then 1 mL of bacterial solution was added. The samples were removed and pipetted into the appropriate containers. The samples were allowed to gel and age at 40° C. for at least 48 hours. Then, the samples were removed from the 40° C. and water was added.

Figure 6:
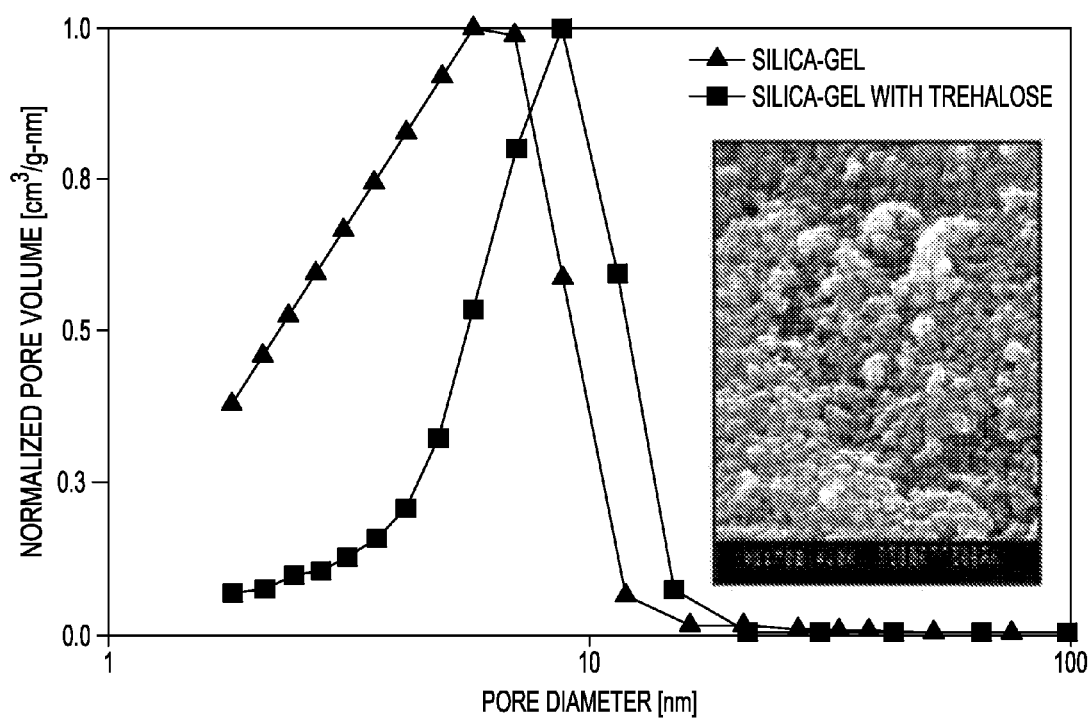
FIG. 6 illustrates the pore size distribution of mesoporous silica gels of various embodiments of the present invention.

Example 5. Increasing the Mesoporosity of the Silica-Matrix Encapsulated Biomaterials As a typical protocol polyethylene glycol or disaccharides were used for increasing the mesoporosity. The protocols were described in the previous sections. Measuring nitrogen gas absorption allowed the measurement of differences in the mesoporosity size distributions of the nanoporous gels that we used for the encapsulation. FIG. 6 shows the pore size distribution in the silica gels and the silica gels in the presence of Tre. Scanning Electron Microscopy (SEM) was performed to observe the surface characteristics of the material. The structure of the material was uniform without phase separation and it was formed by aggregates of coalesced particles.

Figure 7:
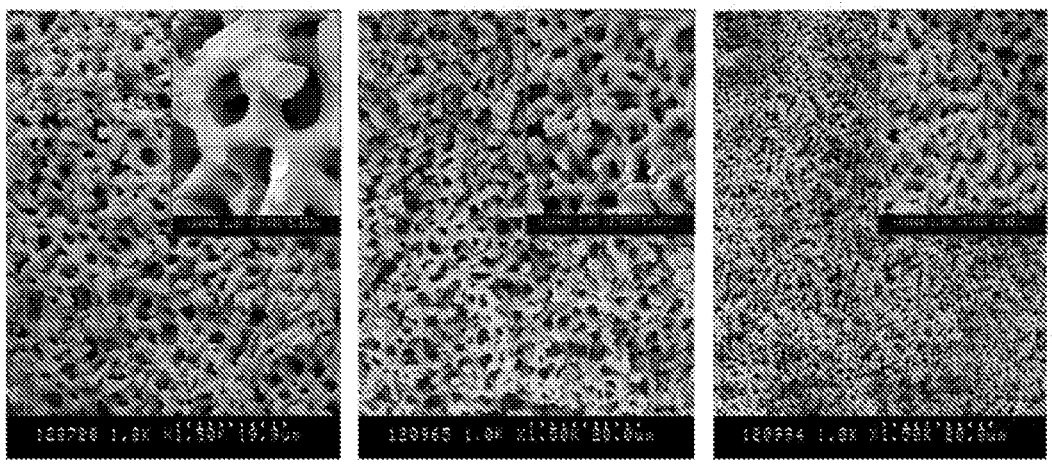
FIG. 7 illustrates the macroporosity of silica-matrixes made with various concentrations of PEG, in accord with certain embodiments.
Figure 8:
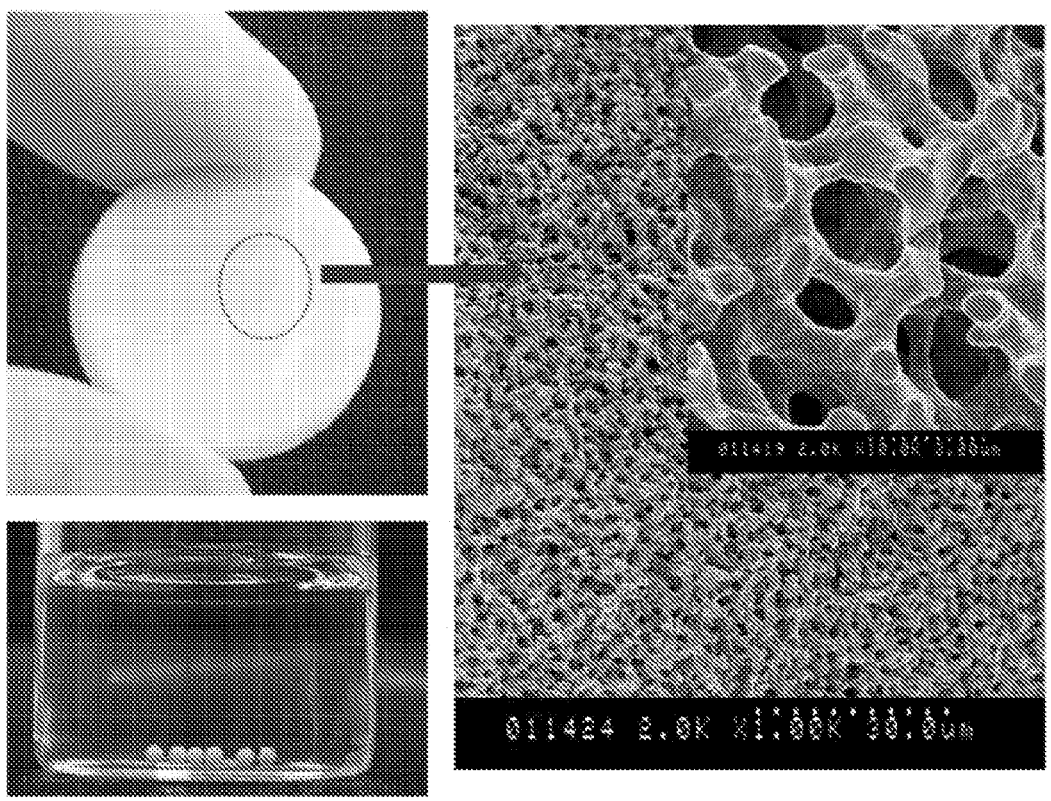
FIG. 8 illustrates various shapes of cast silica-matrix that include macroporosity, in accord with certain embodiments.

The macroporosity of the hybrid silica gel was also controlled by the type of organic polymer precursor, molar mass of the organic polymer, silica to polymer ratio, pH of reaction, temperature and time of gelling and aging conditions. FIG. 7 shows how porosity of the hybrid material can be tuned when the polymer concentration is increased. Moreover, FIG. 8 shows how the material can be casted in different shapes and the macroporosity still is present (SEM pictures).

Example 6. Modification of the Mechanical and Surface Chemistry Properties

Silica materials have high Yong's modulus (~7.5×10$^{10}$ Pa) due to rigidity of —O—Si—O— networks. However, rigidity of the matrix can be related by the incorporation of methyl groups (—$CH_3$) into the siloxane network, thereby providing a decrease in Yong's modulus (~$10^9$ Pa). Dimethylsiloxane was used to reduce the Yong's modulus, reaching rubbery regions (~$10^6$-$10^7$). The proportions were up to 30% in volume respect to the inorganic component. The molecular weights also varied from 0.3 to 5 kDa. The chemistry of the process followed the traditional sol-gel process (e.g. hydrolysis and condensation reactions), since silanol- or triethoxysilyl-terminated polydimethylsiloxane (PDMS) were used. The mechanical and surface chemistry properties of the hybrid silica material could also be modified when polysilsesquioxanes were incorporated into the matrix (e.g. methyl, dimethyl, trimethyl, vinyl, cyano, amino, epoxy, methacryl, or acrylic organic groups). Bridged polysilsesquioxanes also offered another possibility for changing the structure (see Table 1) such that organic groups may form additional crosslinking in the silica matrix. The properties of the hybrid materials obtained vary from brittle to rubbery and opaque to transparent depending on the inorganic component (chemistry structure, rate of hydrolysis and condensation, solubility), organic component (chemical structure, molecular weight, average chain length, end group), and mixture stage (organic-inorganic ratio, concentration of components in solution, water content, catalyst and concentration, temperature, time).

Figure 9:
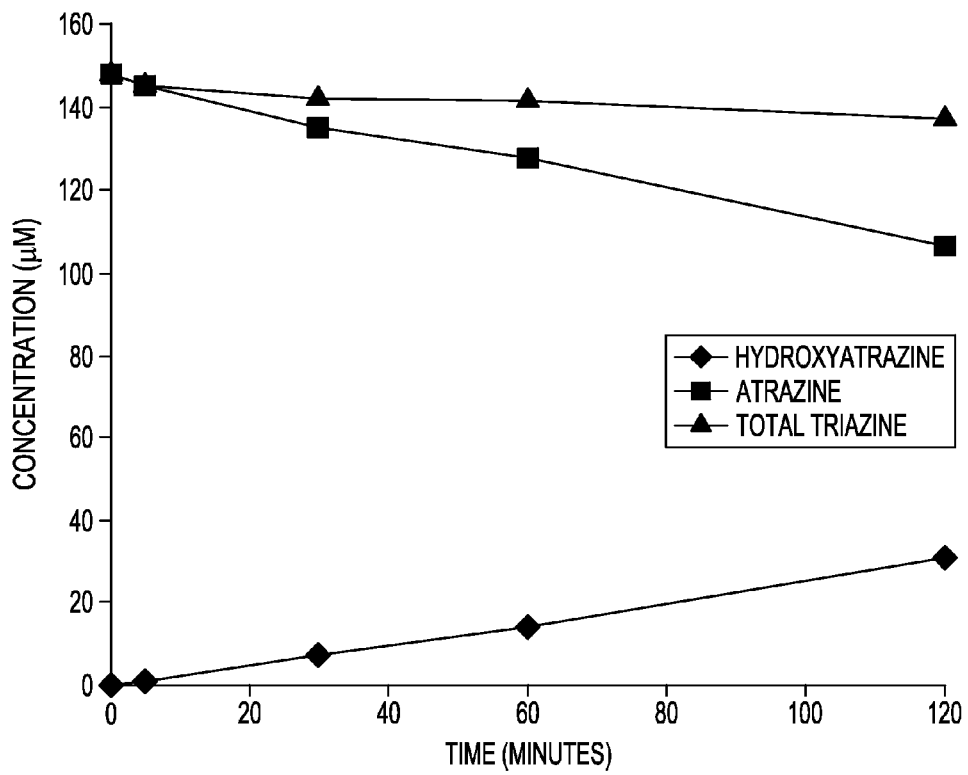
FIG. 9 illustrates a graph depicting assay results of AtzA-expressing *E. coli* cells encapsulated in a silica-matrix, in accord with certain embodiments.

Example 7. Immobilization of Atrazine Chlorohydrolase (AtzA)-Expressing Bacteria in a Silica Matrix for the Bioremediation of the Herbicide Atrazine Genetically-engineered *Escherichia coli* (*E. coli*) cells expressing the atzA gene encoding the AtzA protein, atrazine chlorohydrolase, were encapsulated in a silica gel-matrix, using the techniques disclosed here. FIG. 9 shows a graph depicting the typical assay results of AtzA-expressing *E. coli* cells encapsulated in a silica gel. Atrazine at a starting concentration of 150 μM is transformed into hydroxyatrazine via the dechlorination reaction catalyzed by AtzA. The y-axis is the concentration of atrazine or hydroxyatrazine in μM and the x-axis is reaction time in minutes. The red curve shows drop in atrazine, the blue curve is increase in hydroxyatrazine.

Figure 10:
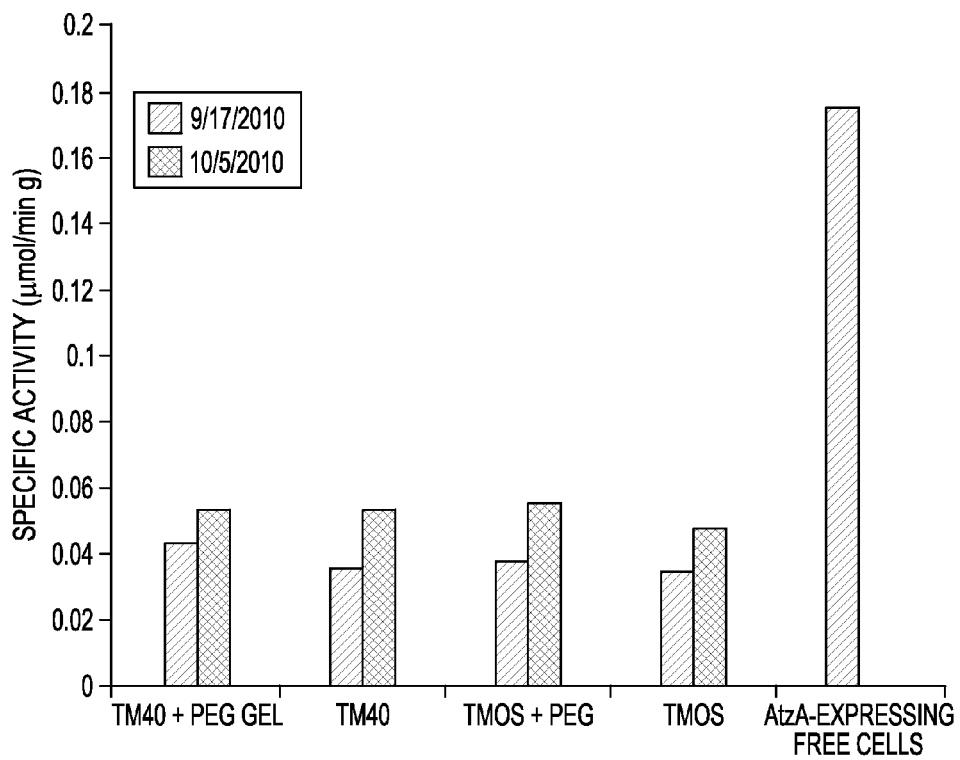
FIG. 10 shows the specific activity of various AtzA-expressing *E. coli* encapsulated in a silica-matrix after storage at 4° C., in accord with certain embodiments.

Silica matrixes with encapsulated *E. coli* cells expressing AtzA were stored at 4° C. after the initial assay. The gels were re-assayed more than two weeks later. The gel activity surprisingly increased over this time. The increase in activity was likely due to the deterioration of the cell membrane over time, diminishing the barrier between the enzyme and substrate. FIG. 10 shows the specific activity of various silica gels after storage at 4° C. The blue bars represent the first assay on Sep. 17, 2010 and the red bars represent the later assay on Oct. 5, 2010. The increase in activity on Oct. 5, 2010 is likely due to a breakdown of the *E. coli* cell membrane. The blue bar on the far right represents *E. coli* cells in free suspension which is the highest possible activity.

The results shown in FIG. 10 suggested that increased permeability of the cell membrane can increase the atrazine-degradation activity of *E. coli* cells expressing AtzA. Assays were carried out to determine the effect of membrane permeability on the activity of AtzA-expressing *E. coli* cells on atrazine in free suspension (not in silica gels). Artificially increased membrane permeability via two methods: Incubation of cells with acetone, an organic solvent; and incubation of cells with Triton™ X-100, a non-ionic detergent.

Figure 11:
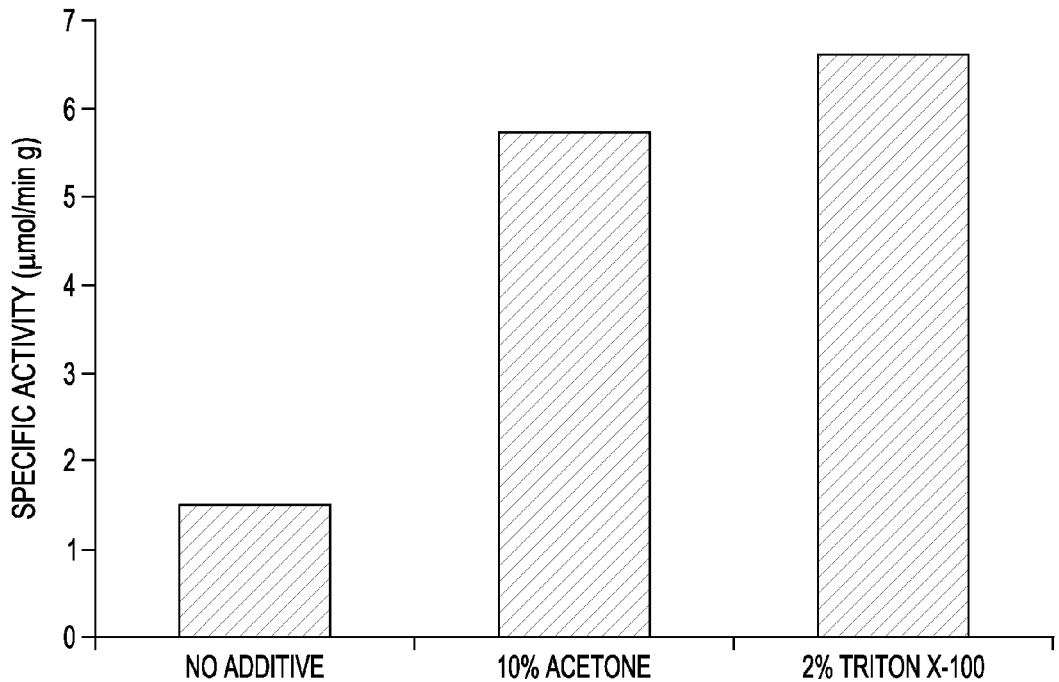
FIG. 11 shows a bar graph illustrating the atrazine-degradation activity of free suspension *E. coli* cells expressing AtzA without treatment ("no additive") and after treatment with either acetone or the detergent Triton™ X-100, in accord with certain embodiments.
Figure 12:
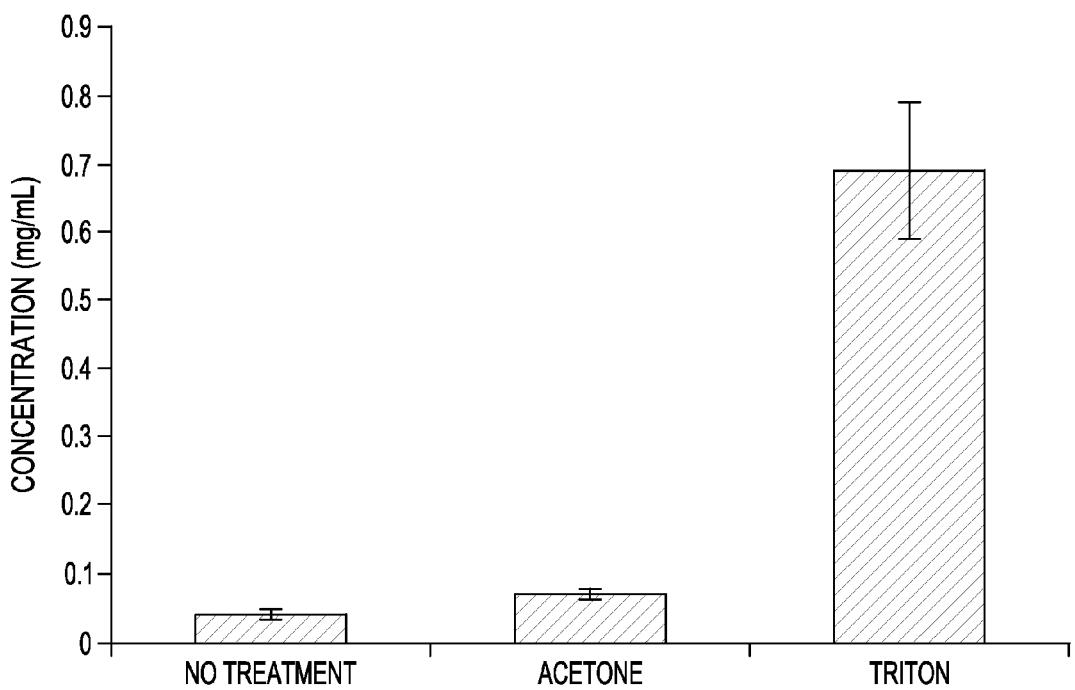
FIG. 12 shows the protein release of free suspension *E. coli* cells expressing AtzA after treatment with either the organic solvent acetone or the detergent Triton™ X-100, in accord with certain embodiments.

In addition to activity on atrazine, we also monitored protein release since high protein release due to membrane disruption may result in protein loss and decreasing activity over time. It was determined that acetone was an ideal cell permeablilizing agent due to high increase in activity (FIG. 11) yet low protein release (FIG. 12) FIG. 11 shows a bar graph illustrating the atrazine-degradation activity of *E. coli* cells expressing AtzA without treatment ("no additive") and after treatment with either acetone or the detergent Triton™ X-100. FIG. 12 shows protein release of *E. coli* cells expressing AtzA after treatment with either the organic solvent acetone or the detergent Triton X-100. Although cell permeabilization with Triton™ X-100 resulted in higher activity (see FIG. 11), the much greater protein release makes Triton™ X-100 treatment less attractive. It is desirable to permeabilize the cells and make them non-viable, while at the same time retaining high levels of enzymes in the silica matrix.

Figure 13:
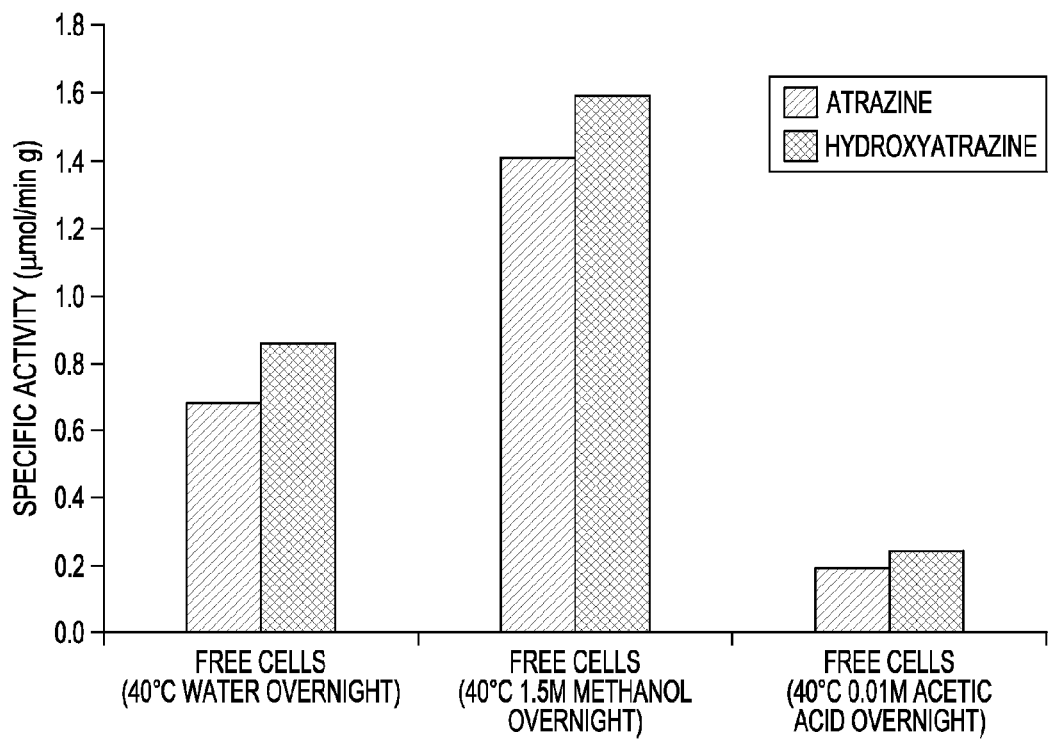
FIG. 13 illustrates the specific activity of *E. coli* cells expressing AtzA on atrazine solutions and conditions of gel formation, in accord with certain embodiments.

FIG. 13 illustrates the specific activity of *E. coli* cells expressing AtzA on atrazine solutions and conditions of gel formation.

Example 8. TMOS and MTMOS

The materials included 1 ml of TMOS (tetramethylorthosilicate, ≥98%, from Fluka Analytical); 1 ml of MTMOS (methyltrimethoxysilane, ≥95%, from Fluka Analytical), 0.01 M Hydrochloric acid (28% to 30%, from Mallinckrodt); Silica nanoparticles (SNPs): 22 nm, or 85 nm (30% to 40%, from Sigma and Nyacol); Polyethylene glycol (PEG), (Mw=600 Da), from Sigma); Bacterial solution: 400 μl. At a concentration of 0.1 g/ml; Distilled water.

First, TMOS and MTMOS were hydrolyzed with water in the presence of HCl (1/1/1.5/0.1, TMOS/MTMOS/Water/HCl, v/v/v/v). The hydrolysis process can be done using an ultrasonic or magnetic stirrer mixer. The byproduct of the hydrolysis can be removed using rotoevaporation or heating the mixture. Next, a water dilution of silica nanoparticles (SNPs) was prepared. For 22 nm SNPs, a dilution of 3.11 M can be prepared, for example. For 85 nm (SNPs) a dilution of 2.88 M can be prepared, for example. Next, 200 μl of hydrolyzed TMOS was mixed with 400 μl appropriate SNPs dilution, then add 100 μl of PEG was added. A silica-matrix can also be prepared without the addition of PEG. Next, 400 μl of cell solution is added by gently pipetting the mixture. Next, the mixture was transferred to the desired containers for casting the gel. Gelation took place in 5 to 10 min. The gel was aged at 40 C for 24 hr.

Figure 14:
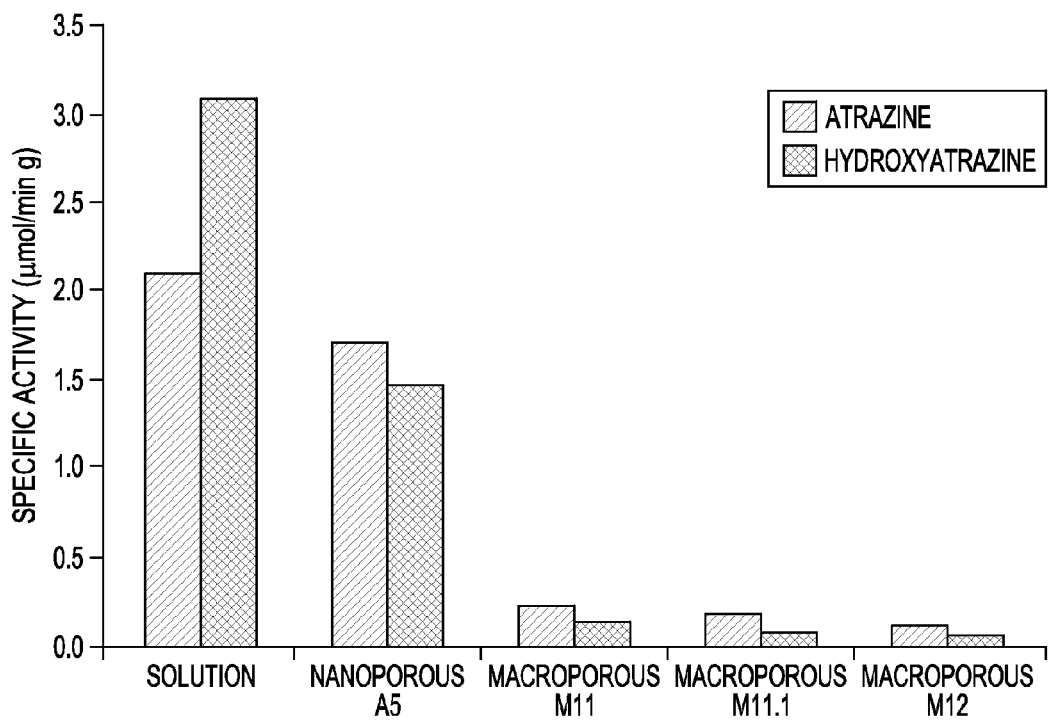
FIG. 14 illustrates the specific activity of encapsulated *E. coli* cells expressing AtzA, in accord with certain embodiments.

FIG. 14 illustrates the specific activity of encapsulated *E. coli* cells expressing AtzA. Note: A5 is in bead form; M11, M11.1, and M12 are in film form, as shown by Table 5.

TABLE 5

| Precursor | Cross-Linker | Bacteria Density | Additives | Additional additive | Curing time (h) | T of Reaction | Key |
|---|---|---|---|---|---|---|---|
| 400 µL TM40 (22 nm): water(1:1) | 200 µL (1:1:1.5:0.15) TMOAS:MTMOS: water:0.01M HCl | 400 µL 0.2 g/mL | 100 µL 600 Da PEG | | 12 | 40 | A5 |
| 6 mL water | 6.25 mL THEOS | 1 mL 0.2 g/mL | 0.75 g P123 | | 18-20 | 40 | M11 |
| 6 mL water | 6.25 mL THEOS | 1 mL 0.2 g/mL | 0.75 g P123 | 4 µL 3M HCl | 18-20 | 40 | M11.1 |
| 4 mL 0.0125M acetic acid | 3 mL 2 mL TMOAS: 1 mL MTMOS | 1 mL 0.2 g/mL | 0.4 g 10K Da PEG | 12 µL NH₃OH; water (1:1) | 18-20 | 40 | M12 |

Figure 15:
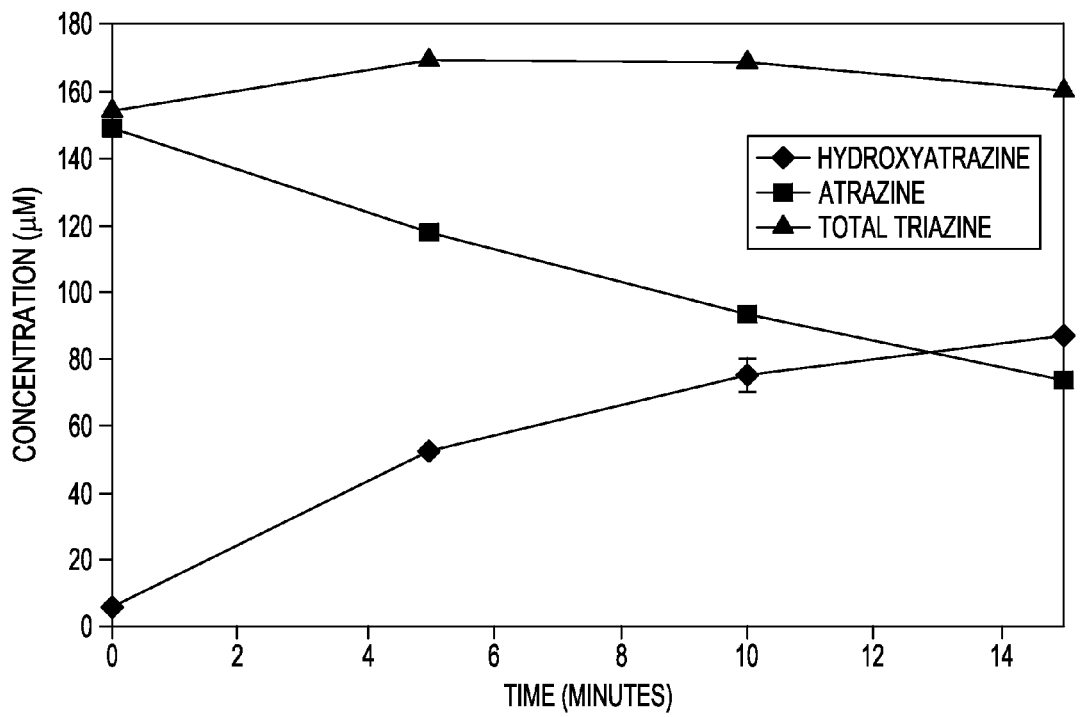
FIG. 15 illustrates the hydroxyatrazine and atrazine concentrations on different gels with cells, in accord with certain embodiments.

FIG. 15 illustrates the hydroxyatrazine and atrazine concentrations on different gels with cells.

Figure 16:
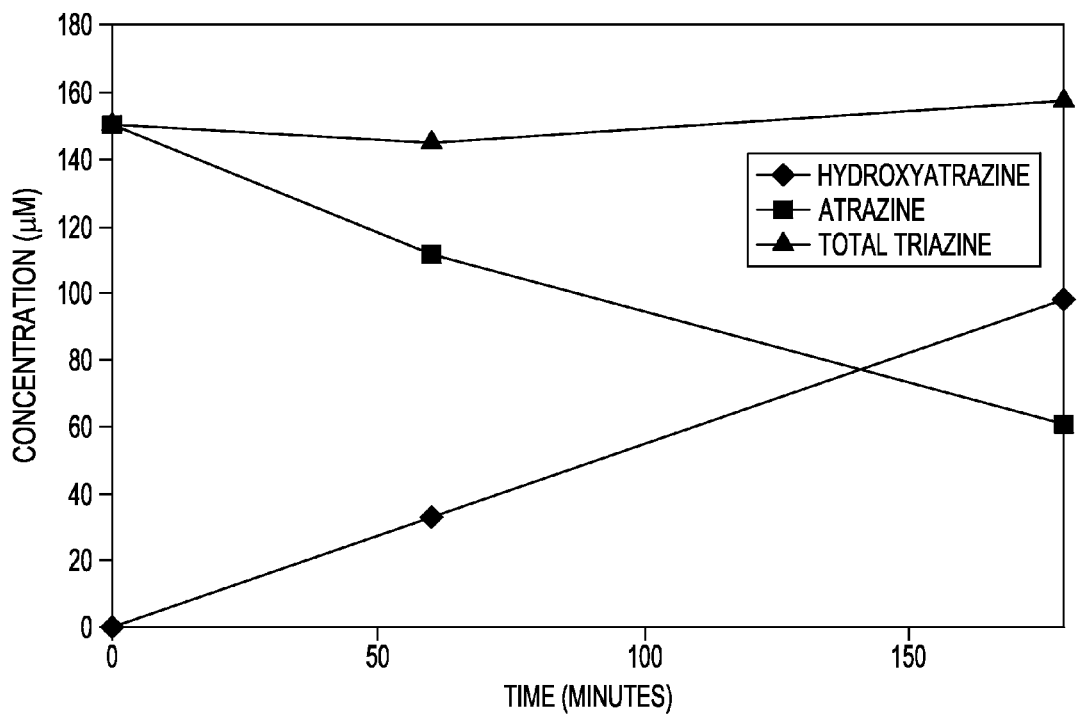
FIG. 16 illustrates the hydroxyatrazine and atrazine concentrations on different gels with cells, in accord with certain embodiments.

FIG. 16 illustrates the hydroxyatrazine and atrazine concentrations on different gels with cells.

Figure 17:
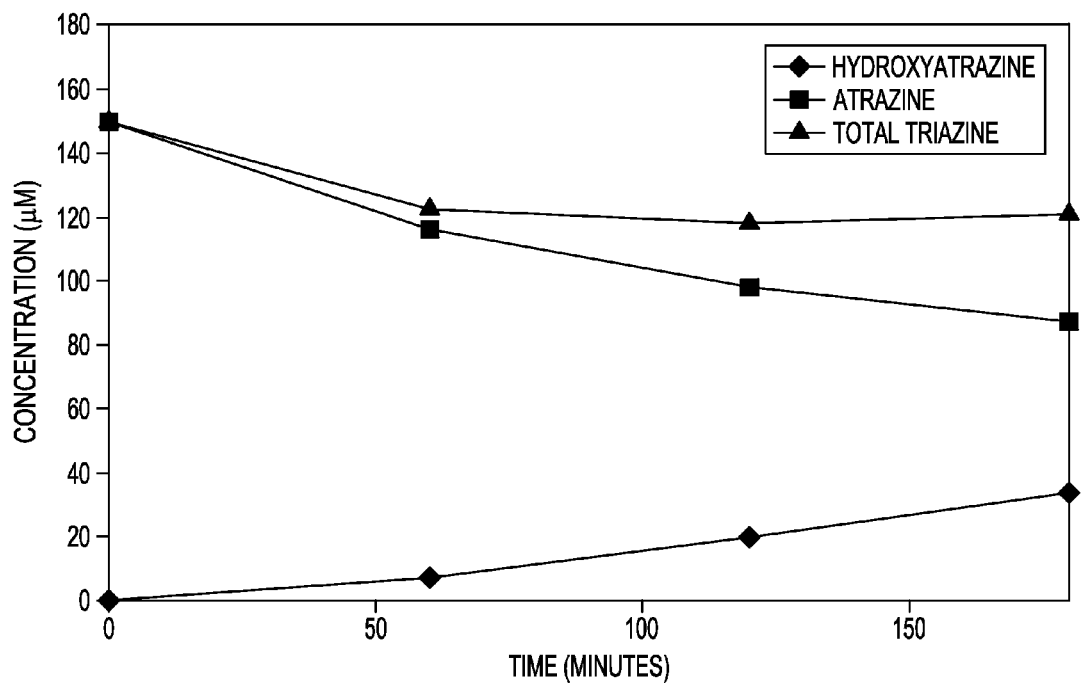
FIG. 17 illustrates the hydroxyatrazine and atrazine concentrations on different gels with cells, in accord with certain embodiments.

FIG. 17 illustrates the hydroxyatrazine and atrazine concentrations on different gels with cells.

Figure 18:
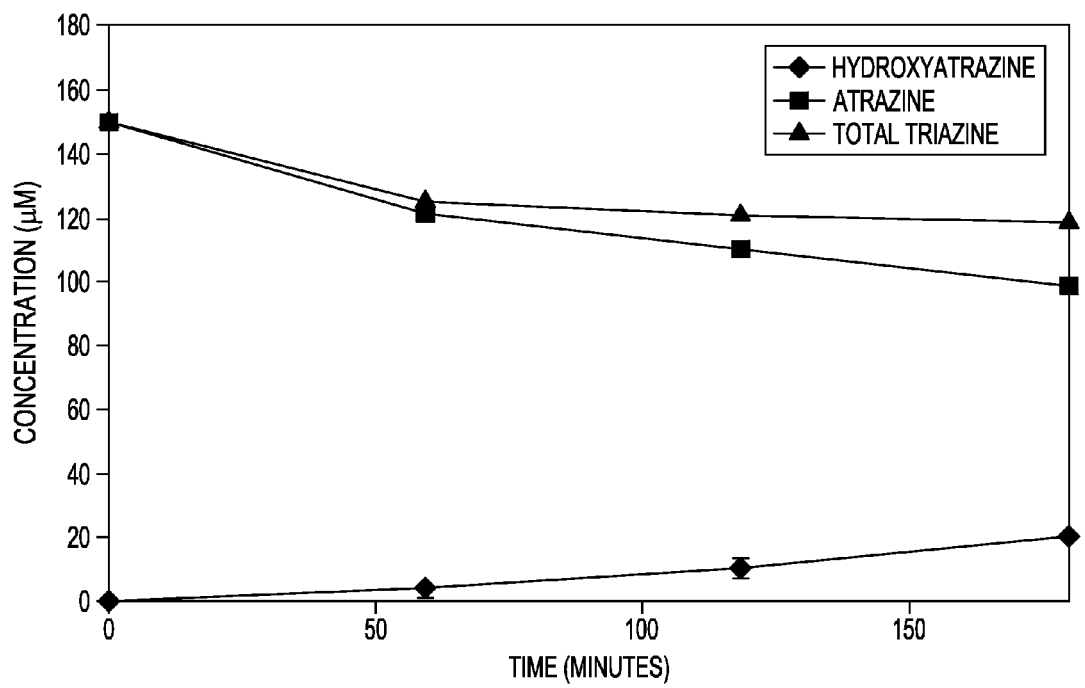
FIG. 18 illustrates the hydroxyatrazine and atrazine concentrations on different gels with cell, in accord with certain embodiments.

FIG. 18 illustrates the hydroxyatrazine and atrazine concentrations on different gels with cells.

Example 9. Atrazine Biodegradation

Overview and General.

The herbicide atrazine (2-chloro-4-ethylamine-6-isopropylamino-s-triazine) can be used for control of broadleaf weeds in crops such as corn, sorghum, and sugarcane. Atrazine is currently used in 70 countries at an estimated annual rate of 111,000 tonnes. Atrazine is typically applied early in the planting season. Heavy rainfall events shortly after application may lead to detectable atrazine concentrations in waterways and in drinking-water supplies. In some instances, municipal water treatment plants may use chemicals and other treatment processes such as activated carbon to reduce atrazine and for other drinking water quality purposes.

A biomaterial including recombinant E. coli cells overexpressing atrazine chlorohydrolase (AtzA) encapsulated in a polymer/silicon oxide matrix prepared by the sol-gel process described herein was used to degrade atrazine in water. AtzA catalyzes hydrolytic removal of the chlorine atom of atrazine, producing hydroxyatrazine, as shown below.

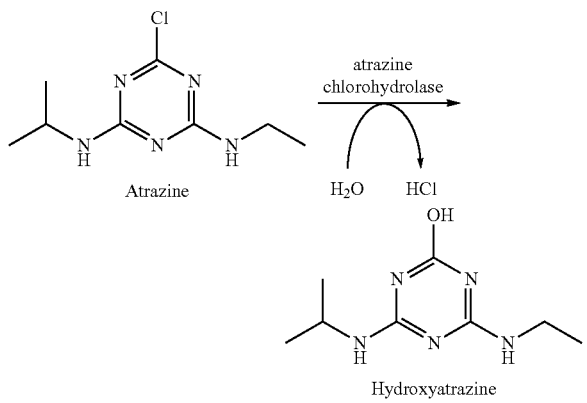

The gelation process was conducted using mild chemical reactions, thus helping to prevent loss of enzyme activity over time. Conditions were developed that led to non-viable cells that remained active in degrading atrazine over a long time scale. The silica-matrix encapsulating the microorganisms included a combination of silicon oxide precursors (e.g., silica nanoparticles, alkoxides) and a biocompatible organic polymer (e.g., polyethylene glycol, PEG). The porous material enabled diffusion of water and atrazine into the gel, and diffusion of hydroxatrazine out of the gel. The gel also adsorbed atrazine, a property that contributed to removal of atrazine from the solution in the process. In this context, the encapsulated organism has the potential to outperform activated carbon in a water treatment application since it acts to both adsorb and additionally to degrade atrazine. As shown in Example 12, the final material exhibited activity for at least about four months. In total, these studies indicated that the described hybrid biomaterial could potentially be used continuously for the biodegradation of atrazine without the need for regeneration.

Silica Gel Synthesis.

Different silica precursors were used for the synthesis of the porous gel matrix. The gel was colloidal silica nanoparticles Ludox® TM40 (40% w/w), tetramethyl orthosilicate (TMOS, 98%), and methyltrimethoxy silane (MTMOS, 97%). The organic polymer, polyethylene glycol (PEG, molecular weight ($M_w$): 600 Da), was incorporated into the porous matrix, increasing biocompatibility of the matrix. All of the materials were purchased from Sigma (Sigma-Aldrich Corp. St. Louis, Mo.).

Bacterial Strains and Growth Conditions.

E. coli DH5α (pMD4) was grown at 37° C. in superbroth medium comprised of 1.2% tryptone (w/v), 1.4% yeast extract (w/v), 0.5% glycerol (v/v), 0.38% monobasic potassium phosphate, 1.25% dibasic potassium phosphate, and 30 µg/ml chloramphenicol (at pH 7.4). Starter cultures were made by inoculating 5 ml of superbroth with an isolated colony and incubating overnight at 37° C., with shaking at 250 rpm. Intermediate cultures were grown by inoculation with 3% (v/v) starter culture. Cultures were grown to an optical density (OD) of 0.5-0.75 with shaking at 250 rpm. Cell production flasks were inoculated with 3% (v/v) of intermediate cultures and grown for 16 h under the same growth conditions. Cells were harvested by centrifugation at 9000 rpm for 20 min at 4° C. and re-suspended in water to a final concentration of 0.1-0.2 g of cell/ml.

Reactive Biomaterial Production.

Bacterial cells were encapsulated using a variation of a sol-gel method previously described. Cells were encapsulated in silica or silica-PEG (SPEG) gels. Porous gels were formed by diluting TM40 silica nanoparticles in ultra pure water (with electrical resistivity>18.2 MΩ·cm at 25° C.). PEG ($M_w$=600 Da) was added to the solution at a volume ratio of 1:4 ($r_{PEG}$), and the mixture was stirred vigorously for 10 min. The resulting TM40-PEG solution was cooled in an ice bath. Separately, TMOS or TMOS/MTMOS were hydrolyzed by sonication in the presence of 0.01 M HCl. A typical volume ratio was 1:1:0.1 for TMOS/water/HCl and 1:1:1.5:0.15 for the TMOS/MTMOS/water/HCl solution. The hydrolyzed solution was mixed with the TM40-PEG solution at a volume ratio of 1:2 ($r_d$). Finally, a cell suspension (0.1 or 0.2 g of cells/ml) was added to the mixture at a volume ratio of 1:1 ($r_{cs}$). The samples (Table 6) were transferred to glass or metal molds and were cured at different temperatures and times in a convection oven. The final products were formulated into microbeads (1.0-1.5 mm diameter) or into a cylinder block (~1 ml in volume formed inside a scintillation vial, resulting in a diameter of approximately 25 mm and a thickness 2 mm) (FIG. 19).

TABLE 6

Composition of silica gels.

| Gel Type | Precursor [M] | PEG $r_{PEG}$ [v/v] | Cross-Linker Type | $r_{Cl}$ [v/v] | $r_{CS}$ [v/v] | E. coli cells [g of cell/mL] | Incubation [° C.] |
|---|---|---|---|---|---|---|---|
| N1 | 1.24 | — | I | 0.5 | 1 | 0.1 | 23 |
| N2 | 1.13 | 0.25 | I | 0.5 | 1 | 0.1 | 23 |
| N3[a] | 1.13 | 0.25 | I | 0.5 | 1 | 0.1 | 23 |
| N4[b] | 1.13 | 0.25 | I | 0.5 | 1 | — | 23 |
| N5 | 1.71 | 0.25 | II | 0.5 | 1 | 0.1 or 0.2 | 23 or 45 |

[a] E. coli non-expressing AtzA,
[b] No cells, I: TMOS:Water:0.01M HCL (1:1:0.1 v/v/v), II: TMOS:MTMOS:Water:0.01M HCL (1:1:1.5:0.15 v/v/v/v), $r_{PEG}$ = volume of PEG/volume of precursor, $r_{cl}$ = volume of cross-linker/volume of precursor, $r_{cs}$ = volume of cell solution/volume of precursor.

Cell Viability Assay.

The plate-count assay was used to determine cell viability of encapsulated cells. A known mass of wet gel was pulverized by gentle compression between two glass slides to release the encapsulated E. coli. The resulting material was suspended in 3 ml of sterile phosphate buffered saline (PBS). The solution was serially diluted at 100-fold increments and spread-plated, in triplicate, onto LB-agar plates. Plates were incubated at 37° C. for 24 h.

Lipid Membrane Analysis of Encapsulated Cells.

Conformation of cellular membrane lipids was characterized using Fourier Transform Infrared (FTIR) spectroscopy. Before gelation, 0.2 µL of the cell sample was sandwiched between two $CaF_2$ windows that were separated by a thin layer of vacuum grease on the sides and placed on a temperature controlled cryostage (FDCS 196, Linkam Scientific Instruments Ltd., UK). FTIR spectra were collected in the 930-7000 $cm^{-1}$ range using a Nicollet Continuµm FTIR microscope, equipped with a DTGS detector (Thermo-Nicollet Corp., Madison, Wis.). FTIR spectra were collected at 4, 10, 23, and 37° C. Spectral analysis was performed using Omnic software provided by the manufacturer. The lipid conformation change in the cellular membranes was monitored by measuring the peak location of the ν-$CH_2$ (symmetric stretching) band located near 2850 $cm^{-1}$. Due to significant contributions of the PEG $CH_2$ chains in the 2700-3000 $cm^{-1}$ region of the IR spectra, only silica gels without PEG were used for the analysis.

Atrazine Dechlorination Activity Assay.

Activity measurements of the encapsulated cells, in a cylinder block or in microbead form, were conducted at room temperature and at 4° C. in 20 ml glass scintillation vials. The reaction was initiated by exposing the cylinder block on one surface to 5 ml of 0.1 M potassium phosphate buffer (at pH 7.0) containing 150 µM (32.4 ppm) atrazine. In the experiments conducted with microbeads, 100 microbeads were suspended 5 ml of the same solution used for the cylinder blocks. The solution was continuously stirred using an orbital shaker at 200 rpm. The supernatant was sampled at four time points until 10-20% of the substrate was reacted. Each time point was taken in duplicate, and each sample was taken from an individual scintillation vial. The samples were heated to boiling point for 5 min to ensure that any released enzyme was inactivated, and filtered through a 0.2 µm pore size PTFE syringe filter to remove any bead fragments or cells that may have been released. The concentrations of atrazine and its metabolite, hydroxyatrazine, in the sample solution were measured by High-Performance Liquid Chromatography (HPLC) as previously described. For long term activity measurements, the encapsulated and free cells were stored in water at 4° C. and assayed as described above.

Characterization of the Porous Gel.

For electron microscopy imaging, silica or SPEG gels that contained encapsulated bacteria were chemically fixed initially using 2% glutaraldehyde, and then 1% osmium tetraoxide diluted in 0.1 M sodium cacodylate. After fixation, samples were gradually dehydrated by exposure to 50, 70, 80, 95, and 100% ethanol. The samples were then transferred to a $CO_2$ critical point drier (Samdri-780A, Tousimis, Rockville, Md.). Dried samples were sputtered with tungsten at a rate of 1 A°/min for 10 min. The gels that did not contain bacteria were sputtered without fixation. Scanning electron microscopy was conducted with a Hitachi S-900 FESEM (Hitachi Co, Lawrenceville, Ga.) scanning electron microscope. Samples were imaged at different magnifications using a 1.5 or 2 KV accelerating voltage.

Results.

In this study encapsulated recombinant E. coli cells expressing AtzA were used to reduce atrazine in water. The gels have two desirable characteristics with respect to the herbicide: they are able to both adsorb atrazine and to transform it into hydroxyatrazine, which is dissimilar toxicologically from atrazine and is more biodegradable. The cells were rendered non-viable to eliminate any risk of a potential release during use.

Viability of Encapsulated Recombinant E. coli.

Figure 19A:
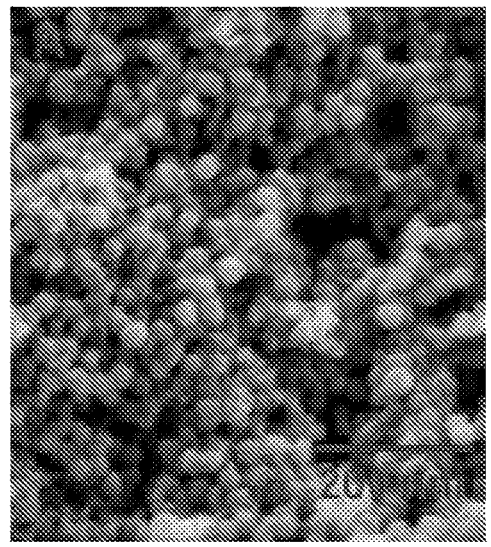
FIG. 19A illustrates an electron microscopy image of porous gel, in accord with various embodiments.
Figure 19B:
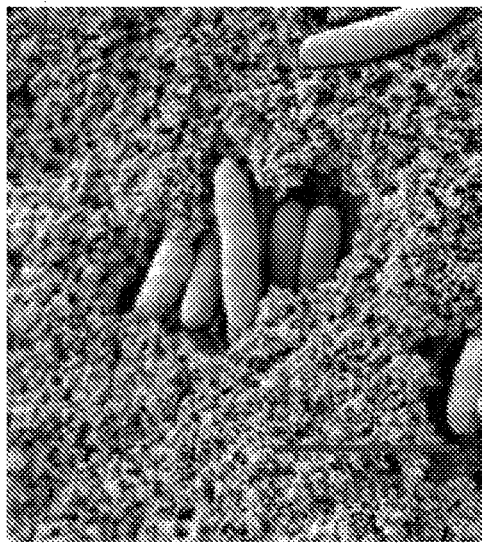
FIG. 19B illustrates *E. coli* encapsulated in N1 expressing AtzA, in accord with various embodiments.
Figure 19C:
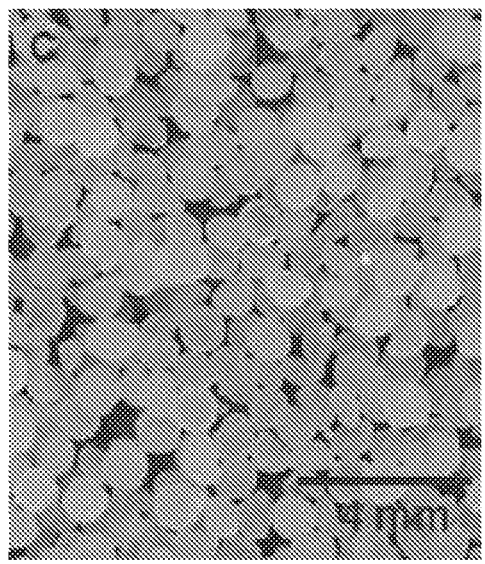
FIG. 19C illustrates microbeads containing *E. coli* expressing AtzA, in accord with various embodiments.
Figure 19D:
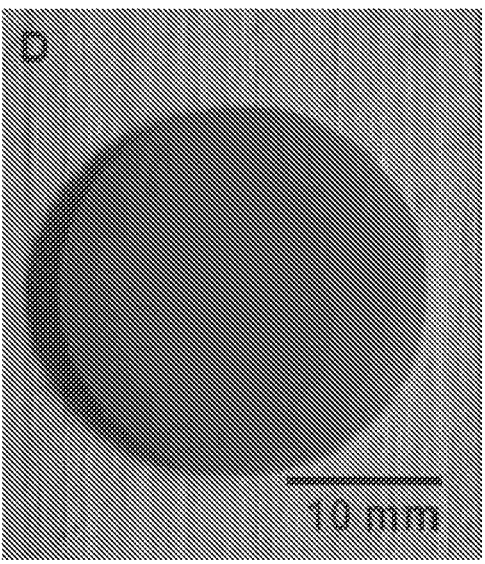
FIG. 19D illustrates cylinder block containing *E. coli* expressing AtzA, in accord with various embodiments.

Different silica gel compositions were tested for encapsulation efficiency and enzymatic activity (Table 6). The ultrastructure of the gels showed uniform condensation and aggregation of silica nanoparticles (FIG. 19A) around the encapsulated cells, generating a hyperporous network. At lower resolutions (FIG. 19B) small groups of E. coli were observed to be homogeneously distributed across the volume of the gels. FIGS. 19C and 19D show the two geometries used in this study; microbeads and a cylinder block containing E. coli expressing AtzA, respectively. Cylinder blocks were used in initial experiments for optimization of the silica gel material and maximum bioactivity. In contrast, the microbeads were used for long-term activity assays and were developed for future field studies since they have the highest area/volume ratio and thus are expected to yield the highest activity (among offering other advantages).

Most of the studies conducted to date with encapsulated E. coli in silica gels focus on the long-term cell viability after encapsulation. However, the degradation of atrazine by recombinant E. coli expressing AtzA does not require viable cells since the atrazine is dechlorinated by a non-metabolic hydrolytic reaction. This is a very important aspect for practical decontamination of drinking water since negligible (if possible, zero) viability of the encapsulated cells is required. This minimizes the environmental risks in case of an accidental release of the recombinant microorganisms. Therefore, a way of minimizing the viability of the encapsulated cells was developed.

Figure 20:
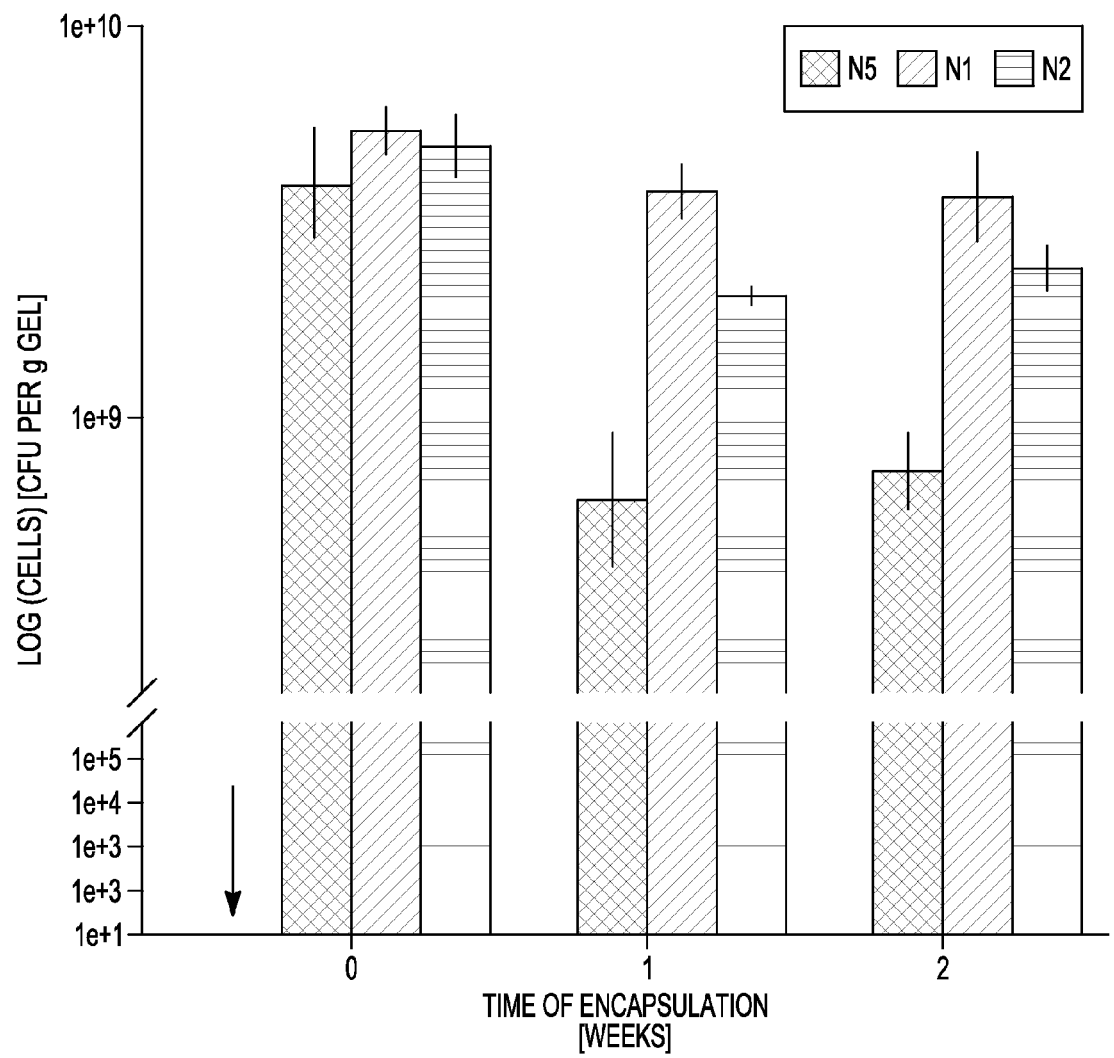
FIG. 20 illustrates the colony forming units per a gram of gel material for *E. coli* expressing AtzA extracted from different porous gels (n=3), in accord with various embodiments.

FIG. 20 shows colony forming units (CFU) per gram of gel material of *E. coli* expressing AtzA extracted from different porous gels (n=3), and shows the loss of viability of cells encapsulated in different porous gels. When the N5 gels were incubated at 45° C. for 24 h, a reduction in survival/viability of the encapsulated cells close to 100% was accomplished. Moreover, after 3 weeks of encapsulation no viable cells could be detected. The cells extracted from the N1, N2, and N5 (non-thermally treated) gels after 3 weeks of encapsulation had 93.4%, 49.3%, and 92.2% less viable cells, respectively, when compared to cells extracted at t=0 weeks. This showed that encapsulation of *E. coli* in the gels non-thermally treated still contained viable gels even after a long period of time of encapsulation.

Membrane Analysis of Encapsulated Cells.

The significant decrease in survival of the encapsulated *E. coli* with increased gelation temperature was explored using FTIR spectroscopy by monitoring the change in the location of the lipid acyl chain (v-$CH_2$) stretching peak (located near 2850 $cm^{-1}$ in solution). Before gelation, the v-$CH_2$ peak locations of the cells in the silica solution were similar to the cells in water (Table 7) indicating that the microenvironment of the cells in the silica solution were similar to the cells in water. When the measurements were repeated 30 min after the gels were formed, the encapsulated cells had significantly lower v-$CH_2$ values than the cells in water (Table 7). The decrease in the v-$CH_2$ wavenumber reflects an increased packing of the membrane lipids of the cells due to encapsulation. When the encapsulated cells were incubated for 24 h at 45° C., there was a gradual shift in the v-$CH_2$ peak location to higher wavenumbers, which indicated disruption of the cellular membranes of the encapsulated cells. In parallel experiments, encapsulated cells were dried over time at room temperature to monitor the changes in the v-$CH_2$ peak position. The results showed that the v-$CH_2$ peak position shifted towards higher wavenumbers as the sample was dried over time (FIG. 21). FIG. 21 shows the time-dependent v-$CH_2$ peak position of encapsulated *E. coli* expressing AtzA in silica gels. Additionally, measurements of the v-$CH_2$ peak position for free and encapsulated cells at different temperatures revealed that the fluidity of the membrane decreased with encapsulation. For a temperature change from 4° C. to 37° C., $\Delta$v-$CH_2$ was 1.13 $cm^{-1}$ for the free cells while it decreased down to ~0.47 $cm^{-1}$ for the encapsulated cells.

TABLE 7

Changes in the structural conformation of lipid membranes of *E. coli* expressing AtzA with temperature and encapsulation conditions.

| Temperature [° C.] | v-$CH_2$ peak position [$cm^{-1}$] | | |
|---|---|---|---|
| | Solution | Gel | Gel (Thermally Treated) |
| 4 | 2851.77 ± 0.1 | 2844.13 ± 0.2 | 2847.53 ± 0.6 |
| 10 | 2851.90 ± 0.0 | 2844.17 ± 0.1 | 2847.36 ± 0.8 |
| 23 | 2852.33 ± 0.1 | 2844.40 ± 0.2 | 2847.66 ± 0.8 |
| 37 | 2852.90 ± 0.0 | 2844.60 ± 0.1 | 2847.96 ± 0.1 |

FIG. 22 shows electron microscopy images of *E. coli* expressing AtzA: (A) free cell in solution, (B) *E. coli* encapsulated in SPEG gel, N5, (C) *E. coli* encapsulated in SPEG gel, N5 after thermal treatment at 45° C. A comparison of the cells in solution and encapsulated cells did not show any significant difference in the morphology of their external membranes (FIG. 22A and FIG. 22B). Distinctive raffles of the external membrane were observed in both cases. However, cells that were encapsulated and incubated for 24 h at 45° C. did not have the same characteristics of the external membrane. Instead, the membrane looked shrunken and dehydrated (FIG. 22C). Both the FTIR analysis and SEM imaging showed the significant differences between the cells encapsulated at room temperature and the cells treated at 45° C. which resulted in decrease viability.

Atrazine Biodegradation.

Figure 23A:
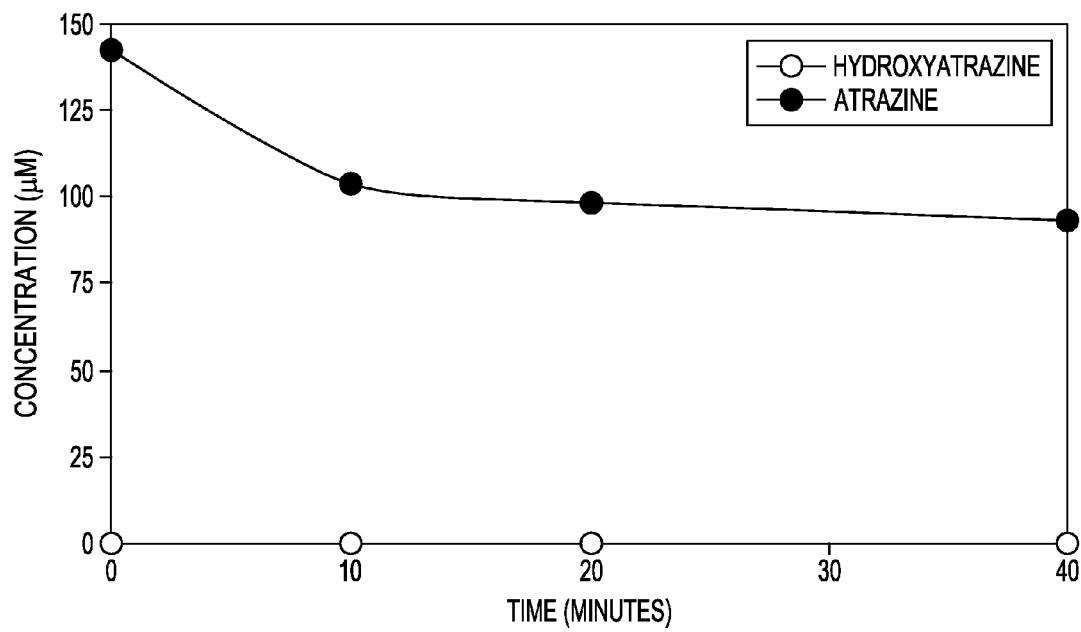
FIGS. 23A and B illustrate changes in atrazine and hydroxyatrazine concentration in solution, in accord with various embodiments.
Figure 23B:
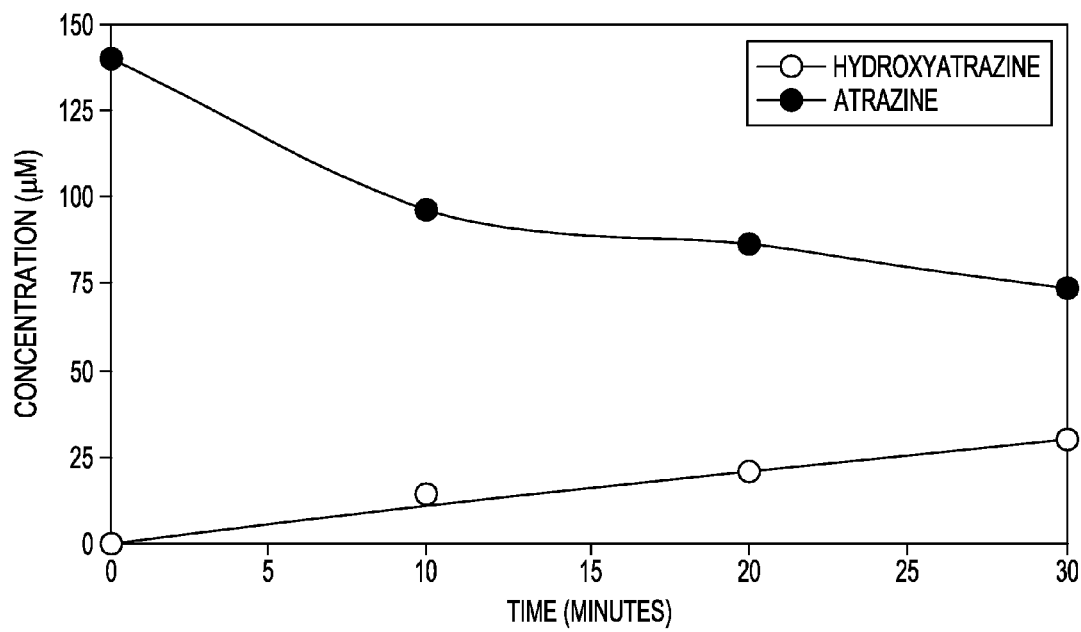
Figure 24:
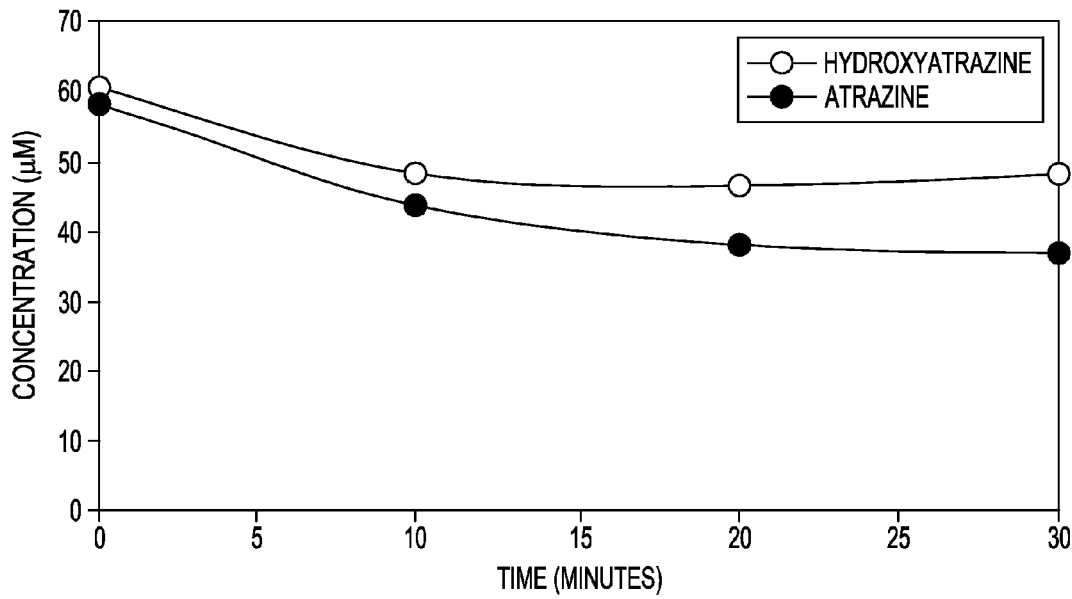
FIG. 24 illustrates adsorption of atrazine and hydroxyatrazine in cell-free microbeads, in accord with various embodiments.

Atrazine degradation activity of the encapsulated microorganisms was evaluated using HPLC analysis. Due to the high atrazine adsorption characteristic of the gels, the rate of hydroxyatrazine production was used in all activity calculations. FIG. 23 shows changes in atrazine and hydroxyatrazine concentration in solution: (A) adsorption of atrazine, (B) adsorption and biodegradation of atrazine (n=3). The error bars are smaller than the symbols. FIG. 23A illustrates the atrazine adsorption ability of the gels by showing the change in atrazine concentration when exposed to silica beads that do not contain any cells. In the first 10 minutes, there was almost a 30% decrease in atrazine concentration in the solution followed by equilibration. As expected, hydroxyatrazine was not detected in this solution due to the absence of the enzyme AtzA. FIG. 23B shows the drop in atrazine concentration via the combined effect of atrazine adsorption by the silica gel and the degradation of the atrazine by the encapsulated cells. The rate of hydroxyatrazine production was linear over time, which indicated that hydroxyatrazine had less affinity to the silica gel and was more readily released into the solution environment. This observation was supported by assays similar to those shown in FIG. 23A but with hydroxyatrazine and cell-free beads (FIG. 24). FIG. 24 shows adsorption of atrazine and hydroxyatrazine in cell-free microbeads.

Table 8 summarizes the results of the atrazine conversion activities obtained using different gel compositions and geometries (cylinder block vs. microspheres). The activity in cylinder blocks was significantly lower than those encapsulated in microbeads. This result was expected since only one surface of the cylinder was exposed to the solution and therefore only the cells very close to the surface of the product were involved in degradation of the atrazine. Cells encapsulated in N1 and N2 gels in cylinder blocks had only 16%, and 22% of the activity of the free cells in solution. As expected, gels that contained cells that did not express AtzA (N3) or gels that did not contain any cells (N4) did not show any hydroxyatrazine production. It was not possible to test the N1 and N2 gels in microbead form since the microbeads did not show any mechanical integrity and easily pulverized. This made them unsuitable for any bioremediation application in the field. On the other hand, the N5 gels could easily be manufactured in the form of cylinder blocks and microbeads. Note the significant increase in specific activity when the cells were encapsulated in the high specific surface area microbeads (N5*) when compared to the gels encapsulated in a cylinder block of limited specific surface area (N5).

TABLE 8

Comparison of normalized activity of encapsulated and free *E. coli* expressing AtzA in different gels.

| Gel Type | Normalized Specific Activity [μmol/min · g] Hydroxyatrazine |
|---|---|
| N1 | 0.159 |
| N2 | 0.224 |
| N3[a] | 0.000 |
| N4[b] | 0.000 |

TABLE 8-continued

Comparison of normalized activity of encapsulated and
free E. coli expressing AtzA in different gels.
Normalized Specific Activity [µmol/min · g]

| Gel Type | Hydroxyatrazine |
|---|---|
| N5 | 0.124 |
| N5* | 0.953* ± 0.35 |
| Free Cells | 1.000 |

Note that (*) indicates microbeads. Rests of the gels were tested in cylinder form. N3 gels contained non-expressing cells, N4 gels did not contain cells. Activity was measured at room temperature after 24 h of encapsulation.

Figure 25:
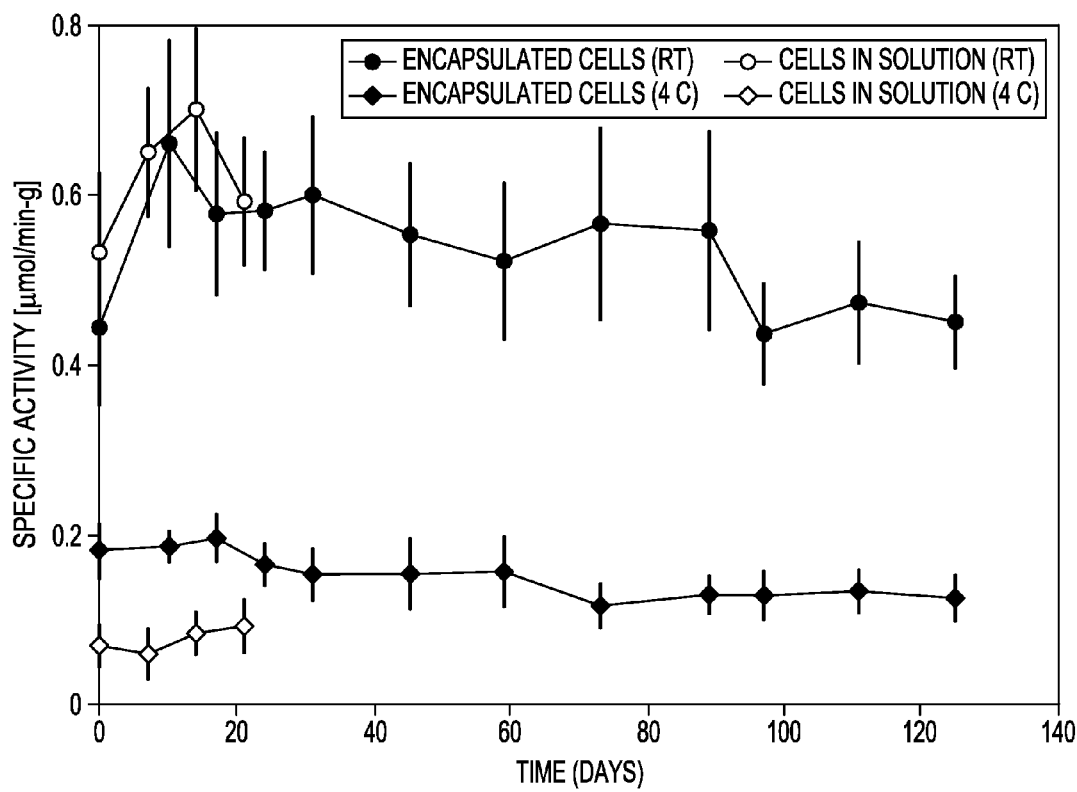
FIG. 25 illustrates the specific activity of non-viable *E. coli* expressing AtzA in N5* microbeads at different temperatures, in accord with various embodiments.

FIG. 25 shows the activities of the free and microbead encapsulated cells (N5*) over 4 months. When the activity was measured at room temperature, free cells showed an average of 0.61±0.04 mmol/g-min of activity over 21 days. After 21 days, significant cell lysis was observed in the free cells; this was likely due to long-term hypoosmotic stress induced by water. Therefore, the experiments on the free cells were stopped at that time point. On the other hand, cells encapsulated in N5 porous gels (microbeads) showed a stable activity between 0.44±0.06 µmol/g-min to 0.66±0.12 µmol/g-min for up to 4 months. This showed that even though the encapsulated cells were dead and had lost their membrane integrity, AtzA was protected and active in the silica matrix. The activities of the free and encapsulated cells were found to be temperature dependent. At 4° C., activity dropped by 45% and 30% for the free and encapsulated cells, respectively. The activity of encapsulated cells was 33.3% higher than the cells in solution.

Figure 26:
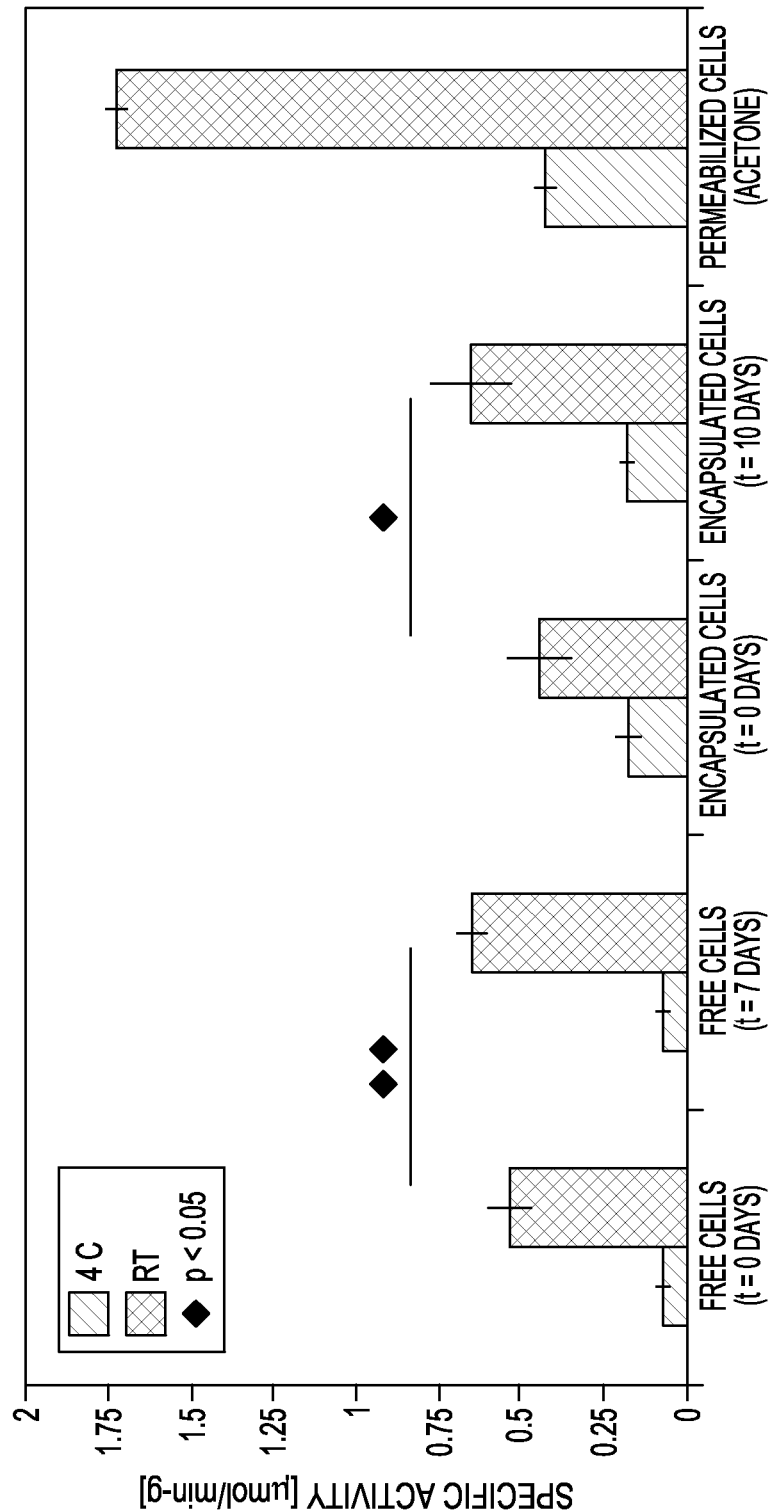
FIG. 26 illustrates a comparison of specific activity of *E. coli* expressing AtzA at different conditions (n=3), in accord with various embodiments.

For activity measurements at room temperature, at 10 days of encapsulation (~7 days for free cells), there was an increase in the specific activity, which was attributed to an increase in the permeability of the membranes since the viability of the encapsulated cells (N5, 24 h at 45° C.) becomes even more negligible. This is further supported by parallel experiments with acetone as a permeabilizing agent, where cells showed higher activities when compared to free and encapsulated cells (FIG. 26). FIG. 26 shows a comparison of specific activity of E. coli expressing AtzA at different conditions (n=3). Statistical analysis was performed using ANOVA test. However, for activity measurements at 4° C., the improvement was only significant for cells in acetone; which indicated that the activity of the enzyme not only depended on the permeability of the membrane but also on the temperature at which the assays were carried out.

Biodegradation of Atrazine Using AtzA Enzyme Encapsulated in Silica Gel.

Figure 27:
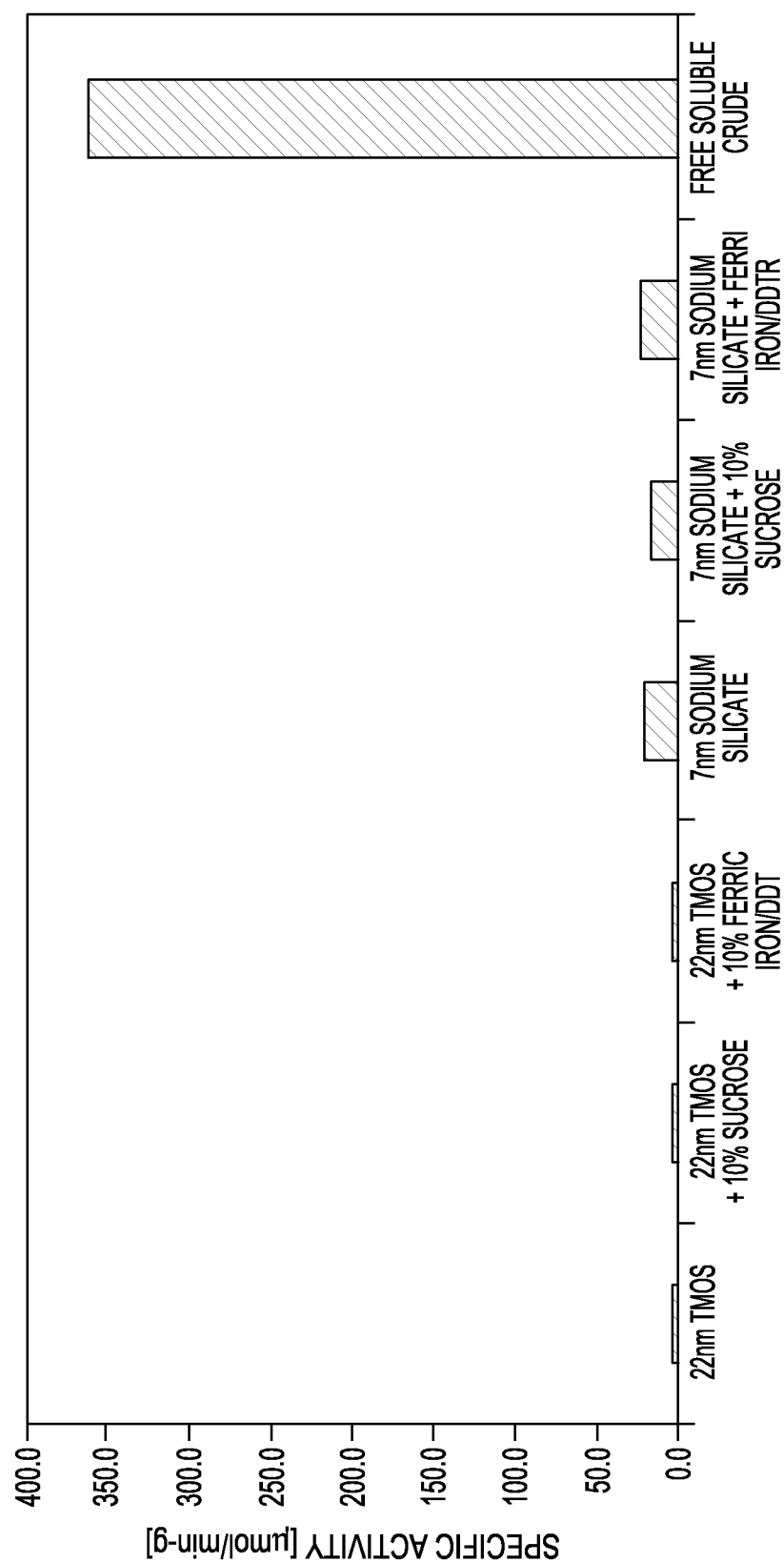
FIG. 27 illustrates the specific activity of various silica gels containing free AtzA with and without additive, in accord with various embodiments.

AtzA-expressing E. coli cells were lysed (ruptured) by passage through a French Press cell and the soluble protein fraction was collected. This soluble free protein was encapsulated in two different silica gels and two different additives were added in an attempt to increase activity: 1) sucrose was added to coat the silica and prevent protein binding to the surface and inactivation, and 2) iron was added to make the AtzA enzyme fully active (AtzA contains Fe(II) that is coordinated in the active site by histidine and aspartic acid ligands). Activity in all cases was low (FIG. 27) compared to free enzyme in solution. FIG. 27 shows specific activity of various silica gels containing free AtzA with and without additives. The activity of the silica gels is much lower than that of the free enzyme in solution (the farthest bar to the right). Additives had little effect on activity. Protein was released from the gels. The 7 nm sodium silicate gels had higher activity that can likely be attributed to higher protein release.

In sum, method consisted of the encapsulation of recombinant E. coli expressing AtzA in porous silica gels. The synergistic interaction between the porous silica and the cells allowed the adsorption and biodegradation of the atrazine for over 4 months. The rates of conversion of atrazine by the encapsulated cells depended on the precursors used for the synthesis of the porous gels and on their final geometries (e.g., films or microbeads). When microbeads were used the rates of biodegradation of atrazine were close to the values obtained with free cells.

Example 13. Treatment of Fracking Water

Materials and Methods.

The gel consisted of colloidal silica nanoparticles Ludox® TM40 (40% w/w), tetramethyl orthosilicate (TMOS, 98%) and methyltrimethoxy silane (MTMOS, 97%) The organic polymer, polyethylene glycol (PEG, molecular weight ($M_w$): 600 Da), was incorporated into the porous matrix in order to increase biocompatibility of the matrix. All of the materials were purchased from Sigma (Sigma-Aldrich Corp. St. Louis, Mo.).

Microorganisms.

Experiments were conducted with two different strains of Pseudomonas putida: F1 and NCIB 9816. NCIB 9816 strain was grown on Stainer's medium with the addition of 0.2% (w/v) pyruvate as a carbon source in the presence of 0.05% (w/v) anthranilate to activate the naphthalene degrading genes. F1 strain was grown on Stainer's medium with toluene vapors. Bacteria were culture for 16 hours. Bacteria were centrifuged at 9000 rpm for 20 min, the pellet washed with PBS, centrifuged again and then suspended in PBS at the concentrations indicated in Table 9.

Encapsulation Methods.

Bacteria were encapsulated in silica or silica-PEG (SPEG) gels. Porous gels were formed by first diluting TM40 silica nanoparticles in 1×PBS or in ultra pure water (with electrical resistivity>18.2 MΩ·cm at 25° C.). PEG ($M_w$=600 Da) was added to the solution at a volume ratio of 1:4 ($r_{PEG}$). The resulting TM40-PEG solution was cooled in an ice bath. Separately, TMOS or TMOS/MTMOS was hydrolyzed by sonication in the presence of 0.01 M HCl. A typical volume ratio was 1:1:0.1 for TMOS/water/HCl and 1:1:1.5:0.15 for TMOS/MTMOS/water/HCl. The hydrolyzed solution was mixed with the TM40-PEG solution at a volume ratio of 1:2 ($r_{cl}$). Finally, a cell suspension (0.2 g of cells/ml) was added to the mixture at a volume ratio of 1:1 ($r_{cs}$). The material was transferred to glass molds and were cured at room temperatures or formed into beads using a water-in-oil (W/O) emulsion technique. Briefly, the silica-bacteria material was loaded into a syringe and pushed out a needle, dropping the silica-bacteria solution into mineral oil and forming beads. The silica composition was optimized to polymerize immediately after dropping in the oil. The final product was also formulated as cylinder blocks (~1 ml in volume formed inside a scintillation vial, resulting in a diameter of approximately 25 mm and a thickness 2 mm).

TABLE 9

Silica gel compositions.

| Gel Type | Precursor [M] | PEG $r_{PEG}$ [v/v] | Cross-Linker Type | $r_{Cl}$ [v/v] | Bacteria $r_{Cs}$ [v/v] | [g of cell/mL] | Incubation [° C.] |
|---|---|---|---|---|---|---|---|
| N2* | 1.13 | 0.25 | I | 0.5 | 1 | 0.2 | 23 |
| N5 | 1.71 | 0.25 | II | 0.5 | 1 | 0.2 | 23 |
| N5* | 1.71 | 0.25 | II | 0.5 | 1 | 0.2 | 23 |

*Cells and silica nanoparticles diluted in 1X PBS, I: TMOS:Water:0.01M HCL (1:1:0.1 v/v/v), II: TMOS:MTMOS:Water:0.01M HCL (1:1:1.5:0.15 v/v/v/v), $r_{PEG}$ = volume of PEG/volume of precursor, $r_{cl}$ = volume of cross-linker/volume of precursor, $r_{cs}$ = volume of cell solution/volume of precursor.

Biodegradation and Metabolic Activity Assay.

The encapsulated bacteria metabolic activity was tested immediately after encapsulation by using biphenyl. The encapsulated cells are stored in Stainer's medium at 4 C. The stored encapsulated bacteria were then tested again at a later date. Biphenyl, Styrene and a variety of indole compounds can also be used to show activity of bacteria biodegradation pathways. The compound used to show active degradation pathways varied depending on the bacteria. In the case of NCIB-9816, Biphenyl was used to quantify biodegradation activity of bacteria. Biphenyl was degraded by the bacteria to 2-hydroxy-6-oxo-6-phenylhexa-2,4-dienoic acid, which was yellow in color and could be quantified using spectrophotometry ($\lambda$=435). In the case of F1, styrene was used to quantify biodegradation activity. Styrene was degraded by the bacteria to 2-hydroxy-6-oxo-octa-2,4,7-trienoic acid, which could also be quantified using spectrophotometry ($\lambda$=410).

Results.

Figure 28:
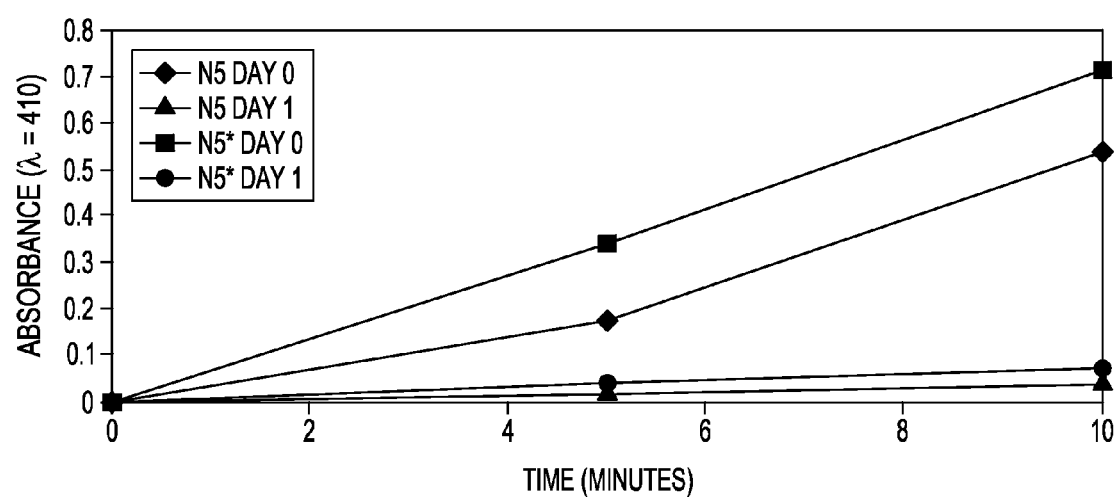
FIG. 28 illustrates the degradation of styrene by silica gel-encapsulated *Pseudomonas putida*, in accord with various embodiments.

*Pseudomonas putida* F1 were grown on toluene and were encapsulated using gel formula N5 and N5*. The degradation product of styrene was yellow and could be quantified by measuring the absorbance at $\lambda$=410. FIG. 28 shows degradation of styrene by silica gel encapsulated *Pseudomonas putida* F1 in gel formula N5. FIG. 28 indicates that using PBS is initially more beneficial to the activity. After N5* and N5 gel formulas were stored in PBS and water for one day, similar drastic drops in activity were observed.

Figure 29A:
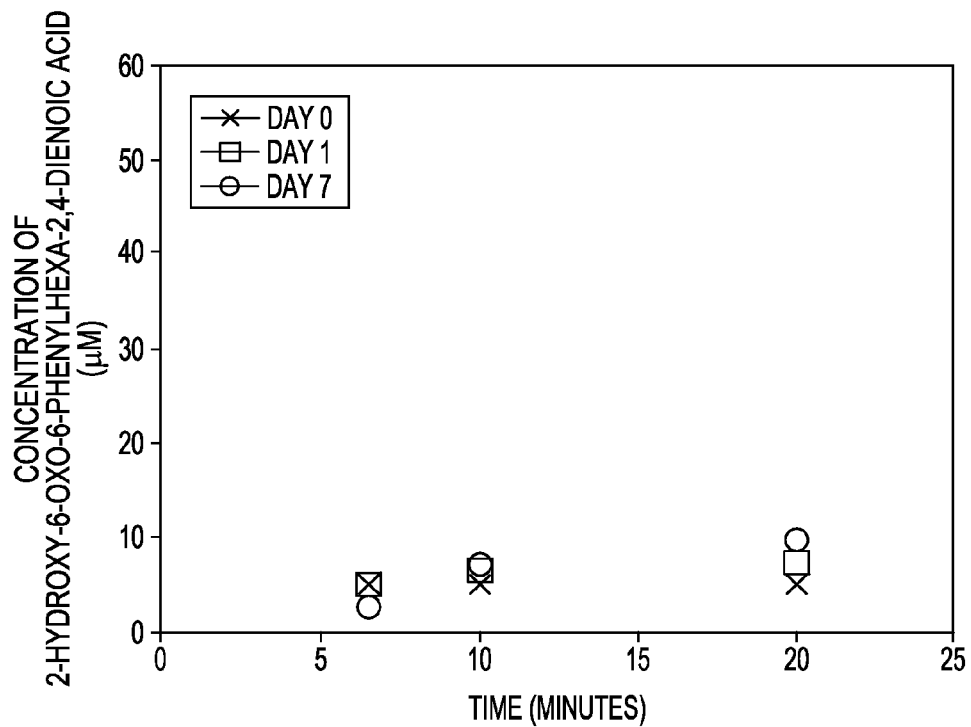
FIGS. 29A and B illustrate the degradation of biphenyl by silica gel-encapsulated *Pseudomonas putida*, in accord with various embodiments.
Figure 29B:
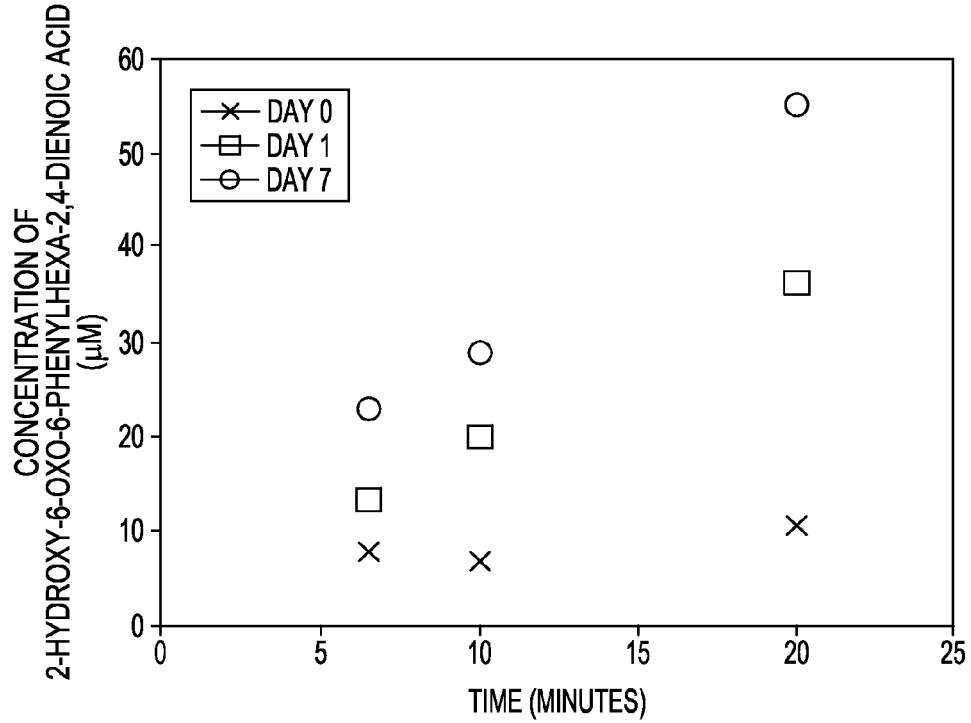

The bacterial pathways for biodegradation of fracking fluid require metabolically active cells. This is in contrast to the cells used in the atrazine application, which were treated in such a way that the viability was near zero. To increase viability, formula N5 used in the atrazine application was modified slightly. Although N5* increased degradation activity, FIG. 29 indicates that bacteria encapsulated in formula N5* are less metabolically active compared to cells encapsulated in N2*. *Pseudomonas* NCIB 9816 encapsulated in formula N2* remained metabolically active after 7 days of storage as shown in FIG. 29. FIG. 29 shows biphenyl degradation of *Pseudomonas putida* NCIB 9816 encapsulated in A) formula N5* B) formula N2*, all gels were stored in plant-based solvent (PBS, e.g. organic solvent).

Figure 30:
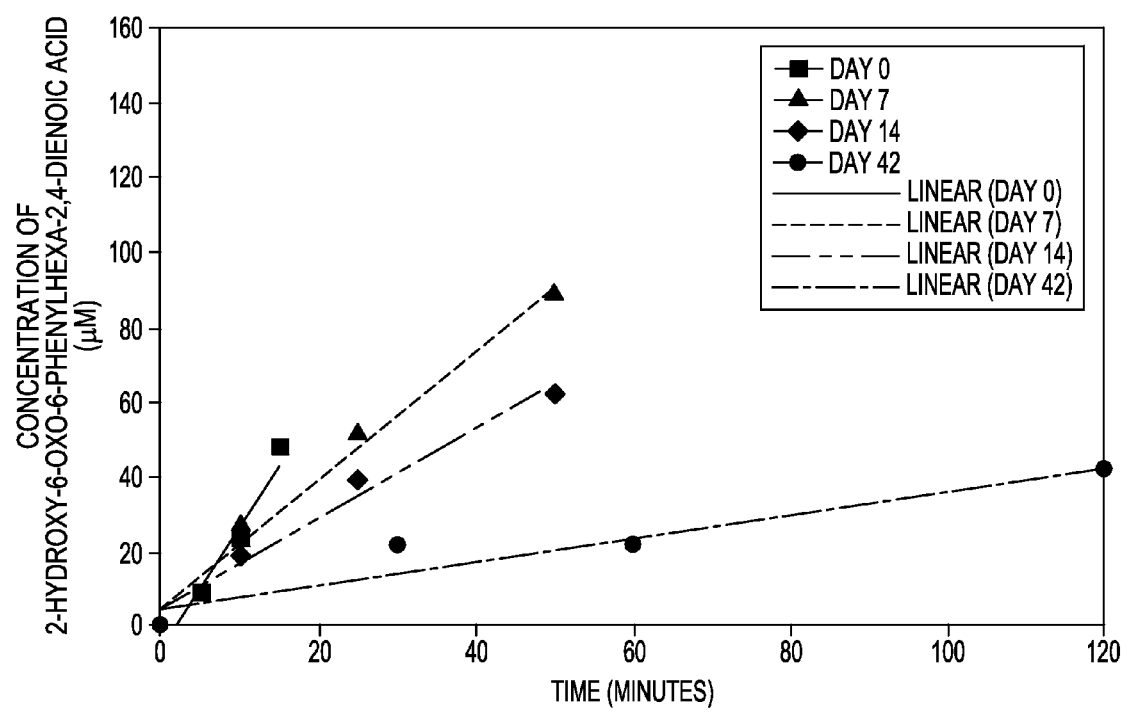
FIG. 30 illustrates the degradation of biphenyl by silica gel-encapsulated *Pseudomonas putida*, in accord with various embodiments.

Storage conditions have a large effect on the long-term activity of encapsulated *Pseudomonas putida* NCIB 9816 in N2* gel as shown in FIG. 30. FIG. 30 shows biphenyl degradation of *Pseudomonas putida* NCIB 9816 encapsulated in N2* and stored in carbon-free minimal media. At day 7, N2* gels stored in carbon-free minimal media were four times more metabolically active on biphenyl degradation than the same gels stored in PBS. N2* gels stored in carbon-free minimal media were metabolically active 42 days after encapsulation as shown in FIG. 30.

For biodegradation pathways to be active, the cells must be metabolically active. The data indicates that bacteria encapsulated in N2* gels with storage in carbon-free minimal media increases the longevity of metabolic activity.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Additional Embodiments

The present invention provides for the following exemplary embodiments:

Embodiment 1 provides a composition for formation of a silica-matrix encapsulated biomaterial, including a reactive silicon compound; and, a biomaterial with a catalytic ability; wherein the silica-encapsulated biomaterial at least partially retains its catalytic ability.

Embodiment 2 provides the composition of embodiment 1, wherein the catalytic ability of the silica-encapsulated biomaterial includes conversion of atrazine into a different compound, the conversion of a fracking chemical to a less toxic compound, or the conversion of a gas to a less flammable, less explosive, or less toxic compound.

Embodiment 3 provides the composition of any one of embodiments 1-2, wherein the biomaterial includes a microorganism.

Embodiment 4 provides the composition of any one of embodiments 1-3, wherein the biomaterial includes at least one of a bacteria, archaea, protist, fungi, or enzyme.

Embodiment 5 provides the composition of any one of embodiments 1-4, wherein the biomaterial includes at one layer of silica coating.

Embodiment 6 provides the composition of any one of embodiments 1-5, wherein the layer of silica coating is applied using treatment with flux of a gaseous silicon alkoxide.

Embodiment 7 provides the composition of any one of embodiments 4-6, wherein the enzyme causes at least part of the catalytic activity, or wherein the bacteria, archaea, protist, or fungi expresses at least one enzyme that causes the at least part of the catalytic activity.

Embodiment 8 provides the composition of any one of embodiments 4-7, wherein the enzyme is atrazine chlorohydrolase (AtzA), or wherein the bacteria, archaea, protist, or fungi expresses AtzA.

Embodiment 9 provides the composition of any one of embodiments 1-8, wherein the reactive silicon compound includes a silanol.

Embodiment 10 provides the composition of any one of embodiments 1-9, wherein the reactive silicon compound includes a silanol provided by hydrolysis of an alkoxysilane.

Embodiment 11 provides the composition of embodiment 10, wherein the hydrolysis is acid-catalyzed hydrolysis.

Embodiment 12 provides the composition of any one of embodiments 10-11, wherein the hydrolysis is base-catalyzed hydrolysis.

Embodiment 13 provides the composition of any one of embodiments 10-12, wherein alkanol byproducts from hydrolysis of the alkoxysilane have been substantially removed.

Embodiment 14 provides the composition of any one of embodiments 1-13, wherein the reactive silicon compound includes a compound provided by hydrolysis of an alkoxysilane.

Embodiment 15 provides the composition of embodiment 14, wherein the alkoxysilane includes a silicon compound substituted with at least one $C_{1-20}$ alkoxy group.

Embodiment 16 provides the composition of embodiment 15, wherein the $C_{1-20}$ alkoxy group is further substituted with a functional group selected from the group consisting of H, hydroxyl, $C_{1-20}$ alkoxy, $C_{1-20}$ alkyl, $C_{1-20}$ alkylthio, amino, halo, nitro, mercapto, cyano, isocyanato, $C_{1-20}$ alkyloyl, $C_{5-10}$ cycloalkyl, $C_{6-10}$ aryl, and $C_{1-10}$ heterocycle; wherein the aryl or heterocycle is further substituted with a functional group selected from the group consisting of H, hydroxyl, $C_{1-20}$ alkoxy, $C_{1-20}$ alkyl, $C_{1-20}$ alkylthio, amino, halo, nitro, mercapto, cyano, and isocyanato.

Embodiment 17 provides the composition of embodiment 16, wherein the alkoxysilane includes a silicon compound substituted with four independently selected $C_{1-20}$ alkoxy groups.

Embodiment 18 provides the composition of embodiment 17, wherein the four independently selected $C_{1-20}$ alkoxy groups are the same.

Embodiment 19 provides the composition of any one of embodiments 1-18, wherein the reactive silicon compound includes a compound provided by hydrolysis of at least one of tetramethylorthosilicate (TMOS), tetraethylorthosilicate (TEOS), tetrakis(2-hydroxyethyl)orthosilicate (THEOS), methyldiethoxysilane (MDES), 3-(glycidoxypropyl)triethoxysilane (GPTMS),3-(trimethyoxysilyl)propylacrylate (TMSPA), N-(3-triethoxysilylpropyl)pyrrole (TESPP), vinyltriethyoxysilane (VTES), methacryloxypropyltriethoxysilane (TESPM), diglycerylsilane (DGS), methyltriethoxysilane (MTMOS), trimethylmethoxysilane (TMMS), ethyltriethoxysilane (TEES), n-propyltriethoxysilane (TEPS), n-butyltriethyoxysilane (TEBS),3-aminopropyltriethoxysilane (APTS),2-(2,4-dinitrophenylamino)propyltriethoxysilane, mercaptopropyltriethoxysilane (TEPMS),2-(3-aminoethylamino)propyltriethoxysilane, isocyanatopropyltriethoxysilane, hydroxyl-terminated polydimethylsiloxane, triethoxysilyl-terminated polydimethylsiloxane, methyltriethoxysilane (MTES), or triethoxysilyl-terminated poly(oxypropylene).

Embodiment 20 provides the composition of any one of embodiments 1-19, wherein the reactive silicon compound includes a compound provided by treatment of a silicate with acid.

Embodiment 21 provides the composition of any one of embodiments 1-20, wherein the reactive silicon compound includes a compound provided by treatment of an aqueous solution of a silicate salt with acid.

Embodiment 22 provides the composition of embodiment 21, wherein the aqueous solution of the silicate salt is formed by treatment of silica with a base.

Embodiment 23 provides the composition of any one of embodiments 1-22, wherein the reactive silicon compound includes a compound provided by the treatment of colloidal silica with acid.

Embodiment 24 provides the composition of any one of embodiments 1-23, wherein the reactive silicon compound includes a silanol provided by treatment with acid of an aqueous sodium silicate solution or an aqueous potassium silicate solution.

Embodiment 25 provides the composition of any one of embodiments 1-24, further including water.

Embodiment 26 provides the composition of any one of embodiments 1-25, further including an organic precursor.

Embodiment 27 provides the composition of embodiment 26, wherein the organic precursor includes at least one of a synthetic polymer or monomer, a natural polymer or monomer, or an amino acid.

Embodiment 28 provides the composition of embodiment 26, wherein the organic precursor includes a hydroxyl-terminated polymer.

Embodiment 29 provides the composition of embodiment 26, wherein the organic precursor includes a polymer terminating in at least one of hydroxyl, amino, vinyl, or carboxylic acid.

Embodiment 30 provides the composition of embodiment 26, wherein the organic precursor includes a hydroxyl-terminated poly(alkyleneoxide) polymer, wherein each alkyleneoxide unit is individually a $C_{1-10}$ alkylene oxide, wherein the polymer is at least one of linear or branched.

Embodiment 31 provides the composition of embodiment 26, wherein the organic precursor includes at least one of a saccharide or polysaccharide.

Embodiment 32 provides the composition of embodiment 26, wherein the organic precursor includes trehalose.

Embodiment 33 provides the composition of embodiment 26, wherein the organic precursor includes at least one of polyethylene glycol (PEG), polyvinyl alcohol (PVA), polyacrylic acid (HPAA), polymethyl methacrylate (PMMA), poly(2-hydroxyethyl methacrylate) (PHEMA), Pluronic™ F127 (ethylene oxide polypropylene oxide block copolymer), or Pluronic™ P123 (ethylene oxide propylene oxide ethylene oxide triblock copolymer).

Embodiment 34 provides the composition of embodiment 26, wherein the organic precursor includes at least one of a peptide, amino acid, alginate, gelatin, chitosan, sucrose, trehalose, dextrin, casein, bovine serum, or collagen.

Embodiment 35 provides the composition of any one of embodiments 1-34, further including silica.

Embodiment 36 provides the composition of any one of embodiments 1-35, further including silica nanoparticles.

Embodiment 37 provides the composition of any one of embodiments 1-37, further including colloidal silica.

Embodiment 38 provides the composition of any one of embodiments 1-38, further including colloidal silica nanoparticles.

Embodiment 39 provides the composition of any one of embodiments 1-39, wherein the pH of the composition is between about 5 and about 10.

Embodiment 40 provides the composition of any one of embodiments 1-40, wherein the pH of the composition is adjusted sufficiently to allow formation of the silica-encapsulated biomaterial within about 5 min to about 24 hours.

Embodiment 41 provides the composition of any one of embodiments 1-41, wherein the pH of the composition is adjusted sufficiently to allow gelation of the composition within about 5 min to about 24 hours.

Embodiment 42 provides the silica-matrix encapsulated biomaterial formed from the composition of any one of embodiments 1-41.

Embodiment 43 provides a method of making a silica-encapsulated biomaterial, the method including providing the composition of any one of embodiments 1-42; and, forming the silica-encapsulated biomaterial from the composition.

Embodiment 44 provides a method of making a silica-matrix encapsulated biomaterial, the method including providing a reactive silicon compound; adding a biomaterial with a catalytic ability; and, forming a silica-encapsulated biomaterial from the reactive silicon compound composition, wherein the silica-encapsulated biomaterial at least partially retains its catalytic ability.

Embodiment 45 provides the method of embodiment 44, wherein forming includes a condensation reaction, wherein the reactive silicon compound is a reactant in the condensation reaction.

Embodiment 46 provides the method of any one of embodiments 44-45, wherein forming includes dropping the composition into an oil-medium to form beads or spheres of the silica-matrix encapsulated biomaterial.

Embodiment 47 provides the method of any one of embodiments 44-46, wherein forming includes allowing sufficient time to pass to form the silica-encapsulated biomaterial.

Embodiment 48 provides the method of any one of embodiments 44-47, wherein forming includes reducing movement of the composition to form the silica-encapsulated biomaterial.

Embodiment 49 provides the method of any one of embodiments 44-48, wherein forming includes adjusting the pH of the composition.

Embodiment 50 provides the method of any one of embodiments 44-49, wherein forming includes heating the composition.

Embodiment 51 provides the method of any one of embodiments 44-50, further including adjusting the pH of the reactive silicon compound composition between about 5 and about 10.

Embodiment 52 provides the method of any one of embodiments 44-51, further including adjusting the pH of the composition sufficiently to enable formation of the silica-encapsulated biomaterial within about 5 min to about 24 hours.

Embodiment 53 provides the method of any one of embodiments 44-52, further including adjusting the pH of the composition sufficiently to allow gelation of the composition within about 5 min to about 24 hours.

Embodiment 54 provides the method of any one of embodiments 44-53, wherein providing the biomaterial includes providing a microorganism.

Embodiment 55 provides the method of any one of embodiments 44-54, wherein providing the biomaterial includes providing at least one of a bacteria, archaea, protist, fungi, or enzyme.

Embodiment 56 provides the method of any one of embodiments 44-55, further including forming at least one layer of silica coating on the biomaterial prior to encapsulation in the silica-matrix.

Embodiment 57 provides the method of embodiment 56, wherein forming the at least one layer includes treating with flux of a gaseous silicon alkoxide.

Embodiment 58 provides the method of embodiment 55, wherein the enzyme causes at least part of the catalytic ability, or wherein the bacteria, archaea, protist, or fungi expresses at least one enzyme, wherein the enzyme causes at least part of the catalytic ability.

Embodiment 59 provides the method of embodiment 55, wherein the enzyme is atrazine chlorohydrolase (AtzA), or wherein prior to encapsulation the bacteria, archaea, protist, or fungi expresses AtzA.

Embodiment 60 provides the method of any one of embodiments 44-59, wherein the reactive silicon compound includes a silanol.

Embodiment 61 provides the method of any one of embodiments 44-60, wherein providing the reactive silicon compound includes hydrolyzing an alkoxysilane to provide a silanol.

Embodiment 62 provides the method of embodiment 61, wherein the hydrolysis of the alkoxysilane is catalyzed by acid.

Embodiment 63 provides the method of any one of embodiments 61-62, wherein hydrolysis of the alkoxysilane is catalyzed by at least one of hydrochloric acid, phosphoric acid, nitric acid, sulfuric acid, acetic acid, citric acid, formic acid, propionic acid, oxalic acid, or carbonic acid.

Embodiment 64 provides the method of embodiment 61, wherein the hydrolysis is catalyzed by base.

Embodiment 65 provides the method of embodiment 61, wherein providing the reactive silicon compound includes removing the alkanol byproducts of hydrolysis of the alkoxysilane.

Embodiment 66 provides the method of any one of embodiments 44-65, wherein providing the reactive silicon compound includes hydrolyzing an alkoxysilane.

Embodiment 67 provides the method of embodiment 66, wherein the alkoxysilane includes a silicon compound substituted with at least one $C_{1-20}$ alkoxy group.

Embodiment 68 provides the method of embodiment 67, wherein the $C_{1-20}$ alkoxy group is further substituted with a functional group selected from the group consisting of H, hydroxyl, $C_{1-20}$ alkoxy, $C_{1-20}$ alkyl, $C_{1-20}$ alkylthio, amino, halo, nitro, mercapto, cyano, isocyanato, $C_{1-20}$ alkyloyl, $C_{5-10}$ cycloalkyl, $C_{6-10}$ aryl, and $C_{1-10}$ heterocycle; wherein the aryl or heterocycle is further substituted with a functional group selected from the group consisting of H, hydroxyl, $C_{1-20}$ alkoxy, $C_{1-20}$ alkyl, $C_{1-20}$ alkylthio, amino, halo, nitro, mercapto, cyano, and isocyanato.

Embodiment 69 provides the method of embodiment 67, wherein the alkoxysilane includes a silicon compound substituted with four independently selected $C_{1-20}$ alkoxy groups.

Embodiment 70 provides the method of embodiment 69, wherein the four independently selected $C_{1-20}$ alkoxy groups are the same.

Embodiment 71 provides the method of any one of embodiments 44-70, wherein providing the reactive silicon compound includes hydrolyzing at least one of tetramethylorthosilicate (TMOS), tetraethylorthosilicate (TEOS), tetrakis(2-hydroxyethyl)orthosilicate (THEOS), methyldiethoxysilane (MDES), 3-(glycidoxypropyl)triethoxysilane (GPMS),3-(trimethyoxysilyl)propylacrylate (TMSPA), N-(3-triethoxysilylpropyl)pyrrole (TESPP), vinyltriethyoxysilane (VTES), methacryloxypropyltriethoxysilane (TESPM), diglycerylsilane (DGS), methyltriethoxysilane (MTMOS), trimethylmethoxysilane (TMMS), ethyltriethoxysilane (TEES), n-propyltriethoxysilane (TEPS), n-butyltriethyoxysilane (TEBS),3-aminopropyltriethoxysilane (APTS),2-(2,4-dinitrophenylamino)propyltriethoxysilane, mercaptopropyltriethoxysilane (TEPMS),2-(3-aminoethylamino)propyltriethoxysilane, isocyanatopropyltriethoxysilane, hydroxyl-terminated polydimethylsiloxane, triethoxysilyl-terminated polydimethylsiloxane, methyltriethoxysilane (MTES), or triethoxysilyl-terminated poly(oxypropylene).

Embodiment 72 provides the method of any one of embodiments 44-71, wherein providing the reactive silicon compound includes treating a silicate with acid.

Embodiment 73 provides the method of any one of embodiments 44-72, wherein providing the reactive silicon compound includes treating an aqueous solution of a silicate salt with acid.

Embodiment 74 provides the method of embodiment 73, wherein the aqueous solution of the silicate salt is formed by treating silica with a base.

Embodiment 75 provides the method of any one of embodiments 44-74, wherein providing the reactive silicon compound includes treating a silicate-containing colloidal silica with acid.

Embodiment 76 provides the method of any one of embodiments 44-75, wherein providing the reactive silicon compound includes providing a silanol by treating an aqueous sodium silicate solution or an aqueous potassium silicate solution with acid.

Embodiment 77 provides the method of any one of embodiments 44-76, further including adding water.

Embodiment 78 provides the method of any one of embodiments 44-77, further including adding an organic precursor.

Embodiment 79 provides the method of embodiment 78, wherein adding the organic precursor includes adding at least one of a synthetic polymer or monomer, a natural polymer or monomer, or an amino acid.

Embodiment 80 provides the method of embodiment 78, wherein adding the organic precursor includes adding a hydroxyl-terminated polymer.

Embodiment 81 provides the method of embodiment 78, wherein adding the organic precursor includes adding a polymer terminating in at least one of hydroxyl, amino, vinyl, or carboxylic acid.

Embodiment 82 provides the method of embodiment 78, wherein adding the organic precursor includes adding a hydroxyl-terminated poly(alkyleneoxide) polymer, wherein each alkyleneoxide unit is individually a $C_{1-10}$ alkylene oxide, wherein the polymer is at least one of linear or branched.

Embodiment 83 provides the method of embodiment 78, wherein adding the organic precursor includes adding at least one of a saccharide or polysaccharide.

Embodiment 84 provides the method of embodiment 78, wherein adding the organic precursor includes adding trehalose.

Embodiment 85 provides the method of embodiment 78, wherein adding the organic precursor includes at least one of adding polyethylene glycol (PEG), polyvinyl alcohol (PVA), polyacrylic acid (HPAA), polymethyl methacrylate (PMMA), poly(2-hydroxyethyl methacrylate) (PHEMA), Pluronic F127, or Pluronic P123.

Embodiment 86 provides the method of embodiment 78, wherein adding the organic precursor includes at least one of adding a peptide, amino acid, alginate, gelatin, chitosan, sucrose, trehalose, dextrin, casein, bovine serum, or collagen.

Embodiment 87 provides the method of any one of embodiments 44-86, further including adding silica.

Embodiment 88 provides the method of any one of embodiments 44-87, further including adding silica nanoparticles.

Embodiment 89 provides the method of any one of embodiments 44-88, further including adding colloidal silica.

Embodiment 90 provides the method of any one of embodiments 44-89, further including adding colloidal silica nanoparticles.

Embodiment 91 provides the silica-matrix encapsulated biomaterial formed by the method of any one of embodiments 44-90.

Embodiment 92 provides a composition for formation of a silica-matrix encapsulated bacteria, including a reactive silicon compound; a bacteria with a catalytic ability; and, an organic precursor, including at least one of a synthetic polymer or monomer, a natural polymer or monomer, an amino acid, a saccharide, or a polysaccharide; wherein the pH of the composition is adjusted sufficiently to allow formation of the silica-matrix encapsulated bacteria within about 5 minutes to about 24 hours; wherein the silica-encapsulated bacteria at least partially retains its catalytic ability.

Embodiment 93 provides a composition for formation of a silica-matrix encapsulated bacteria, including a reactive silicon compound; a bacteria with a catalytic ability to transform atrazine into another compound, wherein the bacteria expresses atrazine chlorohydrolase; and, an organic precursor, including at least one of a synthetic polymer or monomer, a natural polymer or monomer, an amino acid, a saccharide, or a polysaccharide; wherein the pH of the composition is adjusted sufficiently to allow formation of the silica-matrix encapsulated bacteria within about 5 minutes to about 24 hours; wherein the silica-encapsulated bacteria at least partially retains its catalytic ability.

Embodiment 94 provides a method of making a silica-matrix encapsulated bacteria, the method including providing a reactive silicon compound; adding an organic precursor, the precursor including at least one of a synthetic polymer or monomer, a natural polymer or monomer, an amino acid, a saccharide, or a polysaccharide; adding a bacteria with a catalytic ability; adjusting the pH of the composition sufficiently to allow gelation of the composition within about 5 min to about 24 hours; and, forming a silica-encapsulated microorganism from the reactive silicon compound composition, wherein the silica-encapsulated microorganism at least partially retains its catalytic ability.

Embodiment 95 provides a method of treatment of a medium with a biomaterial, including exposing a medium to a biomaterial; wherein the biomaterial is encapsulated in a silica-matrix; wherein the biomaterial encapsulated in silica is formed from the composition of any one of embodiments 1-43.

Embodiment 96 provides a method of treatment of a medium with a biomaterial, including exposing a medium to a biomaterial; wherein the biomaterial is encapsulated in a silica-matrix; wherein the biomaterial encapsulated in silica is formed using the method of any one of embodiments 44-90.

Embodiment 97 provides a method of treatment of atrazine-containing water, including exposing an atrazine-containing water to a bacteria expressing the enzyme atrazine chlorohydrolase (AtzA), sufficient to reduce the atrazine content of the water; wherein the bacteria is encapsulated in a silica-matrix.

Embodiment 98 provides the method of embodiment 97, wherein the microbe is a bacteria.

Embodiment 99 provides the method of any one of embodiments 97-98, wherein the microbe is *E. coli*.

Embodiment 100 provides a method of treatment of fracking water, including: exposing fracking water to a biomaterial with a catalytic ability comprising conversion of a fracking chemical to a less toxic compound; wherein the biomaterial is encapsulated in a silica-matrix.

Embodiment 101 provides a method of gas abatement, including: exposing a gas to a biomaterial with a catalytic ability comprising conversion of a gas to a less flammable, less explosive, or less toxic compound; wherein the biomaterial is encapsulated in a silica-matrix.

Embodiment 102 provides a method of treating a medium, including: exposing a medium containing a chemical to a biomaterial with a catalytic ability comprising conversion of the chemical to a different chemical, sufficient to transform at least some of the chemical to the different chemical; wherein the biomaterial is encapsulated in a silica matrix.

Embodiment 103 provides the method of Embodiment 102, wherein the medium is water.

Embodiment 104 provides the method of Embodiment 102, wherein the medium is gas.

Embodiment 105 provides the composition or method of any one or any combination of Embodiments 1-104 optionally configured such that all elements or options recited are available to use or select from.

We claim:

1. A composition for formation of a silica-matrix encapsulated biomaterial, the composition comprising:
    a reactive silicon compound comprising a silanol, wherein the reactive silicon compound is a hydrolyzed alkoxysilane chosen from tetramethylorthosilicate (TMOS), tetraethylorthosilicate (TEOS), tetrakis(2-hydroxyethyl)orthosilicate (THEOS), methyldiethoxysilane (MDES), 3-(glycidoxypropyl)triethoxysilane (GPTMS), 3-(trimethyoxysilyl)propylacrylate (TMSPA), N-(3-triethoxysilylpropyl)pyrrole (TESPP), vinyltriethyoxysilane (VTES), methacryloxypropyltriethoxysilane (TESPM), diglycerylsilane (DOS), methyltrimethoxysilane (MTMOS), trimethylmethoxysilane (TMMS), ethyltriethoxysilane (TEES), n-propyltriethoxysilane (TEPS), n-butyltriethyoxysilane (TEBS), 3-aminopropyltriethoxysilane (APTS), 2-(2,4-dinitrophenylamino)propyltriethoxysilane, mercaptopropyltriethoxysilane (TEPMS), 2-(3-aminoethylamino)propyltriethoxysilane, isocyanatopropyltriethoxysilane, and methyltriethoxysilane (MTES), or a combination thereof;
    silica nanoparticles;
    an organic precursor chosen from a synthetic polymer or monomer, a natural polymer or monomer, an amino acid, a saccharide, a polysaccharide, or a combination thereof; and
    a biomaterial with a catalytic ability;
    wherein
        the silica-encapsulated biomaterial at least partially retains its catalytic ability, and
        the catalytic ability of the silica-encapsulated biomaterial at 4° C. at 0 to 20 days after encapsulation exceeds the catalytic ability of a corresponding biomaterial at 4° C. that is in aqueous solution for 0 to 20 days and that is free of encapsulation by the silica-matrix formed from the composition.

2. The composition of claim 1, wherein the catalytic ability of the silica-encapsulated biomaterial comprises conversion of atrazine into a different compound, conversion of a fracking chemical to a less toxic compound, or conversion of a gas to at least one of a less flammable, less explosive, and less toxic compound.

3. The composition of claim 1, wherein the biomaterial comprises at least one of a bacteria, archaea, protist, fungi, and enzyme.

4. The composition of claim 1, wherein at least one of
    the biomaterial causes at least part of the catalytic activity, and
    the biomaterial expresses at least one enzyme that causes the at least part of the catalytic activity.

5. The composition of claim 4, wherein the biomaterial expresses atrazine chlorohydrolase (AtzA).

6. The composition of claim 1, further comprising water.

7. The composition of claim 1, wherein the organic precursor comprises polyethylene glycol (PEG), polyvinyl alcohol (PVA), polyacrylic acid (HPAA), polymethyl methacrylate (PMMA), poly(2-hydroxyethyl methacrylate) (PHEMA), an ethylene oxide polypropylene oxide block copolymer, an ethylene oxide propylene oxide ethylene oxide triblock copolymer, or a combination thereof.

8. The composition of claim 1, wherein the organic precursor comprises polyethylene glycol (PEG).

9. The composition of claim 1, wherein the alkoxysilane is at least one of tetramethylorthosilicate (TMOS) and methyltrimethoxysilane (MTMOS).

10. The silica-matrix encapsulated biomaterial formed from the composition of claim 1.

11. A method of making the silica-matrix encapsulated biomaterial of claim 10, the method comprising:
    hydrolyzing the alkoxysilane to provide the reactive silicon compound comprising a silanol; and
    forming the silica-matrix encapsulated biomaterial of claim 10 from a reactive silicon compound composition comprising the reactive silicon compound, the silica, the organic precursor, and the biomaterial with the catalytic activity, wherein the silica-encapsulated biomaterial at least partially retains its catalytic ability.

12. The method of claim 11, wherein forming comprises dropping the composition into an oil-medium to form at least one of beads and spheres of the silica-matrix encapsulated bio material.

13. The silica-matrix encapsulated biomaterial formed by the method of claim 11.

14. A method of treating a medium, comprising:
    exposing a medium containing a chemical to the silica-matrix encapsulated biomaterial of claim 13, wherein the biomaterial has a catalytic ability comprising conversion of the chemical to a different chemical, wherein the exposing is sufficient to transform at least some of the chemical to the different chemical.

15. The method of claim 14, wherein the medium comprises water.

16. The method of claim 15, wherein the method of treating a medium is a method of treatment of fracking water, the water exposed to the biomaterial is fracking water, the chemical is a fracking chemical, and the different chemical is a less toxic chemical.

17. The method of claim 15, wherein the method of treating a medium is a method of treatment of atrazine-containing water, the chemical is atrazine, and the biomaterial is a bacteria expressing the enzyme atrazine chlorohydrolase (AtzA).

18. The method of claim 14, wherein the medium comprises gas.

19. The method of claim 14, wherein the method of treating a medium is a method of gas abatement, wherein the different chemical is at least one of less flammable, less explosive, and less toxic than the chemical that is transformed.

20. A composition for formation of a silica-matrix encapsulated biomaterial, the composition comprising:
- a reactive silicon compound comprising a silanol, wherein the reactive silicon compound is a hydrolyzed alkoxysilane chosen from tetramethylorthosilicate (TMOS), methyltrimethoxysilane (MTMOS), and a combination thereof;
- silica nanoparticles;
- an organic precursor that is polyethylene glycol (PEG); and
- a biomaterial that is a bacteria comprising a catalytic ability, wherein the bacteria expresses the enzyme atrazine chlorohydrolase (AtzA), wherein catalytic ability is the conversion of atrazine into a different compound;

wherein
- the silica-encapsulated biomaterial at least partially retains its catalytic ability, and
- the catalytic ability of the silica-encapsulated biomaterial at 4° C. at 0 to 20 days after encapsulation exceeds the catalytic ability of a corresponding biomaterial at 4° C. that is in aqueous solution for 0 to 20 days and that is free of encapsulation by the silica-matrix formed from the composition.

* * * * *

UNITED STATES PATENT AND TRADEMARK OFFICE
CERTIFICATE OF CORRECTION

PATENT NO.        : 9,790,484 B2
APPLICATION NO.   : 14/001094
DATED             : October 17, 2017
INVENTOR(S)       : Wackett et al.

It is certified that error appears in the above-identified patent and that said Letters Patent is hereby corrected as shown below:

On the Title Page

On page 2, in Column 1, item (56), under "Other Publications", Line 9, delete "atrazing" and insert --atrazine-- therefor On page 2, in Column 1, item (56), under "Other Publications", Line 10, delete "biomemetic silca"," and insert --biomimetic silica",-- therefor On page 2, in Column 1, item (56), under "Other Publications", Line 12, delete "altrazin chlorohydrase" and insert --atrazine chlorohydrolase-- therefor On page 2, in Column 1, item (56), under "Other Publications", Line 13, delete "matric."," and insert --matrix.",-- therefor In the Drawings On sheet 10 of 22, Fig. 13, delete "(40°C" and insert --(40 °C-- therefor On sheet 10 of 22, Fig. 13, delete "(40°C" and insert --(40 °C-- therefor On sheet 10 of 22, Fig. 13, delete "(40°C" and insert --(40 °C-- therefor On sheet 15 of 22, Fig. 21, delete "45°C)" and insert --45 °C)-- therefor In the Specification In Column 4, Line 56, delete "FIG." and insert --FIGS.-- therefor In Column 10, Line 7, delete "crossslinking" and insert --crosslinking-- therefor Signed and Sealed this
Twenty-third Day of April, 2019

Andrei Iancu
*Director of the United States Patent and Trademark Office*

In Column 10, Line 8, after "into", insert --the--

In Column 10, Line 15, delete "SiO2" and insert --SiO$_2$-- therefor

In Column 10, Line 18, delete "≡Si—OR+HO—Si ↔ ≡Si—O—Si≡+R—OH." and insert --≡Si-OR +HO-Si≡ ↔ ≡Si-O-Si≡ + R-OH.-- therefor In Column 10, Line 27, delete "≡Si—OH+HO—Si ↔ ≡Si—O—Si≡+H$_2$O." and insert --≡Si-OH +HO-Si≡ ↔ ≡Si-O-Si≡ +H$_2$O.-- therefor In Column 10, Table 1, Line 7, delete "-CH3," and insert -- -CH$_3$,-- therefor In Column 10, Table 1, Line 19, delete "-CH3" and insert -- -CH$_3$-- therefor In Column 10, Table 1, Line 20, delete "-CH3" and insert -- -CH$_3$-- therefor In Column 10, Table 1, Line 21, delete "-C2H5" and insert -- -C$_2$H$_5$-- therefor In Column 10, Table 1, Line 22, delete "-C3H7" and insert -- -C$_3$H$_7$-- therefor In Column 10, Table 1, Line 23, delete "-C4H9" and insert -- -C$_4$H$_9$-- therefor In Column 10, Table 1, Line 24, delete "NH2" and insert --NH$_2$-- therefor In Column 11, Table 1, Line 4, delete "NH2" and insert --NH$_2$-- therefor In Column 11, Table 1, Line 7, delete "-CH3" and insert -- -CH$_3$-- therefor In Column 11, Table 1, Line 9, delete "triethoxysilyl-termonated" and insert --triethoxysilyl-terminated-- therefor In Column 11, Table 1, Line 9, delete "-CH3" and insert -- -CH$_3$-- therefor In Column 11, Table 1, Line 11, delete "-C2H5" and insert -- -C$_2$H$_5$-- therefor In Column 12, Line 21, delete "atzA" and insert --AtzA-- therefor In Column 13, Table 2, Line 7, delete "Polyacrylicacid" and insert --Polyacrylic acid-- therefor In Column 15, Line 11, delete "0° C." and insert --0 °C.-- therefor In Column 15, Lines 22-23, delete "0° C." and insert --0 °C.-- therefor In Column 18, Line 10, delete "naphthalene-1,8-dicarboylic" and insert --naphthalene-1,8-dicarboxylic-- therefor

CERTIFICATE OF CORRECTION (continued)
U.S. Pat. No. 9,790,484 B2

In Column 19, Line 16, delete "9,10-dihydroxybenzo[α]pyrene," and insert --9,10-dihydroxybenzo[a]pyrene,-- therefor In Column 20, Line 7, delete "beta-carboxy-cis,cis-muconate," and insert --β-carboxy-cis,cis-muconate,-- therefor In Column 20, Lines 7-8, delete "gamma-carboxymucono-lactone," and insert --γ-carboxymucono-lactone,-- therefor In Column 20, Line 8, delete "beta-ketoadipate" and insert --β-ketoadipate-- therefor In Column 20, Line 9, delete "beta-ketoadipate," and insert --β-ketoadipate,-- therefor In Column 20, Table 4, Line 26, delete "dibromomethane." and insert --dibromomethane,-- therefor In Column 21, Table 4, Line 27, delete "1,3Dichloro-2-propanol," and insert --1,3-Dichloro-2-propanol,-- therefor In Column 21, Table 4, Line 40, delete "Naphthtalene-1sulfonate" and insert --Naphthalene-1-sulfonate-- therefor In Column 23, Line 47, delete "monooxide" and insert --monoxide-- therefor In Column 24, Line 47, after "manufacture", insert --.--

In Column 25, Line 20, delete "Mw=600" and insert --$M_w$=600-- therefor

In Column 25, Line 56, delete "Mw=600" and insert --$M_w$=600-- therefor

In Column 26, Line 5, delete "Mw=10" and insert --$M_w$=10-- therefor

In Column 26, Line 12, delete "0° C." and insert --0 °C.-- therefor

In Column 26, Line 18, delete "4° C." and insert --4 °C.-- therefor

In Column 26, Line 25, delete "(Mw=6" and insert --($M_w$=6-- therefor

In Column 27, Line 34, delete "atzA" and insert --AtzA-- therefor

In Column 27, Line 52, delete "4° C." and insert --4 °C.-- therefor

In Column 28, Line 5, delete "permeablilizing" and insert --permeabilizing-- therefor In Column 28, Line 6, after "12)", insert --.--

CERTIFICATE OF CORRECTION (continued)
U.S. Pat. No. 9,790,484 B2

In Column 28, Line 41, delete "(Mw=600" and insert --($M_w$=600-- therefor

In Column 28, Line 63, delete "40 C" and insert --40 °C-- therefor

In Column 30, Line 20, delete "hydroxatrazine" and insert --hydroxyatrazine-- therefor In Column 31, Line 4, delete "($r_d$)." and insert --($r_{cl}$).-- therefor In Column 31, Line 51, delete "37° C." and insert --37 °C.-- therefor In Column 33, Line 63, delete "45° C." and insert --45 °C.-- therefor In Column 35, Line 16, delete "mmol/g-min" and insert --µmol/g-min-- therefor In Column 39, Line 37, delete "(GPTMS),3-(trimethyoxysilyl)propylacrylate" and insert --(GPTMS), 3-(trimethyoxysilyl)propylacrylate-- therefor In Column 39, Lines 43-44, delete "(TEBS),3-aminopropyltriethoxysilane" and insert --(TEBS), 3-aminopropyltriethoxysilane-- therefor In Column 39, Lines 44-45, delete "(APTS),2-(2,4-dinitrophenylamino)propyltriethoxysilane," and insert --(APTS), 2-(2,4-dinitrophenylamino)propyltriethoxysilane,-- therefor In Column 39, Lines 45-46, delete "(TEPMS),2-(3-aminoethylamino)propyltriethoxysilane," and insert --(TEPMS), 2-(3-aminoethylamino)propyltriethoxysilane,-- therefor In Column 42, Line 57, delete "(GPMS),3-(trimethyoxysilyl)propylacrylate" and insert --(GPMS), 3-(trimethyoxysilyl)propylacrylate-- therefor In Column 42, Line 63, delete "(TEBS),3-aminopropyltriethoxysilane" and insert --(TEBS), 3-aminopropyltriethoxysilane-- therefor In Column 42, Line 64, delete "(APTS),2-(2,4-dinitrophenylamino)propyltriethoxysilane," and insert --(APTS), 2-(2,4-dinitrophenylamino)propyltriethoxysilane,-- therefor In Column 42, Lines 65-66, delete "(TEPMS),2-(3-aminoethylamino)propyltriethoxysilane," and insert --(TEPMS), 2-(3-aminoethylamino)propyltriethoxysilane,-- therefor In the Claims In Column 45, Line 43, in Claim 1, delete "n-hutyltriethyoxysilane" and insert --n-butyltriethyoxysilane-- therefor In Column 46, Line 42, in Claim 12, delete "bio material." and insert --biomaterial.-- therefor